US007229623B1

(12) United States Patent
Cheever et al.

(10) Patent No.: US 7,229,623 B1
(45) Date of Patent: Jun. 12, 2007

(54) HER-2/NEU FUSION PROTEINS

(75) Inventors: Martin A. Cheever, Mercer Island, WA (US); Dirk Gheysen, Rixensart (BE)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/632,507

(22) Filed: Aug. 3, 2000

(51) Int. Cl.
*A61K 38/17* (2006.01)
*A61K 30/00* (2006.01)
*C07K 14/71* (2006.01)

(52) U.S. Cl. ............................ 424/192.1; 424/193.1; 424/185.1; 514/2; 530/402; 530/403

(58) Field of Classification Search ............. 424/277.1, 424/184.1, 185.1, 193.1, 192.1, 198.1, 278.1, 424/279.1, 195.11, 196.11, 197.11, 188.1, 424/198.11; 514/2; 530/350, 402, 403
See application file for complete search history.

(56) References Cited

U.S. PATENT DOCUMENTS

| | | | |
|---|---|---|---|
| 4,803,072 A * | 2/1989 | Dalton et al. ............... 424/85.5 |
| 5,723,130 A * | 3/1998 | Hancock et al. .......... 424/211.1 |
| 5,726,023 A | 3/1998 | Cheever et al. |
| 5,801,005 A | 9/1998 | Cheever et al. |
| 5,811,098 A * | 9/1998 | Plowman et al. ......... 424/178.1 |
| 5,846,538 A | 12/1998 | Cheever et al. |
| 5,869,445 A * | 2/1999 | Cheever et al. ................ 514/2 |
| 5,876,712 A | 3/1999 | Cheever et al. |
| 5,962,428 A | 10/1999 | Carrano et al. |
| 6,015,567 A | 1/2000 | Hudziak et al. |
| 6,080,409 A | 6/2000 | Laus et al. |
| 6,146,632 A | 11/2000 | Momin et al. |
| 6,270,769 B1 * | 8/2001 | Raychaudhuri et al. |
| 6,287,569 B1 | 9/2001 | Kipps et al. |
| 6,333,169 B1 | 12/2001 | Hudziak et al. |
| 6,429,199 B1 | 8/2002 | Krieg et al. |
| 6,664,370 B2 | 12/2003 | Cheever et al. |
| 6,734,172 B2 | 5/2004 | Scholler et al. |
| 6,942,862 B2 | 9/2005 | Cheever et al. |
| 6,953,573 B1 | 10/2005 | Cheever et al. |
| 7,005,498 B1 | 2/2006 | Steinaa et al. |
| 2002/0018766 A1 | 2/2002 | Roberts et al. |
| 2002/0155527 A1 | 10/2002 | Stuart et al. |

FOREIGN PATENT DOCUMENTS

| | | |
|---|---|---|
| EP | 0474727 B1 | 7/1997 |
| EP | 0444181 B1 | 10/2001 |
| WO | WO 90/14357 A1 | 11/1990 |
| WO | WO91/02062 | 2/1991 |
| WO | WO 91/02062 A2 | 2/1991 |
| WO | WO91/18926 | 12/1991 |
| WO | WO95/17210 | 6/1995 |
| WO | WO96/02555 | 2/1996 |
| WO | WO 96/18409 A1 | 6/1996 |
| WO | WO 96/30514 | 10/1996 |
| WO | WO98/25574 | 6/1998 |
| WO | WO 99/46988 A1 | 9/1999 |
| WO | WO99/57981 | 11/1999 |
| WO | WO00/04927 | 2/2000 |
| WO | WO00/20027 | 4/2000 |
| WO | WO00/29582 | 5/2000 |
| WO | WO00/44899 | 8/2000 |
| WO | WO 00/44899 A1 | 8/2000 |
| WO | WO 01/74855 A2 | 10/2001 |

OTHER PUBLICATIONS

Bowie et al. Science, 1990, vol. 247, pp. 1306-1310.*
Burgess et al., J of Cell Bio. vol. 111, pp. 2129-2138, 1990.*
Lazar et al., Molecular and Cellular Biology, 1988, vol. 8, pp. 1247-1252.*
Bork, Genome Research, 2000, vol. 10, pp. 398-400.*
Osband and Ross, IMMUNOTHERAPY, pp. 193-195, 1990.*
Dermer BIO/TECHNOLOGY, vol. 12, p. 320, Mar. 1994.*
Ezzell, J. NIH Res. 1995 vol. 7 pp. 46-49.*
Spitler, Cancer Biotherapy, 1995, vol. 10, pp. 1-3.*
Chamberlain, R.S. et al. Expert Opinion on Pharmacotherapy, 1(4): 603-614, 2000.*
Bernhard, H. et al., Endocrine-Related Cancer 9: 33-44, 2002.*
Padhy, L. C. et al. Cell, 28: 866-871, 1982.*
Venanzi, F.M. et al., Journal of the National Cancer Institute, 94(23): 1808-1809, 2002.*
Schechter, A.L. et al. Nature, 312, 513-516, 1984.*
Cornelia I. Bargmann et al., "The *Neu* Oncogene Encodes an Epidermal Growth Factor Receptor-Related Protein," Jan. 1986, Nature, vol. 319, pp. 226-230.
Yasuhiro Nagata et al., "Peptides Derived From a Wild-Type Murine Proto-Oncogene c-*erb*B-2/HER2/*neu* Can Induce CTL and Tumor Suppression in Syngeneic Hosts," 1997, The American Association of Immunologists, The Journal of Immunology 159: 1336-1343.
Disis, et al., "Peptide-Based, but Not Whole Protein, Vaccines Elicit Immunity to HER-2/neu, an Oncogenic Self-Protein"; *The American Association of Immunologists* pp. 3151-3158 (1996).
Disis et al., "Peptide-Based, but Not Whole Protein, Vaccines Elicit Immunity to HER-2/neu, an Oncogenic Self-Protein", *The Journal of Immunology:* 3151-3158 (1996).
Dermer, Another Anniversary for the War on Cancer, Bio/Technology 12:320 (1994).
Disis and Cheever, Advances in Cancer Research 71:343-371 (1997).

(Continued)

*Primary Examiner*—Larry R. Helms
*Assistant Examiner*—Anne L. Holleran
(74) *Attorney, Agent, or Firm*—Virginia G. Campen

(57) ABSTRACT

The present invention is generally directed to Her-2/neu fusion proteins, nucleic acid molecules encoding Her-2/neu fusion proteins, viral vectors expressing Her-2/neu fusion proteins, and pharmaceutical compositions (e.g., vaccines) comprising the Her-2/neu fusion proteins and/or nucleic acid molecules encoding the Her-2/neu fusion proteins. The present invention is also directed to methods of treating or preventing cancer by eliciting or enhancing an immune response to the Her-2/neu protein, including for uses in the treatment of malignancies associated with the Her-2/neu oncogene.

39 Claims, 43 Drawing Sheets

OTHER PUBLICATIONS

Disis et al., Immunization with Homologous Foreign Proteins Generates Immunity Against "Self" Tumor Antigens, The FASEB Journal 10(6):A1470 (1996) ABSTRACT from Meetings, New Orleans, LA Jun. 2-6, 1996.

Ezzel et al., Cancer "Vaccines": An Idea Whose Time Has Come?, J. NIH research 7:46-49 (1995).

Osband and Ross, Problems in the investigational study and clinical use of cancer immunotherapy, Immunology Today 11(6):193-195 (1990).

Spitler, Cancer Vaccines: The Interferon Analogy, Cancer Biotherapy 10(1):1-3 (1995).

* cited by examiner

Fig. 7a (SEQ ID NO:1)

```
Met Glu Leu Ala Ala Leu Cys Arg Trp Gly Leu Leu Leu Ala Leu Leu Pro Pro Gly Ala   20
Ala Ser Thr Gln Val Cys Thr Gly Thr Asp Met Lys Leu Arg Leu Pro Ala Ser Pro Glu   40
Thr His Leu Asp Met Leu Arg His Leu Tyr Gln Gly Cys Gln Val Val Gln Gly Asn Leu   60
Glu Leu Thr Tyr Leu Pro Thr Asn Ala Ser Leu Ser Phe Leu Gln Asp Ile Gln Glu Val   80
Gln Gly Tyr Val Leu Ile Ala His Asn Gln Val Arg Gln Val Pro Leu Gln Arg Leu Arg  100

Ile Val Arg Gly Thr Gln Leu Phe Glu Asp Asn Tyr Ala Leu Ala Val Leu Asp Asn Gly  120
Asp Pro Leu Asn Asn Thr Thr Pro Val Thr Gly Ala Ser Pro Gly Gly Leu Arg Glu Leu  140
Gln Leu Arg Ser Leu Thr Glu Ile Leu Lys Gly Gly Val Leu Ile Gln Arg Asn Pro Gln  160
Leu Cys Tyr Gln Asp Thr Ile Leu Trp Lys Asp Ile Phe His Lys Asn Asn Gln Leu Ala  180
Leu Thr Leu Ile Asp Thr Asn Arg Ser Arg Ala Cys His Pro Cys Ser Pro Met Cys Lys  200

Gly Ser Arg Cys Trp Gly Glu Ser Ser Glu Asp Cys Gln Ser Leu Thr Arg Thr Val Cys  220
Ala Gly Gly Cys Ala Arg Cys Lys Gly Pro Leu Pro Thr Asp Cys Cys His Glu Gln Cys  240
Ala Ala Gly Cys Thr Gly Pro Lys His Ser Asp Cys Leu Ala Cys Leu His Phe Asn His  260
Ser Gly Ile Cys Glu Leu His Cys Pro Ala Leu Val Thr Tyr Asn Thr Asp Thr Phe Glu  280
Ser Met Pro Asn Pro Glu Gly Arg Tyr Thr Phe Gly Ala Ser Cys Val Thr Ala Cys Pro  300

Tyr Asn Tyr Leu Ser Thr Asp Val Gly Ser Cys Thr Leu Val Cys Pro Leu His Asn Gln  320
Glu Val Thr Ala Glu Asp Gly Thr Gln Arg Cys Glu Lys Cys Ser Lys Pro Cys Ala Arg  340
Val Cys Tyr Gly Leu Gly Met Glu His Leu Arg Glu Val Arg Ala Val Thr Ser Ala Asn  360
Ile Gln Glu Phe Ala Gly Cys Lys Lys Ile Phe Gly Ser Leu Ala Phe Leu Pro Glu Ser  380
Phe Asp Gly Asp Pro Ala Ser Asn Thr Ala Pro Leu Gln Pro Glu Gln Leu Gln Val Phe  400

Glu Thr Leu Glu Glu Ile Thr Gly Tyr Leu Tyr Ile Ser Ala Trp Pro Asp Ser Leu Pro  420
Asp Leu Ser Val Phe Gln Asn Leu Gln Val Ile Arg Gly Arg Ile Leu His Asn Gly Ala  440
Tyr Ser Leu Thr Leu Gln Gly Leu Gly Ile Ser Trp Leu Gly Leu Arg Ser Leu Arg Glu  460
Leu Gly Ser Gly Leu Ala Leu Ile His His Asn Thr His Leu Cys Phe Val His Thr Val  480
Pro Trp Asp Gln Leu Phe Arg Asn Pro His Gln Ala Leu Leu His Thr Ala Asn Arg Pro  500

Glu Asp Glu Cys Val Gly Glu Gly Leu Ala Cys His Gln Leu Cys Ala Arg Gly His Cys  520
Trp Gly Pro Gly Pro Thr Gln Cys Val Asn Cys Ser Gln Phe Leu Arg Gly Gln Glu Cys  540
Val Glu Glu Cys Arg Val Leu Gln Gly Leu Pro Arg Glu Tyr Val Asn Ala Arg His Cys  560
Leu Pro Cys His Pro Glu Cys Gln Pro Gln Asn Gly Ser Val Thr Cys Phe Gly Pro Glu  580
Ala Asp Gln Cys Val Ala Cys Ala His Tyr Lys Asp Pro Pro Phe Cys Val Ala Arg Cys  600

Pro Ser Gly Val Lys Pro Asp Leu Ser Tyr Met Pro Ile Trp Lys Phe Pro Asp Glu Glu  620
Gly Ala Cys Gln Pro Cys Pro Ile Asn Cys Thr His Ser Cys Val Asp Leu Asp Asp Lys  640
Gly Cys Pro Ala Glu Gln Arg Ala Ser Pro Leu Thr Ser Ile Ile Ser Ala Val Val Gly  660
Ile Leu Leu Val Val Val Leu Gly Val Val Phe Gly Ile Leu Ile Lys Arg Arg Gln Gln  680
Lys Ile Arg Lys Tyr Thr Met Arg Arg Leu Leu Gln Glu Thr Glu Leu Val Glu Pro Leu  700

Thr Pro Ser Gly Ala Met Pro Asn Gln Ala Gln Met Arg Ile Leu Lys Glu Thr Glu Leu  720
Arg Lys Val Lys Val Leu Gly Ser Gly Ala Phe Gly Thr Val Tyr Lys Gly Ile Trp Ile  740
Pro Asp Gly Glu Asn Val Lys Ile Pro Val Ala Ile Lys Val Leu Arg Glu Asn Thr Ser  760
Pro Lys Ala Asn Lys Glu Ile Leu Asp Glu Ala Tyr Val Met Ala Gly Val Gly Ser Pro  780
Tyr Val Ser Arg Leu Leu Gly Ile Cys Leu Thr Ser Thr Val Gln Leu Val Thr Gln Leu  800
```

Fig. 7b (SEQ ID NO:1)

```
Met Pro Tyr Gly Cys Leu Leu Asp His Val Arg Glu Asn Arg Gly Arg Leu Gly Ser Gln 820
Asp Leu Leu Asn Trp Cys Met Gln Ile Ala Lys Gly Met Ser Tyr Leu Glu Asp Val Arg 840

Leu Val His Arg Asp Leu Ala Ala Arg Asn Val Leu Val Lys Ser Pro Asn His Val Lys 860
Ile Thr Asp Phe Gly Leu Ala Arg Leu Leu Asp Ile Asp Glu Thr Glu Tyr His Ala Asp 880
Gly Gly Lys Val Pro Ile Lys Trp Met Ala Leu Glu Ser Ile Leu Arg Arg Arg Phe Thr 900

His Gln Ser Asp Val Trp Ser Tyr Gly Val Thr Val Trp Glu Leu Met Thr Phe Gly Ala 920
Lys Pro Tyr Asp Gly Ile Pro Ala Arg Glu Ile Pro Asp Leu Leu Glu Lys Gly Glu Arg 940
Leu Pro Gln Pro Pro Ile Cys Thr Ile Asp Val Tyr Met Ile Met Val Lys Cys Trp Met 960
Ile Asp Ser Glu Cys Arg Pro Arg Phe Arg Glu Leu Val Ser Glu Phe Ser Arg Met Ala 980
Arg Asp Pro Gln Arg Phe Val Val Ile Gln Asn Glu Asp Leu Gly Pro Ala Ser Pro Leu 1000

Asp Ser Thr Phe Tyr Arg Ser Leu Leu Glu Asp Asp Asp Met Gly Asp Leu Val Asp Ala 1020
Glu Glu Tyr Leu Val Pro Gln Gln Gly Phe Phe Cys Pro Asp Pro Ala Pro Gly Ala Gly 1040
Gly Met Val His His Arg His Arg Ser Ser Ser Thr Arg Ser Gly Gly Gly Asp Leu Thr 1060
Leu Gly Leu Glu Pro Ser Glu Glu Glu Ala Pro Arg Ser Pro Leu Ala Pro Ser Glu Gly 1080
Ala Gly Ser Asp Val Phe Asp Gly Asp Leu Gly Met Gly Ala Ala Lys Gly Leu Gln Ser 1100

Leu Pro Thr His Asp Pro Ser Pro Leu Gln Arg Tyr Ser Glu Asp Pro Thr Val Pro Leu 1120
Pro Ser Glu Thr Asp Gly Tyr Val Ala Pro Leu Thr Cys Ser Pro Gln Pro Glu Tyr Val 1140
Asn Gln Pro Asp Val Arg Pro Gln Pro Pro Ser Pro Arg Glu Gly Pro Leu Pro Ala Ala 1160
Arg Pro Ala Gly Ala Thr Leu Glu Arg Pro Lys Thr Leu Ser Pro Gly Lys Asn Gly Val 1180
Val Lys Asp Val Phe Ala Phe Gly Gly Ala Val Glu Asn Pro Glu Tyr Leu Thr Pro Gln 1200

Gly Gly Ala Ala Pro Gln Pro His Pro Pro Ala Phe Ser Pro Ala Phe Asp Asn Leu 1220
Tyr Tyr Trp Asp Gln Asp Pro Pro Glu Arg Gly Ala Pro Pro Ser Thr Phe Lys Gly Thr 1240
Pro Thr Ala Glu Asn Pro Glu Tyr Leu Gly Leu Asp Val Pro Val   .    .      1257
```

Figure 8a (SEQ ID NO: 2)

| | |
|---|---|
| Met Glu Leu Ala Ala Trp Cys Arg Trp Gly Phe Leu Leu Ala Leu Leu Pro Pro Gly Ile<br>Ala Gly Thr Gln Val Cys Thr Gly Thr Asp Met Lys Leu Arg Leu Pro Ala Ser Pro Glu<br>Thr His Leu Asp Met Leu Arg His Leu Tyr Gln Gly Cys Gln Val Val Gln Gly Asn Leu<br>Glu Leu Thr Tyr Val Pro Ala Asn Ala Ser Leu Ser Phe Leu Gln Asp Ile Gln Glu Val<br>Gln Gly Tyr Met Leu Ile Ala His Asn Gln Val Lys Arg Val Pro Leu Gln Arg Leu Arg | 20<br>40<br>60<br>80<br>100 |
| Ile Val Arg Gly Thr Gln Leu Phe Glu Asp Lys Tyr Ala Leu Ala Val Leu Asp Asn Arg<br>Asp Pro Gln Asp Asn Val Ala Ala Ser Thr Pro Gly Arg Thr Pro Glu Gly Leu Arg Glu<br>Leu Gln Leu Arg Ser Leu Thr Glu Ile Leu Lys Gly Gly Val Leu Ile Arg Gly Asn Pro<br>Gln Leu Cys Tyr Gln Asp Met Val Leu Trp Lys Asp Val Phe Arg Lys Asn Asn Gln Leu<br>Ala Pro Val Asp Ile Asp Thr Asn Arg Ser Arg Ala Cys Pro Pro Cys Ala Pro Ala Cys | 120<br>140<br>160<br>180<br>200 |
| Lys Asp Asn His Cys Trp Gly Glu Ser Pro Glu Asp Cys Gln Ile Leu Thr Gly Thr Ile<br>Cys Thr Ser Gly Cys Ala Arg Cys Lys Gly Arg Leu Pro Thr Asp Cys Cys His Glu Gln<br>Cys Ala Ala Gly Cys Thr Gly Pro Lys His Ser Asp Cys Leu Ala Cys Leu His Phe Asn<br>His Ser Gly Ile Cys Glu Leu His Cys Pro Ala Leu Val Thr Tyr Asn Thr Asp Thr Phe<br>Glu Ser Met His Asn Pro Glu Gly Arg Tyr Thr Phe Gly Ala Ser Cys Val Thr Cys | 220<br>240<br>260<br>280<br>300 |
| Pro Tyr Asn Tyr Leu Ser Thr Glu Val Gly Ser Cys Thr Leu Val Cys Pro Pro Asn Asn<br>Gln Glu Val Thr Ala Glu Asp Gly Thr Gln Arg Cys Glu Lys Cys Ser Lys Pro Cys Ala<br>Arg Val Cys Tyr Gly Leu Gly Met Glu His Leu Arg Gly Ala Arg Ala Ile Thr Ser Asp<br>Asn Val Gln Glu Phe Asp Gly Cys Lys Lys Ile Phe Gly Ser Leu Ala Phe Leu Pro Glu<br>Ser Phe Asp Gly Asp Pro Ser Ser Gly Ile Ala Pro Leu Arg Pro Glu Gln Leu Gln Val | 320<br>340<br>360<br>380<br>400 |
| Phe Glu Thr Leu Glu Glu Ile Thr Gly Tyr Leu Tyr Ile Ser Ala Trp Pro Asp Ser Leu<br>Arg Asp Leu Ser Val Phe Gln Asn Leu Arg Ile Ile Arg Gly Arg Ile Leu His Asp Gly<br>Ala Tyr Ser Leu Thr Leu Gln Gly Leu Gly Ile His Ser Leu Gly Leu Arg Ser Leu Arg<br>Glu Leu Gly Ser Gly Leu Ala Leu Ile His Arg Asn Ala His Leu Cys Phe Val His Thr<br>Val Pro Trp Asp Gln Leu Phe Arg Asn Pro His Gln Ala Leu Leu His Ser Gly Asn Arg | 420<br>440<br>460<br>480<br>500 |
| Pro Glu Glu Asp Cys Gly Leu Glu Gly Leu Val Cys Asn Ser Leu Cys Ala His Gly His<br>Cys Trp Gly Pro Gly Pro Thr Gln Cys Val Asn Cys Ser His Phe Leu Arg Gly Gln Glu<br>Cys Val Glu Glu Cys Arg Val Trp Lys Gly Leu Pro Arg Glu Tyr Val Ser Asp Lys Arg<br>Cys Leu Pro Cys His Pro Glu Cys Gln Pro Gln Asn Ser Ser Glu Thr Cys Phe Gly Ser<br>Glu Ala Asp Gln Cys Ala Ala Cys Ala His Tyr Lys Asp Ser Ser Ser Cys Val Ala Arg | 520<br>540<br>560<br>580<br>600 |
| Cys Pro Ser Gly Val Lys Pro Asp Leu Ser Tyr Met Pro Ile Trp Lys Tyr Pro Asp Glu<br>Glu Gly Ile Cys Gln Pro Cys Pro Ile Asn Cys Thr His Ser Cys Val Asp Leu Asp Glu<br>Arg Gly Cys Pro Ala Glu Gln Arg Ala Ser Pro Val Thr Phe Ile Ile Ala Thr Val Val<br>Gly Val Leu Leu Phe Leu Ile Leu Val Val Val Gly Ile Leu Ile Lys Arg Arg Arg<br>Gln Lys Ile Arg Lys Tyr Thr Met Arg Arg Leu Leu Gln Glu Thr Glu Leu Val Glu Pro | 620<br>640<br>660<br>680<br>700 |
| Leu Thr Pro Ser Gly Ala Met Pro Asn Gln Ala Gln Met Arg Ile Leu Lys Glu Thr Glu<br>Leu Arg Lys Val Lys Val Leu Gly Ser Gly Ala Phe Gly Thr Val Tyr Lys Gly Ile Trp<br>Ile Pro Asp Gly Glu Asn Val Lys Ile Pro Val Ala Ile Lys Val Leu Arg Glu Asn Thr<br>Ser Pro Lys Ala Asn Lys Glu Ile Leu Asp Glu Ala Tyr Val Met Ala Gly Val Gly Ser<br>Pro Tyr Val Ser Arg Leu Leu Gly Ile Cys Leu Thr Ser Thr Val Gln Leu Val Thr Gln | 720<br>740<br>760<br>780<br>800 |

| Figure 8b SEQ ID NO :2 | |
|---|---|
| Leu Met Pro Tyr Gly Cys Leu Leu Asp His Val Arg Glu His Arg Gly Arg Leu Gly Ser<br>Gln Asp Leu Leu Asn Trp Cys Val Gln Ile Ala Lys Gly Met Ser Tyr Leu Glu Asp Val<br>Arg Leu Val His Arg Asp Leu Ala Ala Arg Asn Val Leu Val Lys Ser Pro Asn His Val<br>Lys Ile Thr Asp Phe Gly Leu Ala Arg Leu Leu Asp Ile Asp Glu Thr Glu Tyr His Ala<br>Asp Gly Gly Lys Val Pro Ile Lys Trp Met Ala Leu Glu Ser Ile Leu Arg Arg Arg Phe | 820<br>840<br>860<br>880<br>900 |
| Thr His Gln Ser Asp Val Trp Ser Tyr Gly Val Thr Val Trp Glu Leu Met Thr Phe Gly<br>Ala Lys Pro Tyr Asp Gly Ile Pro Ala Arg Glu Ile Pro Asp Leu Leu Glu Lys Gly Glu<br>Arg Leu Pro Gln Pro Pro Ile Cys Thr Ile Asp Val Tyr Met Ile Met Val Lys Cys Trp<br>Met Ile Asp Ser Glu Cys Arg Pro Arg Phe Arg Glu Leu Val Ser Glu Phe Ser Arg Met<br>Ala Arg Asp Pro Gln Arg Phe Val Val Ile Gln Asn Glu Asp Leu Gly Pro Ser Ser Pro | 920<br>940<br>960<br>980<br>1000 |
| Met Asp Ser Thr Phe Tyr Arg Ser Leu Leu Glu Asp Asp Asp Met Gly Asp Leu Val Asp<br>Ala Glu Glu Tyr Leu Val Pro Gln Gln Gly Phe Phe Ser Pro Asp Pro Thr Pro Gly Thr<br>Gly Ser Thr Ala His Arg Arg His Arg Ser Ser Ser Thr Arg Ser Gly Gly Gly Glu Leu<br>Thr Leu Gly Leu Glu Pro Ser Glu Glu Gly Pro Pro Arg Ser Pro Leu Ala Pro Ser Glu<br>Gly Ala Gly Ser Asp Val Phe Asp Gly Asp Leu Ala Met Gly Val Thr Lys Gly Leu Gln | 1020<br>1040<br>1060<br>1080<br>1100 |
| Ser Leu Ser Pro His Asp Leu Ser Pro Leu Gln Arg Tyr Ser Glu Asp Pro Thr Leu Pro<br>Leu Pro Pro Glu Thr Asp Gly Tyr Val Ala Pro Leu Ala Cys Ser Pro Gln Pro Glu Tyr<br>Val Asn Gln Ser Glu Val Gln Pro Gln Pro Pro Leu Thr Pro Glu Gly Pro Leu Pro Pro<br>Val Arg Pro Ala Gly Ala Thr Leu Glu Arg Pro Lys Thr Leu Ser Pro Gly Lys Asn Gly<br>Val Val Lys Asp Val Phe Ala Phe Gly Gly Ala Val Glu Asn Pro Glu Tyr Leu Val Pro | 1120<br>1140<br>1160<br>1180<br>1200 |
| Arg Glu Gly Thr Ala Ser Pro Pro His Pro Ser Pro Ala Phe Ser Pro Ala Phe Asp Asn<br>Leu Tyr Tyr Trp Asp Gln Asn Ser Ser Glu Gln Gly Pro Pro Pro Ser Asn Phe Glu Gly<br>Thr Pro Thr Ala Glu Asn Pro Glu Tyr Leu Gly Leu Asp Val Pro Val . . 1258 | 1220<br>1240<br> |

Figure 9 (SEQ ID NO: 3)

| | |
|---|---|
| Met Glu Leu Ala Ala Leu Cys Arg Trp Gly Leu Leu Leu Ala Leu Leu Pro Pro Gly Ala<br>Ala Ser Thr Gln Val Cys Thr Gly Thr Asp Met Lys Leu Arg Leu Pro Ala Ser Pro Glu<br>Thr His Leu Asp Met Leu Arg His Leu Tyr Gln Gly Cys Gln Val Val Gln Gly Asn Leu<br>Glu Leu Thr Tyr Leu Pro Thr Asn Ala Ser Leu Ser Phe Leu Gln Asp Ile Gln Glu Val<br>Gln Gly Tyr Val Leu Ile Ala His Asn Gln Val Arg Gln Val Pro Leu Gln Arg Leu Arg | 20<br>40<br>60<br>80<br>100 |
| Ile Val Arg Gly Thr Gln Leu Phe Glu Asp Asn Tyr Ala Leu Ala Val Leu Asp Asn Gly<br>Asp Pro Leu Asn Asn Thr Thr Pro Val Thr Gly Ala Ser Pro Gly Gly Leu Arg Glu Leu<br>Gln Leu Arg Ser Leu Thr Glu Ile Leu Lys Gly Gly Val Leu Ile Gln Arg Asn Pro Gln<br>Leu Cys Tyr Gln Asp Thr Ile Leu Trp Lys Asp Ile Phe His Lys Asn Asn Gln Leu Ala<br>Leu Thr Leu Ile Asp Thr Asn Arg Ser Arg Ala Cys His Pro Cys Ser Pro Met Cys Lys | 120<br>140<br>160<br>180<br>200 |
| Gly Ser Arg Cys Trp Gly Glu Ser Ser Glu Asp Cys Gln Ser Leu Thr Arg Thr Val Cys<br>Ala Gly Gly Cys Ala Arg Cys Lys Gly Pro Leu Pro Thr Asp Cys Cys His Glu Gln Cys<br>Ala Ala Gly Cys Thr Gly Pro Lys His Ser Asp Cys Leu Ala Cys Leu His Phe Asn His<br>Ser Gly Ile Cys Glu Leu His Cys Pro Ala Leu Val Thr Tyr Asn Thr Asp Thr Phe Glu<br>Ser Met Pro Asn Pro Glu Gly Arg Tyr Thr Phe Gly Ala Ser Cys Val Thr Ala Cys Pro | 220<br>240<br>260<br>280<br>300 |
| Tyr Asn Tyr Leu Ser Thr Asp Val Gly Ser Cys Thr Leu Val Cys Pro Leu His Asn Gln<br>Glu Val Thr Ala Glu Asp Gly Thr Gln Arg Cys Glu Lys Cys Ser Lys Pro Cys Ala Arg<br>Val Cys Tyr Gly Leu Gly Met Glu His Leu Arg Glu Val Arg Ala Val Thr Ser Ala Asn<br>Ile Gln Glu Phe Ala Gly Cys Lys Lys Ile Phe Gly Ser Leu Ala Phe Leu Pro Glu Ser<br>Phe Asp Gly Asp Pro Ala Ser Asn Thr Ala Pro Leu Gln Pro Glu Gln Leu Gln Val Phe | 320<br>340<br>360<br>380<br>400 |
| Glu Thr Leu Glu Glu Ile Thr Gly Tyr Leu Tyr Ile Ser Ala Trp Pro Asp Ser Leu Pro<br>Asp Leu Ser Val Phe Gln Asn Leu Gln Val Ile Arg Gly Arg Ile Leu His Asn Gly Ala<br>Tyr Ser Leu Thr Leu Gln Gly Leu Gly Ile Ser Trp Leu Gly Leu Arg Ser Leu Arg Glu<br>Leu Gly Ser Gly Leu Ala Leu Ile His His Asn Thr His Leu Cys Phe Val His Thr Val<br>Pro Trp Asp Gln Leu Phe Arg Asn Pro His Gln Ala Leu Leu His Thr Ala Asn Arg Pro | 420<br>440<br>460<br>480<br>500 |
| Glu Asp Glu Cys Val Gly Glu Gly Leu Ala Cys His Gln Leu Cys Ala Arg Gly His Cys<br>Trp Gly Pro Gly Pro Thr Gln Cys Val Asn Cys Ser Gln Phe Leu Arg Gly Gln Glu Cys<br>Val Glu Glu Cys Arg Val Leu Gln Gly Leu Pro Arg Glu Tyr Val Asn Ala Arg His Cys<br>Leu Pro Cys His Pro Glu Cys Gln Pro Gln Asn Gly Ser Val Thr Cys Phe Gly Pro Glu<br>Ala Asp Gln Cys Val Ala Cys Ala His Tyr Lys Asp Pro Pro Phe Cys Val Ala Arg Cys | 520<br>540<br>560<br>580<br>600 |
| Pro Ser Gly Val Lys Pro Asp Leu Ser Tyr Met Pro Ile Trp Lys Phe Pro Asp Glu Glu<br>Gly Ala Cys Gln Pro Cys Pro Ile Asn Cys Thr His Ser Cys Val Asp Leu Asp Asp Lys<br>Gly Cys Pro Ala Glu Gln Arg Ala Ser Pro Leu Thr Ser    653 | 620<br>640 |

Figure 10 (SEQ ID NO: 4)

```
Gln Asn Glu Asp Leu Gly Pro Ala Ser Pro Leu Asp Ser Thr Phe Tyr Arg Ser Leu Leu    20
Glu Asp Asp Asp Met Gly Asp Leu Val Asp Ala Glu Glu Tyr Leu Val Pro Gln Gln Gly    40
Phe Phe Cys Pro Asp Pro Ala Pro Gly Ala Gly Gly Met Val His His Arg His Arg Ser    60
Ser Ser Thr Arg Ser Gly Gly Gly Asp Leu Thr Leu Gly Leu Glu Pro Ser Glu Glu Glu    80
Ala Pro Arg Ser Pro Leu Ala Pro Ser Glu Gly Ala Gly Ser Asp Val Phe Asp Gly Asp   100

Leu Gly Met Gly Ala Ala Lys Gly Leu Gln Ser Leu Pro Thr His Asp Pro Ser Pro Leu   120
Gln Arg Tyr Ser Glu Asp Pro Thr Val Pro Leu Pro Ser Glu Thr Asp Gly Tyr Val Ala   140
Pro Leu Thr Cys Ser Pro Gln Pro Glu Tyr Val Asn Gln Pro Asp Val Arg Pro Gln Pro   160
Pro Ser Pro Arg Glu Gly Pro Leu Pro Ala Ala Arg Pro Ala Gly Ala Thr Leu Glu Arg   180
Pro Lys Thr Leu Ser Pro Gly Lys Asn Gly Val Val Lys Asp Val Phe Ala Phe Gly Gly   200

Ala Val Glu Asn Pro Glu Tyr Leu Thr Pro Gln Gly Gly Ala Ala Pro Gln Pro His Pro   220
Pro Pro Ala Phe Ser Pro Ala Phe Asp Asn Leu Tyr Tyr Trp Asp Gln Asp Pro Pro Glu   240
Arg Gly Ala Pro Pro Ser Thr Phe Lys Gly Thr Pro Thr Ala Glu Asn Pro Glu Tyr Leu   260
Gly Leu Asp Val Pro Val  .      267
```

Figure 11 (SEQ ID NO: 5)

```
Gln Asn Glu Asp Leu Gly Pro Ala Ser Pro Leu Asp Ser Thr Phe Tyr Arg Ser Leu Leu    20
Glu Asp Asp Asp Met Gly Asp Leu Val Asp Ala Glu Glu Tyr Leu Val Pro Gln Gln Gly    40
Phe Phe Cys Pro Asp Pro Ala Pro Gly Ala Gly Gly Met Val His His Arg His Arg  .    60
```

Figure 12 (SEQ ID NO: 6)

| | |
|---|---|
| Met Glu Leu Ala Ala Leu Cys Arg Trp Gly Leu Leu Leu Ala Leu Leu Pro Pro Gly Ala | 20 |
| Ala Ser Thr Gln Val Cys Thr Gly Thr Asp Met Lys Leu Arg Leu Pro Ala Ser Pro Glu | 40 |
| Thr His Leu Asp Met Leu Arg His Leu Tyr Gln Gly Cys Gln Val Val Gln Gly Asn Leu | 60 |
| Glu Leu Thr Tyr Leu Pro Thr Asn Ala Ser Leu Ser Phe Leu Gln Asp Ile Gln Glu Val | 80 |
| Gln Gly Tyr Val Leu Ile Ala His Asn Gln Val Arg Gln Val Pro Leu Gln Arg Leu Arg | 100 |
| Ile Val Arg Gly Thr Gln Leu Phe Glu Asp Asn Tyr Ala Leu Ala Val Leu Asp Asn Gly | 120 |
| Asp Pro Leu Asn Asn Thr Thr Pro Val Thr Gly Ala Ser Pro Gly Gly Leu Arg Glu Leu | 140 |
| Gln Leu Arg Ser Leu Thr Glu Ile Leu Lys Gly Gly Val Leu Ile Gln Arg Asn Pro Gln | 160 |
| Leu Cys Tyr Gln Asp Thr Ile Leu Trp Lys Asp Ile Phe His Lys Asn Asn Gln Leu Ala | 180 |
| Leu Thr Leu Ile Asp Thr Asn Arg Ser Arg Ala Cys His Pro Cys Ser Pro Met Cys Lys | 200 |
| Gly Ser Arg Cys Trp Gly Glu Ser Ser Glu Asp Cys Gln Ser Leu Thr Arg Thr Val Cys | 220 |
| Ala Gly Gly Cys Ala Arg Cys Lys Gly Pro Leu Pro Thr Asp Cys Cys His Glu Gln Cys | 240 |
| Ala Ala Gly Cys Thr Gly Pro Lys His Ser Asp Cys Leu Ala Cys Leu His Phe Asn His | 260 |
| Ser Gly Ile Cys Glu Leu His Cys Pro Ala Leu Val Thr Tyr Asn Thr Asp Thr Phe Glu | 280 |
| Ser Met Pro Asn Pro Glu Gly Arg Tyr Thr Phe Gly Ala Ser Cys Val Thr Ala Cys Pro | 300 |
| Tyr Asn Tyr Leu Ser Thr Asp Val Gly Ser Cys Thr Leu Val Cys Pro Leu His Asn Gln | 320 |
| Glu Val Thr Ala Glu Asp Gly Thr Gln Arg Cys Glu Lys Cys Ser Lys Pro Cys Ala Arg | 340 |
| Val Cys Tyr Gly Leu Gly Met Glu His Leu Arg Glu Val Arg Ala Val Thr Ser Ala Asn | 360 |
| Ile Gln Glu Phe Ala Gly Cys Lys Lys Ile Phe Gly Ser Leu Ala Phe Leu Pro Glu Ser | 380 |
| Phe Asp Gly Asp Pro Ala Ser Asn Thr Ala Pro Leu Gln Pro Glu Gln Leu Gln Val Phe | 400 |
| Glu Thr Leu Glu Glu Ile Thr Gly Tyr Leu Tyr Ile Ser Ala Trp Pro Asp Ser Leu Pro | 420 |
| Asp Leu Ser Val Phe Gln Asn Leu Gln Val Ile Arg Gly Arg Ile Leu His Asn Gly Ala | 440 |
| Tyr Ser Leu Thr Leu Gln Gly Leu Gly Ile Ser Trp Leu Gly Leu Arg Ser Leu Arg Glu | 460 |
| Leu Gly Ser Gly Leu Ala Leu Ile His His Asn Thr His Leu Cys Phe Val His Thr Val | 480 |
| Pro Trp Asp Gln Leu Phe Arg Asn Pro His Gln Ala Leu Leu His Thr Ala Asn Arg Pro | 500 |
| Glu Asp Glu Cys Val Gly Glu Gly Leu Ala Cys His Gln Leu Cys Ala Arg Gly His Cys | 520 |
| Trp Gly Pro Gly Pro Thr Gln Cys Val Asn Cys Ser Gln Phe Leu Arg Gly Gln Glu Cys | 540 |
| Val Glu Glu Cys Arg Val Leu Gln Gly Leu Pro Arg Glu Tyr Val Asn Ala Arg His Cys | 560 |
| Leu Pro Cys His Pro Glu Cys Gln Pro Gln Asn Gly Ser Val Thr Cys Phe Gly Pro Glu | 580 |
| Ala Asp Gln Cys Val Ala Cys Ala His Tyr Lys Asp Pro Pro Phe Cys Val Ala Arg Cys | 600 |
| Pro Ser Gly Val Lys Pro Asp Leu Ser Tyr Met Pro Ile Trp Lys Phe Pro Asp Glu Glu | 620 |
| Gly Ala Cys Gln Pro Cys Pro Ile Asn Cys Thr His Ser Cys Val Asp Leu Asp Asp Lys | 640 |
| Gly Cys Pro Ala Glu Gln Arg Ala Ser Pro Leu Thr Ser Gln Asn Glu Asp Leu Gly Pro | 660 |
| Ala Ser Pro Leu Asp Ser Thr Phe Tyr Arg Ser Leu Leu Glu Asp Asp Asp Met Gly Asp | 680 |
| Leu Val Asp Ala Glu Glu Tyr Leu Val Pro Gln Gln Gly Phe Phe Cys Pro Asp Pro Ala | 700 |
| Pro Gly Ala Gly Gly Met Val His His Arg His Arg Ser Ser Ser Thr Arg Ser Gly Gly | 720 |
| Gly Asp Leu Thr Leu Gly Leu Glu Pro Ser Glu Glu Ala Pro Arg Ser Pro Leu Ala | 740 |
| Pro Ser Glu Gly Ala Gly Ser Asp Val Phe Asp Gly Asp Leu Gly Met Gly Ala Ala Lys | 760 |
| Gly Leu Gln Ser Leu Pro Thr His Asp Pro Ser Pro Leu Gln Arg Tyr Ser Glu Asp Pro | 780 |
| Thr Val Pro Leu Pro Ser Glu Thr Asp Gly Tyr Val Ala Pro Leu Thr Cys Ser Pro Gln | 800 |
| Pro Glu Tyr Val Asn Gln Pro Asp Val Arg Pro Gln Pro Pro Ser Pro Arg Glu Gly Pro | 820 |
| Leu Pro Ala Ala Arg Pro Ala Gly Ala Thr Leu Glu Arg Pro Lys Thr Leu Ser Pro Gly | 840 |
| Lys Asn Gly Val Val Lys Asp Val Phe Ala Phe Gly Gly Ala Val Glu Asn Pro Glu Tyr | 860 |
| Leu Thr Pro Gln Gly Gly Ala Ala Pro Gln Pro His Pro Pro Pro Ala Phe Ser Pro Ala | 880 |
| Phe Asp Asn Leu Tyr Tyr Trp Asp Gln Asp Pro Pro Glu Arg Gly Ala Pro Pro Ser Thr | 900 |
| Phe Lys Gly Thr Pro Thr Ala Glu Asn Pro Glu Tyr Leu Gly Leu Asp Val Pro Val . | 920 |

Figure 13 (SEQ ID NO: 7)

| | |
|---|---|
| Met Glu Leu Ala Ala Leu Cys Arg Trp Gly Leu Leu Leu Ala Leu Leu Pro Pro Gly Ala<br>Ala Ser Thr Gln Val Cys Thr Gly Thr Asp Met Lys Leu Arg Leu Pro Ala Ser Pro Glu<br>Thr His Leu Asp Met Leu Arg His Leu Tyr Gln Gly Cys Gln Val Val Gln Gly Asn Leu<br>Glu Leu Thr Tyr Leu Pro Thr Asn Ala Ser Leu Ser Phe Leu Gln Asp Ile Gln Glu Val<br>Gln Gly Tyr Val Leu Ile Ala His Asn Gln Val Arg Gln Val Pro Leu Gln Arg Leu Arg | 20<br>40<br>60<br>80<br>100 |
| Ile Val Arg Gly Thr Gln Leu Phe Glu Asp Asn Tyr Ala Leu Ala Val Leu Asp Asn Gly<br>Asp Pro Leu Asn Asn Thr Thr Pro Val Thr Gly Ala Ser Pro Gly Gly Leu Arg Glu Leu<br>Gln Leu Arg Ser Leu Thr Glu Ile Leu Lys Gly Gly Val Leu Ile Gln Arg Asn Pro Gln<br>Leu Cys Tyr Gln Asp Thr Ile Leu Trp Lys Asp Ile Phe His Lys Asn Asn Gln Leu Ala<br>Leu Thr Leu Ile Asp Thr Asn Arg Ser Arg Ala Cys His Pro Cys Ser Pro Met Cys Lys | 120<br>140<br>160<br>180<br>200 |
| Gly Ser Arg Cys Trp Gly Glu Ser Ser Glu Asp Cys Gln Ser Leu Thr Arg Thr Val Cys<br>Ala Gly Gly Cys Ala Arg Cys Lys Gly Pro Leu Pro Thr Asp Cys Cys His Glu Gln Cys<br>Ala Ala Gly Cys Thr Gly Pro Lys His Ser Asp Cys Leu Ala Cys Leu His Phe Asn His<br>Ser Gly Ile Cys Glu Leu His Cys Pro Ala Leu Val Thr Tyr Asn Thr Asp Thr Phe Glu<br>Ser Met Pro Asn Pro Glu Gly Arg Tyr Thr Phe Gly Ala Ser Cys Val Thr Ala Cys Pro | 220<br>240<br>260<br>280<br>300 |
| Tyr Asn Tyr Leu Ser Thr Asp Val Gly Ser Cys Thr Leu Val Cys Pro Leu His Asn Gln<br>Glu Val Thr Ala Glu Asp Gly Thr Gln Arg Cys Glu Lys Cys Ser Lys Pro Cys Ala Arg<br>Val Cys Tyr Gly Leu Gly Met Glu His Leu Arg Glu Val Arg Ala Val Thr Ser Ala Asn<br>Ile Gln Glu Phe Ala Gly Cys Lys Lys Ile Phe Gly Ser Leu Ala Phe Leu Pro Glu Ser<br>Phe Asp Gly Asp Pro Ala Ser Asn Thr Ala Pro Leu Gln Pro Glu Gln Leu Gln Val Phe | 320<br>340<br>360<br>380<br>400 |
| Glu Thr Leu Glu Glu Ile Thr Gly Tyr Leu Tyr Ile Ser Ala Trp Pro Asp Ser Leu Pro<br>Asp Leu Ser Val Phe Gln Asn Leu Gln Val Ile Arg Gly Arg Ile Leu His Asn Gly Ala<br>Tyr Ser Leu Thr Leu Gln Gly Leu Gly Ile Ser Trp Leu Gly Leu Arg Ser Leu Arg Glu<br>Leu Gly Ser Gly Leu Ala Leu Ile His His Asn Thr His Leu Cys Phe Val His Thr Val<br>Pro Trp Asp Gln Leu Phe Arg Asn Pro His Gln Ala Leu Leu His Thr Ala Asn Arg Pro | 420<br>440<br>460<br>480<br>500 |
| Glu Asp Glu Cys Val Gly Glu Gly Leu Ala Cys His Gln Leu Cys Ala Arg Gly His Cys<br>Trp Gly Pro Gly Pro Thr Gln Cys Val Asn Cys Ser Gln Phe Leu Arg Gly Gln Glu Cys<br>Val Glu Glu Cys Arg Val Leu Gln Gly Leu Pro Arg Glu Tyr Val Asn Ala Arg His Cys<br>Leu Pro Cys His Pro Glu Cys Gln Pro Gln Asn Gly Ser Val Thr Cys Phe Gly Pro Glu<br>Ala Asp Gln Cys Val Ala Cys Ala His Tyr Lys Asp Pro Pro Phe Cys Val Ala Arg Cys | 520<br>540<br>560<br>580<br>600 |
| Pro Ser Gly Val Lys Pro Asp Leu Ser Tyr Met Pro Ile Trp Lys Phe Pro Asp Glu Glu<br>Gly Ala Cys Gln Pro Cys Pro Ile Asn Cys Thr His Ser Cys Val Asp Leu Asp Asp Lys<br>Gly Cys Pro Ala Glu Gln Arg Ala Ser Pro Leu Thr Ser Gln Asn Glu Asp Leu Gly Pro<br>Ala Ser Pro Leu Asp Ser Thr Phe Tyr Arg Ser Leu Leu Glu Asp Asp Asp Met Gly Asp<br>Leu Val Asp Ala Glu Glu Tyr Leu Val Pro Gln Gln Gly Phe Phe Cys Pro Asp Pro Ala | 620<br>640<br>660<br>680<br>700 |
| Pro Gly Ala Gly Gly Met Val His His Arg His Arg . . 714 | |

Figure 14  (SEQ ID NO: 8)

| | |
|---|---|
| Met Glu Leu Ala Ala Trp Cys Arg Trp Gly Phe Leu Leu Ala Leu Leu Pro Pro Gly Ile<br>Ala Gly Thr Gln Val Cys Thr Gly Thr Asp Met Lys Leu Arg Leu Pro Ala Ser Pro Glu<br>Thr His Leu Asp Met Leu Arg His Leu Tyr Gln Gly Cys Gln Val Val Gln Gly Asn Leu<br>Glu Leu Thr Tyr Val Pro Ala Asn Ala Ser Leu Ser Phe Leu Gln Asp Ile Gln Glu Val<br>Gln Gly Tyr Met Leu Ile Ala His Asn Gln Val Lys Arg Val Pro Leu Gln Arg Leu Arg | 20<br>40<br>60<br>80<br>100 |
| Ile Val Arg Gly Thr Gln Leu Phe Glu Asp Lys Tyr Ala Leu Ala Val Leu Asp Asn Arg<br>Asp Pro Gln Asp Asn Val Ala Ala Ser Thr Pro Gly Arg Thr Pro Glu Gly Leu Arg Glu<br>Leu Gln Leu Arg Ser Leu Thr Glu Ile Leu Lys Gly Gly Val Leu Ile Arg Gly Asn Pro<br>Gln Leu Cys Tyr Gln Asp Met Val Leu Trp Lys Asp Val Phe Arg Lys Asn Asn Gln Leu<br>Ala Pro Val Asp Ile Asp Thr Asn Arg Ser Arg Ala Cys Pro Pro Cys Ala Pro Ala Cys | 120<br>140<br>160<br>180<br>200 |
| Lys Asp Asn His Cys Trp Gly Glu Ser Pro Glu Asp Cys Gln Ile Leu Thr Gly Thr Ile<br>Cys Thr Ser Gly Cys Ala Arg Cys Lys Gly Arg Leu Pro Thr Asp Cys Cys His Glu Gln<br>Cys Ala Ala Gly Cys Thr Gly Pro Lys His Ser Asp Cys Leu Ala Cys Leu His Phe Asn<br>His Ser Gly Ile Cys Glu Leu His Cys Pro Ala Leu Val Thr Tyr Asn Thr Asp Thr Phe<br>Glu Ser Met His Asn Pro Glu Gly Arg Tyr Thr Phe Gly Ala Ser Cys Val Thr Thr Cys | 220<br>240<br>260<br>280<br>300 |
| Pro Tyr Asn Tyr Leu Ser Thr Glu Val Gly Ser Cys Thr Leu Val Cys Pro Pro Asn Asn<br>Gln Glu Val Thr Ala Glu Asp Gly Thr Gln Arg Cys Glu Lys Cys Ser Lys Pro Cys Ala<br>Arg Val Cys Tyr Gly Leu Gly Met Glu His Leu Arg Gly Ala Arg Ala Ile Thr Ser Asp<br>Asn Val Gln Glu Phe Asp Gly Cys Lys Lys Ile Phe Gly Ser Leu Ala Phe Leu Pro Glu<br>Ser Phe Asp Gly Asp Pro Ser Ser Gly Ile Ala Pro Leu Arg Pro Glu Gln Leu Gln Val | 320<br>340<br>360<br>380<br>400 |
| Phe Glu Thr Leu Glu Glu Ile Thr Gly Tyr Leu Tyr Ile Ser Ala Trp Pro Asp Ser Leu<br>Arg Asp Leu Ser Val Phe Gln Asn Leu Arg Ile Ile Arg Gly Arg Ile Leu His Asp Gly<br>Ala Tyr Ser Leu Thr Leu Gln Gly Leu Gly Ile His Ser Leu Gly Leu Arg Ser Leu Arg<br>Glu Leu Gly Ser Gly Leu Ala Leu Ile His Arg Asn Ala His Leu Cys Phe Val His Thr<br>Val Pro Trp Asp Gln Leu Phe Arg Asn Pro His Gln Ala Leu Leu His Ser Gly Asn Arg | 420<br>440<br>460<br>480<br>500 |
| Pro Glu Glu Asp Cys Gly Leu Glu Gly Leu Val Cys Asn Ser Leu Cys Ala His Gly His<br>Cys Trp Gly Pro Gly Pro Thr Gln Cys Val Asn Cys Ser His Phe Leu Arg Gly Gln Glu<br>Cys Val Glu Glu Cys Arg Val Trp Lys Gly Leu Pro Arg Glu Tyr Val Ser Asp Lys Arg<br>Cys Leu Pro Cys His Pro Glu Cys Gln Pro Gln Asn Ser Ser Glu Thr Cys Phe Gly Ser<br>Glu Ala Asp Gln Cys Ala Ala Cys Ala His Tyr Lys Asp Ser Ser Ser Cys Val Ala Arg | 520<br>540<br>560<br>580<br>600 |
| Cys Pro Ser Gly Val Lys Pro Asp Leu Ser Tyr Met Pro Ile Trp Lys Tyr Pro Asp Glu<br>Glu Gly Ile Cys Gln Pro Cys Pro Ile Asn Cys Thr His Ser Cys Val Asp Leu Asp Glu<br>Arg Gly Cys Pro Ala Glu Gln Arg Ala Ser Pro Val Thr Phe     654 | 620<br>640 |

FIGURE 15a (SEQ ID NO:9)

```
atg gag ctg gcg gcc ttg tgc cgc tgg ggg ctc ctc ctc gcc ctc ttg      48
Met Glu Leu Ala Ala Leu Cys Arg Trp Gly Leu Leu Leu Ala Leu Leu
1               5                   10                  15 ccc ccc gga gcc gcg agc acc caa gtg tgc acc ggc aca gac atg aag      96
Pro Pro Gly Ala Ala Ser Thr Gln Val Cys Thr Gly Thr Asp Met Lys
            20                  25                  30 ctg cgg ctc cct gcc agt ccc gag acc cac ctg gac atg ctc cgc cac      144
Leu Arg Leu Pro Ala Ser Pro Glu Thr His Leu Asp Met Leu Arg His
        35                  40                  45 ctc tac cag ggc tgc cag gtg gtg cag gga aac ctg gaa ctc acc tac      192
Leu Tyr Gln Gly Cys Gln Val Val Gln Gly Asn Leu Glu Leu Thr Tyr
    50                  55                  60 ctg ccc acc aat gcc agc ctg tcc ttc ctg cag gat atc cag gag gtg      240
Leu Pro Thr Asn Ala Ser Leu Ser Phe Leu Gln Asp Ile Gln Glu Val
65                  70                  75                  80 cag ggc tac gtg ctc atc gct cac aac caa gtg agg cag gtc cca ctg      288
Gln Gly Tyr Val Leu Ile Ala His Asn Gln Val Arg Gln Val Pro Leu
                85                  90                  95 cag agg ctg cgg att gtg cga ggc acc cag ctc ttt gag gac aac tat      336
Gln Arg Leu Arg Ile Val Arg Gly Thr Gln Leu Phe Glu Asp Asn Tyr
            100                 105                 110 gcc ctg gcc gtg cta gac aat gga gac ccg ctg aac aat acc acc cct      384
Ala Leu Ala Val Leu Asp Asn Gly Asp Pro Leu Asn Asn Thr Thr Pro
        115                 120                 125 gtc aca ggg gcc tcc cca gga ggc ctg cgg gag ctg cag ctt cga agc      432
Val Thr Gly Ala Ser Pro Gly Gly Leu Arg Glu Leu Gln Leu Arg Ser
    130                 135                 140 ctc aca gag atc ttg aaa gga ggg gtc ttg atc cag cgg aac ccc cag      480
Leu Thr Glu Ile Leu Lys Gly Gly Val Leu Ile Gln Arg Asn Pro Gln
145                 150                 155                 160 ctc tgc tac cag gac acg att ttg tgg aag gac atc ttc cac aag aac      528
Leu Cys Tyr Gln Asp Thr Ile Leu Trp Lys Asp Ile Phe His Lys Asn
                165                 170                 175 aac cag ctg gct ctc aca ctg ata gac acc aac cgc tct cgg gcc tgc      576
Asn Gln Leu Ala Leu Thr Leu Ile Asp Thr Asn Arg Ser Arg Ala Cys
            180                 185                 190 cac ccc tgt tct ccg atg tgt aag ggc tcc cgc tgc tgg gga gag agt      624
His Pro Cys Ser Pro Met Cys Lys Gly Ser Arg Cys Trp Gly Glu Ser
        195                 200                 205
```

Figure 15b (SEQ ID NO: 9)

```
tct gag gat tgt cag agc ctg acg cgc act gtc tgt gcc ggt ggc tgt            672
Ser Glu Asp Cys Gln Ser Leu Thr Arg Thr Val Cys Ala Gly Gly Cys
    210                 215                 220 gcc cgc tgc aag ggg cca ctg ccc act gac tgc tgc cat gag cag tgt            720
Ala Arg Cys Lys Gly Pro Leu Pro Thr Asp Cys Cys His Glu Gln Cys
225                 230                 235                 240 gct gcc ggc tgc acg ggc ccc aag cac tct gac tgc ctg gcc tgc ctc            768
Ala Ala Gly Cys Thr Gly Pro Lys His Ser Asp Cys Leu Ala Cys Leu
                245                 250                 255 cac ttc aac cac agt ggc atc tgt gag ctg cac tgc cca gcc ctg gtc            816
His Phe Asn His Ser Gly Ile Cys Glu Leu His Cys Pro Ala Leu Val
            260                 265                 270 acc tac aac aca gac acg ttt gag tcc atg ccc aat ccc gag ggc cgg            864
Thr Tyr Asn Thr Asp Thr Phe Glu Ser Met Pro Asn Pro Glu Gly Arg
        275                 280                 285 tat aca ttc ggc gcc agc tgt gtg act gcc tgt ccc tac aac tac ctt            912
Tyr Thr Phe Gly Ala Ser Cys Val Thr Ala Cys Pro Tyr Asn Tyr Leu
    290                 295                 300 tct acg gac gtg gga tcc tgc acc ctc gtc tgc ccc ctg cac aac caa            960
Ser Thr Asp Val Gly Ser Cys Thr Leu Val Cys Pro Leu His Asn Gln
305                 310                 315                 320 gag gtg aca gca gag gat gga aca cag cgg tgt gag aag tgc agc aag           1008
Glu Val Thr Ala Glu Asp Gly Thr Gln Arg Cys Glu Lys Cys Ser Lys
                325                 330                 335 ccc tgt gcc cga gtg tgc tat ggt ctg ggc atg gag cac ttg cga gag           1056
Pro Cys Ala Arg Val Cys Tyr Gly Leu Gly Met Glu His Leu Arg Glu
            340                 345                 350 gtg agg gca gtt acc agt gcc aat atc cag gag ttt gct ggc tgc aag           1104
Val Arg Ala Val Thr Ser Ala Asn Ile Gln Glu Phe Ala Gly Cys Lys
        355                 360                 365 aag atc ttt ggg agc ctg gca ttt ctg ccg gag agc ttt gat ggg gac           1152
Lys Ile Phe Gly Ser Leu Ala Phe Leu Pro Glu Ser Phe Asp Gly Asp
    370                 375                 380 cca gcc tcc aac act gcc ccg ctc cag cca gag cag ctc caa gtg ttt           1200
Pro Ala Ser Asn Thr Ala Pro Leu Gln Pro Glu Gln Leu Gln Val Phe
385                 390                 395                 400 gag act ctg gaa gag atc aca ggt tac cta tac atc tca gca tgg ccg           1248
Glu Thr Leu Glu Glu Ile Thr Gly Tyr Leu Tyr Ile Ser Ala Trp Pro
                405                 410                 415
```

Figure 15c (SEQ ID NO: 9)

```
gac agc ctg cct gac ctc agc gtc ttc cag aac ctg caa gta atc cgg      1296
Asp Ser Leu Pro Asp Leu Ser Val Phe Gln Asn Leu Gln Val Ile Arg
        420                 425                 430 gga cga att ctg cac aat ggc gcc tac tcg ctg acc ctg caa ggg ctg      1344
Gly Arg Ile Leu His Asn Gly Ala Tyr Ser Leu Thr Leu Gln Gly Leu
        435                 440                 445 ggc atc agc tgg ctg ggg ctg cgc tca ctg agg gaa ctg ggc agt gga      1392
Gly Ile Ser Trp Leu Gly Leu Arg Ser Leu Arg Glu Leu Gly Ser Gly
        450                 455                 460 ctg gcc ctc atc cac cat aac acc cac ctc tgc ttc gtg cac acg gtg      1440
Leu Ala Leu Ile His His Asn Thr His Leu Cys Phe Val His Thr Val
465                 470                 475                 480 ccc tgg gac cag ctc ttt cgg aac ccg cac caa gct ctg ctc cac act      1488
Pro Trp Asp Gln Leu Phe Arg Asn Pro His Gln Ala Leu Leu His Thr
                485                 490                 495 gcc aac cgg cca gag gac gag tgt gtg ggc gag ggc ctg gcc tgc cac      1536
Ala Asn Arg Pro Glu Asp Glu Cys Val Gly Glu Gly Leu Ala Cys His
                500                 505                 510 cag ctg tgc gcc cga ggg cac tgc tgg ggt cca ggg ccc acc cag tgt      1584
Gln Leu Cys Ala Arg Gly His Cys Trp Gly Pro Gly Pro Thr Gln Cys
        515                 520                 525 gtc aac tgc agc cag ttc ctt cgg ggc cag gag tgc gtg gag gaa tgc      1632
Val Asn Cys Ser Gln Phe Leu Arg Gly Gln Glu Cys Val Glu Glu Cys
        530                 535                 540 cga gta ctg cag ggg ctc ccc agg gag tat gtg aat gcc agg cac tgt      1680
Arg Val Leu Gln Gly Leu Pro Arg Glu Tyr Val Asn Ala Arg His Cys
545                 550                 555                 560 ttg ccg tgc cac cct gag tgt cag ccc cag aat ggc tca gtg acc tgt      1728
Leu Pro Cys His Pro Glu Cys Gln Pro Gln Asn Gly Ser Val Thr Cys
                565                 570                 575 ttt gga ccg gag gct gac cag tgt gtg gcc tgt gcc cac tat aag gac      1776
Phe Gly Pro Glu Ala Asp Gln Cys Val Ala Cys Ala His Tyr Lys Asp
                580                 585                 590 cct ccc ttc tgc gtg gcc cgc tgc ccc agc ggt gtg aaa cct gac ctc      1824
Pro Pro Phe Cys Val Ala Arg Cys Pro Ser Gly Val Lys Pro Asp Leu
        595                 600                 605 tcc tac atg ccc atc tgg aag ttt cca gat gag gag ggc gca tgc cag      1872
Ser Tyr Met Pro Ile Trp Lys Phe Pro Asp Glu Glu Gly Ala Cys Gln
        610                 615                 620
```

Figure 15d (SEQ ID NO: 9)

```
cct tgc ccc atc aac tgc acc cac tcc tgt gtg gac ctg gat gac aag     1920
Pro Cys Pro Ile Asn Cys Thr His Ser Cys Val Asp Leu Asp Asp Lys
625                 630                 635                 640 ggc tgc ccc gcc gag cag aga gcc agc cct ctg acg tcc atc atc tct     1968
Gly Cys Pro Ala Glu Gln Arg Ala Ser Pro Leu Thr Ser Ile Ile Ser
                645                 650                 655 gcg gtg gtt ggc att ctg ctg gtc gtg gtc ttg ggg gtg gtc ttt ggg     2016
Ala Val Val Gly Ile Leu Leu Val Val Val Leu Gly Val Val Phe Gly
                660                 665                 670 atc ctc atc aag cga cgg cag cag aag atc cgg aag tac acg atg cgg     2064
Ile Leu Ile Lys Arg Arg Gln Gln Lys Ile Arg Lys Tyr Thr Met Arg
            675                 680                 685 aga ctg ctg cag gaa acg gag ctg gtg gag ccg ctg aca cct agc gga     2112
Arg Leu Leu Gln Glu Thr Glu Leu Val Glu Pro Leu Thr Pro Ser Gly
    690                 695                 700 gcg atg ccc aac cag gcg cag atg cgg atc ctg aaa gag acg gag ctg     2160
Ala Met Pro Asn Gln Ala Gln Met Arg Ile Leu Lys Glu Thr Glu Leu
705                 710                 715                 720 agg aag gtg aag gtg ctt gga tct ggc gct ttt ggc aca gtc tac aag     2208
Arg Lys Val Lys Val Leu Gly Ser Gly Ala Phe Gly Thr Val Tyr Lys
                725                 730                 735 ggc atc tgg atc cct gat ggg gag aat gtg aaa att cca gtg gcc atc     2256
Gly Ile Trp Ile Pro Asp Gly Glu Asn Val Lys Ile Pro Val Ala Ile
                740                 745                 750 aaa gtg ttg agg gaa aac aca tcc ccc aaa gcc aac aaa gaa atc tta     2304
Lys Val Leu Arg Glu Asn Thr Ser Pro Lys Ala Asn Lys Glu Ile Leu
            755                 760                 765 gac gaa gca tac gtg atg gct ggt gtg ggc tcc cca tat gtc tcc cgc     2352
Asp Glu Ala Tyr Val Met Ala Gly Val Gly Ser Pro Tyr Val Ser Arg
    770                 775                 780 ctt ctg ggc atc tgc ctg aca tcc acg gtg cag ctg gtg aca cag ctt     2400
Leu Leu Gly Ile Cys Leu Thr Ser Thr Val Gln Leu Val Thr Gln Leu
785                 790                 795                 800 atg ccc tat ggc tgc ctc tta gac cat gtc cgg gaa aac cgc gga cgc     2448
Met Pro Tyr Gly Cys Leu Leu Asp His Val Arg Glu Asn Arg Gly Arg
                805                 810                 815 ctg ggc tcc cag gac ctg ctg aac tgg tgt atg cag att gcc aag ggg     2496
Leu Gly Ser Gln Asp Leu Leu Asn Trp Cys Met Gln Ile Ala Lys Gly
                820                 825                 830
```

Figure 15e (SEQ ID NO: 9)

```
atg agc tac ctg gag gat gtg cgg ctc gta cac agg gac ttg gcc gct        2544
Met Ser Tyr Leu Glu Asp Val Arg Leu Val His Arg Asp Leu Ala Ala
        835                 840                 845 cgg aac gtg ctg gtc aag agt ccc aac cat gtc aaa att aca gac ttc        2592
Arg Asn Val Leu Val Lys Ser Pro Asn His Val Lys Ile Thr Asp Phe
    850                 855                 860 ggg ctg gct cgg ctg ctg gac att gac gag aca gag tac cat gca gat        2640
Gly Leu Ala Arg Leu Leu Asp Ile Asp Glu Thr Glu Tyr His Ala Asp
865                 870                 875                 880 ggg ggc aag gtg ccc atc aag tgg atg gcg ctg gag tcc att ctc cgc        2688
Gly Gly Lys Val Pro Ile Lys Trp Met Ala Leu Glu Ser Ile Leu Arg
                885                 890                 895 cgg cgg ttc acc cac cag agt gat gtg tgg agt tat ggt gtg act gtg        2736
Arg Arg Phe Thr His Gln Ser Asp Val Trp Ser Tyr Gly Val Thr Val
            900                 905                 910 tgg gag ctg atg act ttt ggg gcc aaa cct tac gat ggg atc cca gcc        2784
Trp Glu Leu Met Thr Phe Gly Ala Lys Pro Tyr Asp Gly Ile Pro Ala
        915                 920                 925 cgg gag atc cct gac ctg ctg gaa aag ggg gag cgg ctg ccc cag ccc        2832
Arg Glu Ile Pro Asp Leu Leu Glu Lys Gly Glu Arg Leu Pro Gln Pro
    930                 935                 940 ccc atc tgc acc att gat gtc tac atg atc atg gtc aaa tgt tgg atg        2880
Pro Ile Cys Thr Ile Asp Val Tyr Met Ile Met Val Lys Cys Trp Met
945                 950                 955                 960 att gac tct gaa tgt cgg cca aga ttc cgg gag ttg gtg tct gaa ttc        2928
Ile Asp Ser Glu Cys Arg Pro Arg Phe Arg Glu Leu Val Ser Glu Phe
                965                 970                 975 tcc cgc atg gcc agg gac ccc cag cgc ttt gtg gtc atc cag aat gag        2976
Ser Arg Met Ala Arg Asp Pro Gln Arg Phe Val Val Ile Gln Asn Glu
            980                 985                 990 gac ttg ggc cca gcc agt ccc ttg  gac agc acc ttc tac  cgc tca ctg      3024
Asp Leu Gly Pro Ala Ser Pro Leu  Asp Ser Thr Phe Tyr  Arg Ser Leu
        995                 1000                 1005 ctg gag    gac gat gac atg ggg    gac ctg gtg gat gct    gag gag tat   3069
Leu Glu    Asp Asp Asp Met Gly    Asp Leu Val Asp Ala    Glu Glu Tyr
    1010                 1015                     1020 ctg gta    ccc cag cag ggc ttc    ttc tgt cca gac cct    gcc ccg ggc   3114
Leu Val    Pro Gln Gln Gly Phe    Phe Cys Pro Asp Pro    Ala Pro Gly
    1025                 1030                     1035
```

Figure 15f (SEQ ID NO: 9)

```
gct ggg ggc atg gtc cac cac agg cac cgc agc tca tct acc agg          3159
Ala Gly Gly Met Val His His Arg His Arg Ser Ser Ser Thr Arg
    1040                1045                1050 agt ggc ggt ggg gac ctg aca cta ggg ctg gag ccc tct gaa gag          3204
Ser Gly Gly Gly Asp Leu Thr Leu Gly Leu Glu Pro Ser Glu Glu
    1055                1060                1065 gag gcc ccc agg tct cca ctg gca ccc tcc gaa ggg gct ggc tcc          3249
Glu Ala Pro Arg Ser Pro Leu Ala Pro Ser Glu Gly Ala Gly Ser
    1070                1075                1080 gat gta ttt gat ggt gac ctg gga atg ggg gca gcc aag ggg ctg          3294
Asp Val Phe Asp Gly Asp Leu Gly Met Gly Ala Ala Lys Gly Leu
    1085                1090                1095 caa agc ctc ccc aca cat gac ccc agc cct cta cag cgg tac agt          3339
Gln Ser Leu Pro Thr His Asp Pro Ser Pro Leu Gln Arg Tyr Ser
    1100                1105                1110 gag gac ccc aca gta ccc ctg ccc tct gag act gat ggc tac gtt          3384
Glu Asp Pro Thr Val Pro Leu Pro Ser Glu Thr Asp Gly Tyr Val
    1115                1120                1125 gcc ccc ctg acc tgc agc ccc cag cct gaa tat gtg aac cag cca          3429
Ala Pro Leu Thr Cys Ser Pro Gln Pro Glu Tyr Val Asn Gln Pro
    1130                1135                1140 gat gtt cgg ccc cag ccc cct tcg ccc cga gag ggc cct ctg cct          3474
Asp Val Arg Pro Gln Pro Pro Ser Pro Arg Glu Gly Pro Leu Pro
    1145                1150                1155 gct gcc cga cct gct ggt gcc act ctg gaa agg ccc aag act ctc          3519
Ala Ala Arg Pro Ala Gly Ala Thr Leu Glu Arg Pro Lys Thr Leu
    1160                1165                1170 tcc cca ggg aag aat ggg gtc gtc aaa gac gtt ttt gcc ttt ggg          3564
Ser Pro Gly Lys Asn Gly Val Val Lys Asp Val Phe Ala Phe Gly
    1175                1180                1185 ggt gcc gtg gag aac ccc gag tac ttg aca ccc cag gga gga gct          3609
Gly Ala Val Glu Asn Pro Glu Tyr Leu Thr Pro Gln Gly Gly Ala
    1190                1195                1200 gcc cct cag ccc cac cct cct cct gcc ttc agc cca gcc ttc gac          3654
Ala Pro Gln Pro His Pro Pro Pro Ala Phe Ser Pro Ala Phe Asp
    1205                1210                1215 aac ctc tat tac tgg gac cag gac cca cca gag cgg ggg gct cca          3699
Asn Leu Tyr Tyr Trp Asp Gln Asp Pro Pro Glu Arg Gly Ala Pro
    1220                1225                1230
```

Figure 15g (SEQ ID NO: 9)

```
ccc agc acc ttc aaa ggg aca  cct acg gca gag aac  cca gag tac      3744
Pro Ser Thr Phe Lys Gly Thr  Pro Thr Ala Glu Asn  Pro Glu Tyr
    1235            1240                 1245 ctg ggt ctg gac gtg cca gtg  tga                                    3768
Leu Gly Leu Asp Val Pro Val
    1250            1255
```

FIGURE 16a (SEQ ID NO: 10)

```
   1 ccgggccgga gccgcaatga tcatcatgga gctggcggcc tggtgccgct ggggggttcct
  61 cctcgccctc ctgcccccg  gaatcgcggg cacccaagtg tgtaccggca cagacatgaa
 121 gttgcggctc cctgccagtc ctgagaccca cctggacatg ctccgccacc tgtaccaggg
 181 ctgtcaggta gtgcagggca acttggagct tacctacgtg cctgccaatg ccagcctctc
 241 attcctgcag gacatccagg aagttcaggg ttacatgctc atcgctcaca accaggtgaa
 301 gcgcgtccca ctgcaaaggc tgcgcatcgt gagagggacc cagctctttg aggacaagta
 361 tgccctggct gtgctagaca accgagatcc tcaggacaat gtcgccgcct ccaccccagg
 421 cagaacccca gagggctgc  gggagctgca gcttcgaagt ctcacagaga tcctgaaggg
 481 aggagttttg atccgtggga accctcagct ctgctaccag acatggtttt gtggaagga
 541 cgtcttccgc aagaataacc aactggctcc tgtcgatata gacaccaatc gttcccgggc
 601 ctgtccacct tgtgcccccg cctgcaaaga caatcactgt tggggtgaga gtccggaaga
 661 ctgtcagatc ttgactggca ccatctgtac cagtggttgt gcccggtgca agggccggct
 721 gcccactgac tgctgccatg agcagtgtgc cgcaggctgc acgggcccca agcattctga
 781 ctgcctggcc tgcctccact tcaatcatag tggtatctgt gagctgcact gcccagccct
 841 cgtcacctac aacacagaca cctttgagtc catgcacaac cctgagggtc gctacacctt
 901 tggtgccagc tgcgtgacca cctgcccta  caactacctg tctacggaag tgggatcctg
 961 cactctggtg tgtccccga  ataaccaaga ggtcacagct gaggacggaa cacagcgttg
1021 tgagaaatgc agcaagccct gtgctcgagt gtgctatggt ctgggcatgg agcaccttcg
1081 aggggcgagg gccatcacca gtgacaatgt ccaggagttt gatggctgca agaagatctt
1141 tgggagcctg gcattttgc  cggagagctt gatggggac  ccctcctccg gcattgctcc
1201 gctgaggcct gagcagctcc aagtgttcga accctggag  gagatcacag gttacctgta
1261 catctcagca tggccagaca gtctccgtga cctcagtgtc ttccagaacc ttcgaatcat
1321 tcggggacgg attctccacg atggcgcgta ctcattgaca ctgcaaggcc tggggatcca
1381 ctcgctgggg ctgcgctcac tgcgggagct gggcagtgga ttggctctga ttcaccgcaa
1441 cgcccatctc tgctttgtac acactgtacc ttgggaccag ctcttccgga acccacatca
1501 ggccctgctc cacagtggga accggccgga agaggacttg tgcgtctcga gcggcttggt
1561 ctgtaactca ctgtgtgccc acgggcactg ctggggccca gggcccaccc agtgtgtcaa
1621 ctgcagtcat ttccttcggg gccaggagtg tgtggaggag tgccgagtat ggaagggggct
1681 ccccgggag  tatgtgagtg acaagcgctg tctgccgtgt caccccgagt gtcagcctca
1741 aaacagctca gagacctgct ttggatcgga ggctgatcag tgtgcagcct gcgcccacta
1801 caaggactcg tcctcctgtg tggctcgctg cccagtggt  gtgaaaccgg acctctccta
1861 catgcccatc tggaagtacc cggatgagga gggcatatgc agccgtgcc  ccatcaactg
1921 cacccactcc tgtgtggatc tggatgaacg aggctgccca gcagagcaga gagccagccc
1981 ggtgacattc atcattgcaa ctgtagaggg cgtcctgctg ttcctgatct tagtggtggt
2041 cgttggaatc ctaatcaaac gaaggagaca gaagatccgg aagtatacga tgcgtaggct
2101 gctgcaggaa actgagttag tggagccgct gacgcccagc ggagcaatgc ccaaccaggc
2161 tcagatgcgg atcctaaaag agacggagct aaggaaggtg aaggtgcttg gatcaggagc
2221 ttttggcact gtctacaagg gcatctggat cccagatggg gagaatgtga aatccccgt
2281 ggctatcaag gtgttgagag aaaacacatc tcctaaagcc aacaaagaaa ttctagatga
2341 agcgtatgtg atggctggtg tgggttctcc gtatgtgtcc cgcctcctgg catctgcct
2401 gacatccaca gtacagctgg tgacacagct tatgcctac  ggctgccttc tggaccatgt
2461 ccgagaacac cgaggtcgcc taggctccca ggacctgctc aactggtgtg ttcagattgc
2521 caaggggatg agctacctgg aggacgtgcg gcttgtacac agggacctgg ctgcccggaa
2581 tgtgctagtc aagagtccca accacgtcaa gattacagat ttcggctggc tcggctgct
2641 ggacattgat gagacagagt accatgcaga tgggggcaag gtgcccatca aatggatggc
2701 attggaatct attctcagac gccggttcac ccatcagagt gatgtgtgga gctatggagt
2761 gactgtgtgg gagctgatga cttttgggc  caaaccttac gatggaatcc cagcccggga
2821 gatccctgat ttgctggaga gggagaacg  cctacctcag cctccaatct gcaccattga
2881 tgtctacatg attatggtca atgttggat  gattgactct gaatgtcgcc cgagattccg
2941 ggagttggtg tcagaatttt cacgtatggc gagggacccc cagcgttttg tggtcatcca
3001 gaacgaggac ttgggcccat ccagcccat  ggacagtacc ttctaccgtt cactgctgga
3061 agatgatgac atgggtgacc tggtagacgc tgaagagtat ctggtgcccc agcagggatt
3121 cttctccccg gacccaccc  caggcactgg gagcacagcc catagaaggc accgcagctc
3181 gtccaccagg agtggaggtg gtgagctgac actgggcctg gagccctcgg aagaagggcc
3241 ccccagatct ccactggctc cctcggaagg ggctggctcc gatgtgtttg atggtgacct
3301 ggcaatgggg gtaaccaaag ggctgcagag cctctctcca catgacctca gccctctaca
```

FIGURE 16b (SEQ ID NO: 10)

```
3361 gcggtacagc gaggacccca cattacctct gccccccgag actgatggct atgttgctcc
3421 cctggcctgc agcccccagc ccgagtatgt gaaccaatca gaggttcagc ctcagcctcc
3481 tttaacccca gagggtcctc tgcctcctgt ccggcctgct ggtgctactc tagaaagacc
3541 caagactctc tctcctggga agaatggggt tgtcaaagac gttttttgcct tcgggggtgc
3601 tgtggagaac cctgaatact tagtaccgag agaaggcact gcctctccgc cccacccttc
3661 tcctgccttc agcccagcct ttgacaacct ctattactgg gaccagaact catcggagca
3721 ggggcctcca ccaagtaact ttgaagggac ccccactgca gagaaccctg agtacctagg
3781 cctggatgta cctgtatgag acgtgtgcag acgtcctgtg ctttcagagt ggggaaggcc
3841 tgacttgtgg tctccatcgc cacaaagcag ggagagggtc ctctggccac attacatcca
3901 gggcagacgg ctctaccagg aacctgcccc gaggaacctt tccttgctgc ttgaa
```

FIGURE 19a (SEQ ID NO:11)

```
atggagctgg cggcctggtg ccgttggggg ttcctcctcg ccctcctgtc ccccggagcc      60
gcgggtaccc aagtgtgtac cggtaccgac atgaagttgc gactccctgc cagtcctgag     120
acccacctgg acatgcttcg ccacctctac cagggctgtc aggtggtgca gggcaatttg     180
gagcttacct acctgcccgc caatgccagc ctctcattcc tgcaggacat ccaggaagtc     240
cagggataca tgctcatcgc tcacaaccga gtgaaacacg tcccactgca gaggttgcgc     300
atcgtgagag ggactcagct ctttgaggac aagtatgccc tggctgtgct agacaaccga     360
gacccttgg acaacgtcac caccgccgcc ccaggcagaa ccccagaagg gctgcgggag      420
ctgcagcttc gaagtctcac agagatcttg aagggaggag ttttgatccg tgggaaccct     480
cagctctgct accaggacat ggttttgtgg aaggatgtcc tccgtaagaa taaccagctg     540
gctcctgtcg acatggacac caatcgttcc cgggcctgtc caccttgtgc cccaacctgc     600
aaagacaatc actgttgggg tgagagtcct gaagactgtc agatcttgac tggcaccatc     660
tgtactagtg gctgtgcccg gtgcaagggc cggctgccca ctgactgttg ccatgagcag     720
tgtgctgcag gctgcacggg tcccaagcat tctgactgcc tggcctgcct ccacttcaat     780
catagtggta tctgtgagct gcactgcccg gccctcatca cctacaacac agacaccttc     840
gagtccatgc tcaaccctga gggtcgctac acctttggtg ccagctgtgt gacccctgc      900
ccctacaact acctctccac ggaagtggga tcctgcactc tggtctgtcc cccgaacaac     960
caagaggtca cagctgagga cggaacacag cggtgtgaga aatgcagcaa gccctgtgct    1020
ggagtatgct atggtctggg catggagcac ctccgagggg cgagggccat caccagtgac    1080
aatatccagg agtttgctgg ctgcaagaag atctttggga cctggcatt tttgccggag     1140
agctttgatg ggaacccctc ctccggcgtt gccccactga agccagagca tctccaagtg    1200
ttcgaaaccc tggaggagat cacaggttac ctatacattt cagcatggcc agagagcttc    1260
caagacctca gtgtcttcca gaaccttcgg gtcattcggg acggattct ccatgatggt      1320
gcttactcat tgacgttgca aggcctgggg attcactcac tggggctacg ctcactgcgg    1380
gagctgggca gtggattggc tctcattcac cgcaacaccc atctctgctt tgtaaacact    1440
gtaccttggg accagctctt ccggaacccg caccaggccc tactccacag tgggaaccgg    1500
ccagaagagg catgtggtct tgagggcttg gtctgtaact cactgtgtgc ccgtgggcac    1560
tgctgggggc cagggcccac ccagtgtgtc aactgcagtc agttcctccg gggccaggag    1620
tgtgtggagg agtgccgagt atggaagggg ctccccaggg agtatgtgag gggcaagcac    1680
tgtctgccat gccaccccga gtgtcagcct caaaacagct cggagacctg ctatggatcg    1740
gaggctgacc agtgtgaggc ttgtgcccac tacaaggact catcttcctg tgtggctcgc    1800
tgccccagtg gtgtgaagcc agacctctcc tacatgccta tctggaagta cccggatgag    1860
gagggcatat gtcagccatg ccccatcaac tgcacccact catgtgtgga cctggacgaa    1920
cgaggctgcc cagcagagca gagagccagc ccagtgacat catcattgc aactgtggtg     1980
ggcgtcctgt tgttcctgat catagtggtg gtcattggaa tcctaatcaa acgaaggcga    2040
cagaagatcc ggaagtatac catgcgtagg ctgctgcagg agaccgagct ggtggagccg    2100
ctgacgccca gtggagctgt gcccaaccag gctcagatgc ggatcctaaa ggagacagag    2160
ctaaggaagc tgaaggtgct tgggtcagga gccttcggca ctgtctacaa gggcatctgg    2220
atcccagatg gggagaacgt gaaaatcccc gtggccatca aggtgttgag ggaaaacaca    2280
tctcctaaag ctaacaaaga atcctagat gaagcgtacg tcatggctgg tgtgggttct     2340
ccatatgtgt cccgcctcct gggcatctgc ctgacatcca cagtgcagct ggtgacacag    2400
cttatgccct atggctgcct tctggaccat gtccgagaac accgaggtcg cttaggctcc    2460
caggacctgc tcaactggtg tgttcagatt gccaagggga tgagctacct ggaggaagtt    2520
cggcttgttc acagggacct agctgcccga acgtgctagt caagagtcc aaccacgtc      2580
aagattaccg acttcgggct ggcacggctg ctggacattg atgagactga ataccatgca    2640
gatgggggca aggtgcccat caagtggatg gcattggaat ctattctcag acgccggttc    2700
actcatcaga gtgatgtgtg gagctatggt gtgactgtgt gggagctgat gacctttggg    2760
gccaaacctt acgatgggat cccagctcgg gagatccctg atttgctgga agggagaa      2820
cgcctacctc agcctccaat ctgcaccatc gacgtctaca tgatcatggt caaatgttgg    2880
atgattgact ccgaatgtcg cccgagattc cgggagttgg tatcagaatt ctcccgtatg    2940
gcaagggacc cccagcgctt tgtggtcatc cagaacgagg acttaggccc ctccagcccc    3000
atggacagca ccttctaccg ttcactgctg gaggatgatg acatggggga gctggtcgat    3060
gctgaagagt acctggtacc ccagcaggga ttcttctccc cagaccctgc cctaggtact    3120
gggagcacag cccaccgcag acaccgcagc tcgtcggcca ggagtggcgg tggtgagctg    3180
acactgggcc tggagccctc ggaagaagag ccccccagat ctccactggc tccctccgaa    3240
gggctggct ccgatgtgtt tgatggtgac ctggcagtgg gggtaaccaa aggactgcag      3300
agcctctctc cacatgacct cagccctcta cagcggtaca gtgaggatcc cacattacct    3360
```

FIGURE 19b (SEQ ID NO:11)

```
ctgcccccccg agactgatgg ctacgttgct cccctggcct gcagccccca gcccgagtat    3420
gtgaaccagc cagaggttcg gcctcagtct cccttgaccc cagagggtcc tccgcctccc    3480
atccgacctg ctggtgctac tctagaaaga cccaagactc tctctcctgg gaaaaatggg    3540
gttgtcaaag acgtttttgc ctttgggggt gctgtggaga accctgaata cctagcaccc    3600
agagcaggca ctgcctctca gccccaccct tctcctgcct tcagcccagc ctttgacaac    3660
ctctattact gggaccagaa ctcatcggag cagggtcctc caccaagtac ctttgaaggg    3720
accccactg cagagaaccc tgagtaccta ggcctggatg tgccagtatg a             3771
```

Figure 20a (SEQ ID NO:14)

```
Met Glu Leu Ala Ala Trp Cys Arg Trp Gly Phe Leu Leu Ala Leu Leu
 1               5                  10                      15
Ser Pro Gly Ala Ala Gly Thr Gln Val Cys Thr Gly Thr Asp Met Lys
             20                  25                  30
Leu Arg Leu Pro Ala Ser Pro Glu Thr His Leu Asp Met Leu Arg His
             35                  40                  45
Leu Tyr Gln Gly Cys Gln Val Val Gln Gly Asn Leu Glu Leu Thr Tyr
     50                  55                  60
Leu Pro Ala Asn Ala Ser Leu Ser Phe Leu Gln Asp Ile Gln Glu Val
65                   70                  75                   80
Gln Gly Tyr Met Leu Ile Ala His Asn Arg Val Lys His Val Pro Leu
                 85                  90                  95
Gln Arg Leu Arg Ile Val Arg Gly Thr Gln Leu Phe Glu Asp Lys Tyr
             100                 105                 110
Ala Leu Ala Val Leu Asp Asn Arg Asp Pro Leu Asp Asn Val Thr Thr
             115                 120                 125
Ala Ala Pro Gly Arg Thr Pro Glu Gly Leu Arg Glu Leu Gln Leu Arg
    130                 135                 140
Ser Leu Thr Glu Ile Leu Lys Gly Gly Val Leu Ile Arg Gly Asn Pro
145                 150                 155                 160
Gln Leu Cys Tyr Gln Asp Met Val Leu Trp Lys Asp Val Leu Arg Lys
                165                 170                 175
Asn Asn Gln Leu Ala Pro Val Asp Met Asp Thr Asn Arg Ser Arg Ala
             180                 185                 190
Cys Pro Pro Cys Ala Pro Thr Cys Lys Asp Asn His Cys Trp Gly Glu
         195                 200                 205
Ser Pro Glu Asp Cys Gln Ile Leu Thr Gly Thr Ile Cys Thr Ser Gly
    210                 215                 220
Cys Ala Arg Cys Lys Gly Arg Leu Pro Thr Asp Cys Cys His Glu Gln
225                 230                 235                 240
Cys Ala Ala Gly Cys Thr Gly Pro Lys His Ser Asp Cys Leu Ala Cys
                245                 250                 255
Leu His Phe Asn His Ser Gly Ile Cys Glu Leu His Cys Pro Ala Leu
             260                 265                 270
Ile Thr Tyr Asn Thr Asp Thr Phe Glu Ser Met Leu Asn Pro Glu Gly
         275                 280                 285
Arg Tyr Thr Phe Gly Ala Ser Cys Val Thr Thr Cys Pro Tyr Asn Tyr
    290                 295                 300
Leu Ser Thr Glu Val Gly Ser Cys Thr Leu Val Cys Pro Pro Asn Asn
305                 310                 315                 320
Gln Glu Val Thr Ala Glu Asp Gly Thr Gln Arg Cys Glu Lys Cys Ser
                325                 330                 335
Lys Pro Cys Ala Gly Val Cys Tyr Gly Leu Gly Met Glu His Leu Arg
             340                 345                 350
Gly Ala Arg Ala Ile Thr Ser Asp Asn Ile Gln Glu Phe Ala Gly Cys
         355                 360                 365
Lys Lys Ile Phe Gly Ser Leu Ala Phe Leu Pro Glu Ser Phe Asp Gly
    370                 375                 380
Asn Pro Ser Ser Gly Val Ala Pro Leu Lys Pro Glu His Leu Gln Val
385                 390                 395                 400
```

Figure 20b (SEQ ID NO:14)

```
Phe Glu Thr Leu Glu Glu Ile Thr Gly Tyr Leu Tyr Ile Ser Ala Trp
                405                 410                 415
Pro Glu Ser Phe Gln Asp Leu Ser Val Phe Gln Asn Leu Arg Val Ile
            420                 425                 430
Arg Gly Arg Ile Leu His Asp Gly Ala Tyr Ser Leu Thr Leu Gln Gly
        435                 440                 445
Leu Gly Ile His Ser Leu Gly Leu Arg Ser Leu Arg Glu Leu Gly Ser
    450                 455                 460
Gly Leu Ala Leu Ile His Arg Asn Thr His Leu Cys Phe Val Asn Thr
465                 470                 475                 480
Val Pro Trp Asp Gln Leu Phe Arg Asn Pro His Gln Ala Leu Leu His
                485                 490                 495
Ser Gly Asn Arg Pro Glu Glu Ala Cys Gly Leu Glu Gly Leu Val Cys
            500                 505                 510
Asn Ser Leu Cys Ala Arg Gly His Cys Trp Gly Pro Gly Pro Thr Gln
        515                 520                 525
Cys Val Asn Cys Ser Gln Phe Leu Arg Gly Gln Glu Cys Val Glu Glu
    530                 535                 540
Cys Arg Val Trp Lys Gly Leu Pro Arg Glu Tyr Val Arg Gly Lys His
545                 550                 555                 560
Cys Leu Pro Cys His Pro Glu Cys Gln Pro Gln Asn Ser Ser Glu Thr
                565                 570                 575
Cys Tyr Gly Ser Glu Ala Asp Gln Cys Glu Ala Cys Ala His Tyr Lys
            580                 585                 590
Asp Ser Ser Ser Cys Val Ala Arg Cys Pro Ser Gly Val Lys Pro Asp
        595                 600                 605
Leu Ser Tyr Met Pro Ile Trp Lys Tyr Pro Asp Glu Glu Gly Ile Cys
    610                 615                 620
Gln Pro Cys Pro Ile Asn Cys Thr His Ser Cys Val Asp Leu Asp Glu
625                 630                 635                 640
Arg Gly Cys Pro Ala Glu Gln Arg Ala Ser Pro Val Thr Phe Ile Ile
                645                 650                 655
Ala Thr Val Val Gly Val Leu Leu Phe Leu Ile Ile Val Val Val Ile
            660                 665                 670
Gly Ile Leu Ile Lys Arg Arg Arg Gln Lys Ile Arg Lys Tyr Thr Met
        675                 680                 685
Arg Arg Leu Leu Gln Glu Thr Glu Leu Val Glu Pro Leu Thr Pro Ser
    690                 695                 700
Gly Ala Val Pro Asn Gln Ala Gln Met Arg Ile Leu Lys Glu Thr Glu
705                 710                 715                 720
Leu Arg Lys Leu Lys Val Leu Gly Ser Gly Ala Phe Gly Thr Val Tyr
                725                 730                 735
Lys Gly Ile Trp Ile Pro Asp Gly Glu Asn Val Lys Ile Pro Val Ala
            740                 745                 750
Ile Lys Val Leu Arg Glu Asn Thr Ser Pro Lys Ala Asn Lys Glu Ile
        755                 760                 765
Leu Asp Glu Ala Tyr Val Met Ala Gly Val Gly Ser Pro Tyr Val Ser
    770                 775                 780
Arg Leu Leu Gly Ile Cys Leu Thr Ser Thr Val Gln Leu Val Thr Gln
785                 790                 795                 800
Leu Met Pro Tyr Gly Cys Leu Leu Asp His Val Arg Glu His Arg Gly
                805                 810                 815
```

Figure 20c (SEQ ID NO:14)

```
Arg Leu Gly Ser Gln Asp Leu Leu Asn Trp Cys Val Gln Ile Ala Lys
            820                 825                 830
Gly Met Ser Tyr Leu Glu Glu Val Arg Leu Val His Arg Asp Leu Ala
            835                 840                 845
Ala Arg Asn Val Leu Val Lys Ser Pro Asn His Val Lys Ile Thr Asp
    850                 855                 860
Phe Gly Leu Ala Arg Leu Leu Asp Ile Asp Glu Thr Glu Tyr His Ala
865                 870                 875                 880
Asp Gly Gly Lys Val Pro Ile Lys Trp Met Ala Leu Glu Ser Ile Leu
                885                 890                 895
Arg Arg Arg Phe Thr His Gln Ser Asp Val Trp Ser Tyr Gly Val Thr
            900                 905                 910
Val Trp Glu Leu Met Thr Phe Gly Ala Lys Pro Tyr Asp Gly Ile Pro
            915                 920                 925
Ala Arg Glu Ile Pro Asp Leu Leu Glu Lys Gly Glu Arg Leu Pro Gln
    930                 935                 940
Pro Pro Ile Cys Thr Ile Asp Val Tyr Met Ile Met Val Lys Cys Trp
945                 950                 955                 960
Met Ile Asp Ser Glu Cys Arg Pro Arg Phe Arg Glu Leu Val Ser Glu
                965                 970                 975
Phe Ser Arg Met Ala Arg Asp Pro Gln Arg Phe Val Val Ile Gln Asn
            980                 985                 990
Glu Asp Leu Gly Pro Ser Ser Pro Met Asp Ser Thr Phe Tyr Arg Ser
            995                 1000                1005
Leu Leu Glu Asp Asp Asp Met Gly Glu Leu Val Asp Ala Glu Glu Tyr
    1010                1015                1020
Leu Val Pro Gln Gln Gly Phe Phe Ser Pro Asp Pro Ala Leu Gly Thr
1025                1030                1035                1040
Gly Ser Thr Ala His Arg Arg His Arg Ser Ser Ser Ala Arg Ser Gly
                1045                1050                1055
Gly Gly Glu Leu Thr Leu Gly Leu Glu Pro Ser Glu Glu Glu Pro Pro
            1060                1065                1070
Arg Ser Pro Leu Ala Pro Ser Glu Gly Ala Gly Ser Asp Val Phe Asp
            1075                1080                1085
Gly Asp Leu Ala Val Gly Val Thr Lys Gly Leu Gln Ser Leu Ser Pro
    1090                1095                1100
His Asp Leu Ser Pro Leu Gln Arg Tyr Ser Glu Asp Pro Thr Leu Pro
1105                1110                1115                1120
Leu Pro Pro Glu Thr Asp Gly Tyr Val Ala Pro Leu Ala Cys Ser Pro
                1125                1130                1135
Gln Pro Glu Tyr Val Asn Gln Pro Glu Val Arg Pro Gln Ser Pro Leu
            1140                1145                1150
Thr Pro Glu Gly Pro Pro Pro Ile Arg Pro Ala Gly Ala Thr Leu
            1155                1160                1165
Glu Arg Pro Lys Thr Leu Ser Pro Gly Lys Asn Gly Val Val Lys Asp
    1170                1175                1180
Val Phe Ala Phe Gly Gly Ala Val Glu Asn Pro Glu Tyr Leu Ala Pro
1185                1190                1195                1200
Arg Ala Gly Thr Ala Ser Gln Pro His Pro Ser Pro Ala Phe Ser Pro
                1205                1210                1215
Ala Phe Asp Asn Leu Tyr Tyr Trp Asp Gln Asn Ser Ser Glu Gln Gly
            1220                1225                1230
```

Figure 20d (SEQ ID NO:14)

```
Pro Pro Pro Ser Thr Phe Glu Gly Thr Pro Thr Ala Glu Asn Pro Glu
        1235                1240                1245
Tyr Leu Gly Leu Asp Val Pro Val
    1250                1255
```

Western blot analysis of mNeu and mECDPD recombinants expressed in HEK293 lysates. Delta mNeu has a mutated kinase domain while mECDPD-TcP0 contains a 6-mer peptide encoding a ribosomal P-peptide epitope. The cNeu3 anti-PD antibody was used for detection of proteins.

Fig. 22a (SEQ ID NO:27)

```
Met Glu Leu Ala Ala Trp Cys Arg Trp Gly Phe Leu Leu Ala Leu Leu
                 5                  10                  15
Ser Pro Gly Ala Ala Gly Thr Gln Val Cys Thr Gly Thr Asp Met Lys
            20                  25                  30
Leu Arg Leu Pro Ala Ser Pro Glu Thr His Leu Asp Met Leu Arg His
        35                  40                  45
Leu Tyr Gln Gly Cys Gln Val Val Gln Gly Asn Leu Glu Leu Thr Tyr
    50                  55                  60
Leu Pro Ala Asn Ala Ser Leu Ser Phe Leu Gln Asp Ile Gln Glu Val
65                  70                  75                  80
Gln Gly Tyr Met Leu Ile Ala His Asn Arg Val Lys His Val Pro Leu
                85                  90                  95
Gln Arg Leu Arg Ile Val Arg Gly Thr Gln Leu Phe Glu Asp Lys Tyr
            100                 105                 110
Ala Leu Ala Val Leu Asp Asn Arg Asp Pro Leu Asp Asn Val Thr Thr
        115                 120                 125
Ala Ala Pro Gly Arg Thr Pro Glu Gly Leu Arg Glu Leu Gln Leu Arg
    130                 135                 140
Ser Leu Thr Glu Ile Leu Lys Gly Gly Val Leu Ile Arg Gly Asn Pro
145                 150                 155                 160
Gln Leu Cys Tyr Gln Asp Met Val Leu Trp Lys Asp Val Leu Arg Lys
                165                 170                 175
Asn Asn Gln Leu Ala Pro Val Asp Met Asp Thr Asn Arg Ser Arg Ala
            180                 185                 190
Cys Pro Pro Cys Ala Pro Thr Cys Lys Asp Asn His Cys Trp Gly Glu
        195                 200                 205
Ser Pro Glu Asp Cys Gln Ile Leu Thr Gly Thr Ile Cys Thr Ser Gly
    210                 215                 220
Cys Ala Arg Cys Lys Gly Arg Leu Pro Thr Asp Cys Cys His Glu Gln
225                 230                 235                 240
Cys Ala Ala Gly Cys Thr Gly Pro Lys His Ser Asp Cys Leu Ala Cys
                245                 250                 255
Leu His Phe Asn His Ser Gly Ile Cys Glu Leu His Cys Pro Ala Leu
            260                 265                 270
Ile Thr Tyr Asn Thr Asp Thr Phe Glu Ser Met Leu Asn Pro Glu Gly
        275                 280                 285
```

Fig. 22b (SEQ ID NO:27)

```
Arg Tyr Thr Phe Gly Ala Ser Cys Val Thr Thr Cys Pro Tyr Asn Tyr
    290             295                 300
Leu Ser Thr Glu Val Gly Ser Cys Thr Leu Val Cys Pro Pro Asn Asn
305             310                 315                     320
Gln Glu Val Thr Ala Glu Asp Gly Thr Gln Arg Cys Glu Lys Cys Ser
                325                 330                 335
Lys Pro Cys Ala Gly Val Cys Tyr Gly Leu Gly Met Glu His Leu Arg
            340                 345                 350
Gly Ala Arg Ala Ile Thr Ser Asp Asn Ile Gln Glu Phe Ala Gly Cys
            355                 360                 365
Lys Lys Ile Phe Gly Ser Leu Ala Phe Leu Pro Glu Ser Phe Asp Gly
            370                 375                 380
Asn Pro Ser Ser Gly Val Ala Pro Leu Lys Pro Glu His Leu Gln Val
385                 390                 395                 400
Phe Glu Thr Leu Glu Glu Ile Thr Gly Tyr Leu Tyr Ile Ser Ala Trp
                405                 410                 415
Pro Glu Ser Phe Gln Asp Leu Ser Val Phe Gln Asn Leu Arg Val Ile
                420                 425                 430
Arg Gly Arg Ile Leu His Asp Gly Ala Tyr Ser Leu Thr Leu Gln Gly
                435                 440                 445
Leu Gly Ile His Ser Leu Gly Leu Arg Ser Leu Arg Glu Leu Gly Ser
            450                 455                 460
Gly Leu Ala Leu Ile His Arg Asn Thr His Leu Cys Phe Val Asn Thr
465                 470                 475                 480
Val Pro Trp Asp Gln Leu Phe Arg Asn Pro His Gln Ala Leu Leu His
                485                 490                 495
Ser Gly Asn Arg Pro Glu Glu Ala Cys Gly Leu Glu Gly Leu Val Cys
                500                 505                 510
Asn Ser Leu Cys Ala Arg Gly His Cys Trp Gly Pro Gly Pro Thr Gln
            515                 520                 525
Cys Val Asn Cys Ser Gln Phe Leu Arg Gly Gln Glu Cys Val Glu Glu
            530                 535                 540
Cys Arg Val Trp Lys Gly Leu Pro Arg Glu Tyr Val Arg Gly Lys His
545                 550                 555                 560
Cys Leu Pro Cys His Pro Glu Cys Gln Pro Gln Asn Ser Ser Glu Thr
                565                 570                 575
```

Fig. 22c (SEQ ID NO:27)

```
Cys Tyr Gly Ser Glu Ala Asp Gln Cys Glu Ala Cys Ala His Tyr Lys
            580                 585                 590

Asp Ser Ser Ser Cys Val Ala Arg Cys Pro Ser Gly Val Lys Pro Asp
            595                 600                 605

Leu Ser Tyr Met Pro Ile Trp Lys Tyr Pro Asp Glu Glu Gly Ile Cys
            610                 615                 620

Gln Pro Cys Pro Ile Asn Cys Thr His Ser Cys Val Asp Leu Asp Glu
625                 630                 635                 640

Arg Gly Cys Pro Ala Glu Gln Arg Ala Ser Pro Val Thr Ser Gln Asn
            645                 650                 655

Glu Asp Leu Gly Pro Ser Ser Pro Met Asp Ser Thr Phe Tyr Arg Ser
            660                 665                 670

Leu Leu Glu Asp Asp Asp Met Gly Glu Leu Val Asp Ala Glu Glu Tyr
            675                 680                 685

Leu Val Pro Gln Gln Gly Phe Phe Ser Pro Asp Pro Ala Leu Gly Thr
            690                 695                 700

Gly Ser Thr Ala His Arg Arg His Arg Ser Ser Ala Arg Ser Gly
705                 710                 715                 720

Gly Gly Glu Leu Thr Leu Gly Leu Glu Pro Ser Glu Glu Pro Pro
            725                 730                 735

Arg Ser Pro Leu Ala Pro Ser Glu Gly Ala Gly Ser Asp Val Phe Asp
            740                 745                 750

Gly Asp Leu Ala Val Gly Val Thr Lys Gly Leu Gln Ser Leu Ser Pro
            755                 760                 765

His Asp Leu Ser Pro Leu Gln Arg Tyr Ser Glu Asp Pro Thr Leu Pro
            770                 775                 780

Leu Pro Pro Glu Thr Asp Gly Tyr Val Ala Pro Leu Ala Cys Ser Pro
785                 790                 795                 800

Gln Pro Glu Tyr Val Asn Gln Pro Glu Val Arg Pro Gln Ser Pro Leu
            805                 810                 815

Thr Pro Glu Gly Pro Pro Pro Ile Arg Pro Ala Gly Ala Thr Leu
            820                 825                 830

Glu Arg Pro Lys Thr Leu Ser Pro Gly Lys Asn Gly Val Val Lys Asp
            835                 840                 845

Val Phe Ala Phe Gly Gly Ala Val Glu Asn Pro Glu Tyr Leu Ala Pro
            850                 855                 860
```

Fig. 22d (SEQ ID NO:27)

```
Arg Ala Gly Thr Ala Ser Gln Pro His Pro Ser Pro Ala Phe Ser Pro
865             870             875                     880

Ala Phe Asp Asn Leu Tyr Tyr Trp Asp Gln Asn Ser Ser Glu Gln Gly
            885             890                 895

Pro Pro Pro Ser Thr Phe Glu Gly Thr Pro Thr Ala Glu Asn Pro Glu
            900             905                 910

Tyr Leu Gly Leu Asp Val Pro Val
        915             920
```

Fig. 23 (SEQ ID NO:28)

```
atggagctgg cggcctggtg ccgttggggg ttcctcctcg ccctcctgtc ccccggagcc 60
gcgggtaccc aagtgtgtac cggtaccgac atgaagttgc gactccctgc cagtcctgag 120
acccacctgg acatgcttcg ccacctctac cagggctgtc aggtggtgca gggcaatttg 180
gagcttacct acctgcccgc caatgccagc ctctcattcc tgcaggacat ccaggaagtc 240
cagggataca tgctcatcgc tcacaaccga gtgaaacacg tcccactgca gaggttgcgc 300
atcgtgagag ggactcagct cttcgaggac aagtatgccc tggctgtgct agacaaccga 360
gacccctttgg acaacgtcac caccgccgcc ccaggcagaa ccccagaagg gctgcgggag 420
ctgcagcttc gaagtctcac agagatcttg aaggggaggag ttttgatccg tgggaaccct 480
cagctctgct accaggacat ggttttgtgg aaggatgtcc tccgtaagaa taaccagctg 540
gctcctgtcg acatggacac caatcgttcc cgggcctgtc caccttgtgc ccaacctgc 600
aaagacaatc actgttgggg tgagagtcct gaagactgtc agatcttgac tggcaccatc 660
tgtactagtg gctgtgcccg gtgcaagggc cggctgccca ctgactgttg ccatgagcag 720
tgtgctgcag gctgcacggg tcccaagcat tctgactgcc tggcctgcct ccacttcaat 780
catagtggta tctgtgagct gcactgcccg gccctcatca cctacaacac agacaccttc 840
gagtccatgc tcaaccctga gggtcgctac acctttggtg ccagctgtgt gaccacctgc 900
ccctacaact acctctccac ggaagtggga tcctgcactc tggtctgtcc cccgaacaac 960
caagaggtca cagctgagga cggaacacag cggtgtgaga aatgcagcaa gcctgtgct 1020
ggagtatgct atggtctggg catggagcac ctccgagggg cgagggccat caccagtgac 1080
aatatccagg agtttgctgg ctgcaagaag atctttggca gcctgcatt tttgccggag 1140
agctttgatg gaaccccctc ctccggcgtt gccccactga agccagagca tctccaagtg 1200
ttcgaaaccc tggaggagat cacaggttac ctatacattt cagcatggcc agagagcttc 1260
caagacctca gtgtcttcca gaaccttcgg gtcattcggg gacggattct ccatgatggt 1320
gcttactcat tgacgttgca aggcctgggg attcactcac tggggctacg ctcactgcgg 1380
gagctgggca gtggattggc tctcattcac cgcaacaccc atctctgctt tgtaaacact 1440
gtaccttggg accagctctt ccggaacccg caccaggccc tactccacag tgggaaccgg 1500
ccagaagagg catgtggtct tgagggcttg gtctgtaact cactgtgtgc ccgtgggcac 1560
tgctgggggc cagggcccac ccagtgtgtc aactgcagtc agttcctccg gggccaggag 1620
tgtgtggagg agtgccgagt atggaagggg ctcccagggg agtatgtgag gggcaagcac 1680
tgtctgccat gccaccccga gtgtcagcct caaaacagct cggagacctg ctatggatcg 1740
gaggctgacc agtgtgaggc ttgtgcccac tacaaggact catcttcctg tgtggctcgc 1800
tgccccagtg gtgtgaagcc agacctctcc tacatgccta tctggaagta cccggatgag 1860
gagggcatat gtcagccatg ccccatcaac tgcacccact catgtgtgga cctggacgaa 1920
cgaggctgcc cagcagagca gagagccagc cagtgacgt ctcagaacga ggacttaggc 1960
ccctccagcc ccatggacag caccttctac cgttcactgc tggaggatga tgacatgggg 2020
gagctggtcg atgctgaaga gtaccggta ccccagcagg gattcttctc cccagaccct 2080
gccctaggta ctgggagcac agcccaccgc agacaccgca gctcgtcggc caggagtggc 2140
ggtggtgagc tgacactggg cctggagccc tcggaagaag agccccccag atctccactg 2200
gctccctccg aaggggctgg ctccgatgtg tttgatggtg acctggcagt ggggggtaacc 2260
aaaggactgc agagcctctc tccacatgac ctcagccctc tacagcggta cagtgaggat 2320
cccacattac ctctgccccc cgagactgat ggctacgttg ctcccctggc tgcagcccc 2380
cagcccgagt atgtgaacca gccagaggtt cggcctcagt ctcccttgac cccagagggt 2440
cctccgcctc ccatccgacc tgctggtgct actctagaaa gacccaagac tctctctcct 2500
gggaaaaatg gggttgtcaa agacgttttt gcctttgggg gtgctgtgga aaccctgaa 2560
tacctagcac ccagagcagg cactgcctct cagcccaccc cttctcctgc cttcagccca 2620
gcctttgaca acctctatta ctgggaccag aactcatcgg agcagggtcc tccaccaagt 2680
accttgaag ggaccccac tgcagagaac cctgagtacc taggcctgga tgtgccagta 2760
tga                                                            2763
```

Fig. 24a (SEQ ID NO:29)

```
Met Glu Leu Ala Ala Trp Cys Arg Trp Gly Phe Leu Leu Ala Leu Leu
                 5                  10                  15

Ser Pro Gly Ala Ala Gly Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Ala Asn Ala Ser Leu Ser Phe Leu Gln Asp Ile Gln Glu Val
65                  70                  75                  80

Gln Gly Tyr Met Leu Ile Ala His Asn Arg Val Lys His Val Pro Leu
                85                  90                  95

Gln Arg Leu Arg Ile Val Arg Gly Thr Gln Leu Phe Glu Asp Lys Tyr
                100                 105                 110

Ala Leu Ala Val Leu Asp Asn Arg Asp Pro Leu Asp Asn Val Thr Thr
            115                 120                 125

Ala Ala Pro Gly Arg Thr Pro Glu Gly Leu Arg Glu Leu Gln Leu Arg
        130                 135                 140

Ser Leu Thr Glu Ile Leu Lys Gly Gly Val Leu Ile Arg Gly Asn Pro
145                 150                 155                 160

Gln Leu Cys Tyr Gln Asp Met Val Leu Trp Lys Asp Val Leu Arg Lys
                165                 170                 175

Asn Asn Gln Leu Ala Pro Val Asp Met Asp Thr Asn Arg Ser Arg Ala
            180                 185                 190

Cys Pro Pro Cys Ala Pro Thr Cys Lys Asp Asn His Cys Trp Gly Glu
        195                 200                 205

Ser Pro Glu Asp Cys Gln Ile Leu Thr Gly Thr Ile Cys Thr Ser Gly
    210                 215                 220

Cys Ala Arg Cys Lys Gly Arg Leu Pro Thr Asp Cys Cys His Glu Gln
225                 230                 235                 240

Cys Ala Ala Gly Cys Thr Gly Pro Lys His Ser Asp Cys Leu Ala Cys
                245                 250                 255

Leu His Phe Asn His Ser Gly Ile Cys Glu Leu His Cys Pro Ala Leu
            260                 265                 270
```

Fig. 24b (SEQ ID NO:29)

```
Ile Thr Tyr Asn Thr Asp Thr Phe Glu Ser Met Leu Asn Pro Glu Gly
        275                 280                 285

Arg Tyr Thr Phe Gly Ala Ser Cys Val Thr Thr Cys Pro Tyr Asn Tyr
        290                 295                 300

Leu Ser Thr Glu Val Gly Ser Cys Thr Leu Val Cys Pro Pro Asn Asn
305                     310                 315                 320

Gln Glu Val Thr Ala Glu Asp Gly Thr Gln Arg Cys Glu Lys Cys Ser
                325                 330                 335

Lys Pro Cys Ala Gly Val Cys Tyr Gly Leu Gly Met Glu His Leu Arg
                340                 345                 350

Gly Ala Arg Ala Ile Thr Ser Asp Asn Ile Gln Glu Phe Ala Gly Cys
            355                 360                 365

Lys Lys Ile Phe Gly Ser Leu Ala Phe Leu Pro Glu Ser Phe Asp Gly
        370                 375                 380

Asn Pro Ser Ser Gly Val Ala Pro Leu Lys Pro Glu His Leu Gln Val
385                 390                 395                     400

Phe Glu Thr Leu Glu Glu Ile Thr Gly Tyr Leu Tyr Ile Ser Ala Trp
                405                 410                 415

Pro Glu Ser Phe Gln Asp Leu Ser Val Phe Gln Asn Leu Arg Val Ile
                420                 425                 430

Arg Gly Arg Ile Leu His Asp Gly Ala Tyr Ser Leu Thr Leu Gln Gly
            435                 440                 445

Leu Gly Ile His Ser Leu Gly Leu Arg Ser Leu Arg Glu Leu Gly Ser
450                 455                 460

Gly Leu Ala Leu Ile His Arg Asn Thr His Leu Cys Phe Val Asn Thr
465                 470                 475                     480

Val Pro Trp Asp Gln Leu Phe Arg Asn Pro His Gln Ala Leu Leu His
                485                 490                 495

Ser Gly Asn Arg Pro Glu Glu Ala Cys Gly Leu Glu Gly Leu Val Cys
                500                 505                 510

Asn Ser Leu Cys Ala Arg Gly His Cys Trp Gly Pro Gly Pro Thr Gln
            515                 520                 525

Cys Val Asn Cys Ser Gln Phe Leu Arg Gly Gln Glu Cys Val Glu Glu
                530                 535                 540

Cys Arg Val Trp Lys Gly Leu Pro Arg Glu Tyr Val Arg Gly Lys His
545                 550                 555                     560
```

Fig. 24c (SEQ ID NO:29)

```
Cys Leu Pro Cys His Pro Glu Cys Gln Pro Gln Asn Ser Ser Glu Thr
                565                 570                 575
Cys Tyr Gly Ser Glu Ala Asp Gln Cys Glu Ala Cys Ala His Tyr Lys
                580                 585                 590
Asp Ser Ser Ser Cys Val Ala Arg Cys Pro Ser Gly Val Lys Pro Asp
                595                 600                 605
Leu Ser Tyr Met Pro Ile Trp Lys Tyr Pro Asp Glu Glu Gly Ile Cys
                610                 615                 620
Gln Pro Cys Pro Ile Asn Cys Thr His Ser Cys Val Asp Leu Asp Glu
625                 630                 635                 640
Arg Gly Cys Pro Ala Glu Gln Arg Ala Ser Pro Val Thr Ser Gln Asn
                645                 650                 655
Glu Asp Leu Gly Pro Ser Ser Pro Met Asp Ser Thr Phe Tyr Arg Ser
                660                 665                 670
Leu Leu Glu Asp Asp Asp Met Gly Glu Leu Val Asp Ala Glu Glu Tyr
                675                 680                 685
Leu Val Pro Gln Gln Gly Phe Phe Ser Pro Asp Pro Ala Leu Gly Thr
                690                 695                 700
Gly Ser Thr Ala His Arg Arg His Arg Ser Ser Ala Arg Ser Gly
705                 710                 715                 720
Gly Gly Glu Leu Thr Leu Gly Leu Glu Pro Ser Glu Glu Glu Pro Pro
                725                 730                 735
Arg Ser Pro Leu Ala Pro Ser Glu Gly Ala Gly Ser Asp Val Phe Asp
                740                 745                 750
Gly Asp Leu Ala Val Gly Val Thr Lys Gly Leu Gln Ser Leu Ser Pro
                755                 760                 765
His Asp Leu Ser Pro Leu Gln Arg Tyr Ser Glu Asp Pro Thr Leu Pro
                770                 775                 780
Leu Pro Pro Glu Thr Asp Gly Tyr Val Ala Pro Leu Ala Cys Ser Pro
785                 790                 795                 800
Gln Pro Glu Tyr Val Asn Gln Pro Glu Val Arg Pro Gln Ser Pro Leu
                805                 810                 815
Thr Pro Glu Gly Pro Pro Pro Ile Arg Pro Ala Gly Ala Thr Leu
                820                 825                 830
Glu Arg Pro Lys Thr Leu Ser Pro Gly Lys Asn Gly Val Val Lys Asp
                835                 840                 845
```

Fig. 24d (SEQ ID NO:29)

```
Val Phe Ala Phe Gly Gly Ala Val Glu Asn Pro Glu Tyr Leu Ala Pro
    850                 855                 860
Arg Ala Gly Thr Ala Ser Gln Pro His Pro Ser Pro Ala Phe Ser Pro
865                 870                 875                 880
Ala Phe Asp Asn Leu Tyr Tyr Trp Asp Gln Asn Ser Ser Glu Gln Gly
            885                 890                 895
Pro Pro Pro Ser Thr Phe Glu Gly Thr Pro Thr Ala Glu Asn Pro Glu
            900                 905                 910
Tyr Leu Gly Leu Asp Val Pro Val Gly Met Gly Ala Leu Phe
            915                 920                 925
```

Fig. 25 (SEQ ID NO:30)

```
atggagctgg cggcctggtg ccgttggggg ttcctcctcg ccctcctgtc ccccggagcc   60
gcgggtaccc aagtgtgtac cggtaccgac atgaagttgc gactccctgc cagtcctgag  120
acccacctgg acatgcttcg ccacctctac cagggctgtc aggtggtgca gggcaatttg  180
gagcttacct acctgcccgc caatgccagc ctctcattcc tgcaggacat ccaggaagtc  240
cagggataca tgctcatcgc tcacaaccga gtgaaacacg tcccactgca gaggttgcgc  300
atcgtgagag ggactcagct ctttgaggac aagtatgccc tggctgtgct agacaaccga  360
gaccctttgg acaacgtcac caccgccgcc ccaggcagaa ccccagaagg gctgcgggag  420
ctgcagcttc gaagtctcac agagatcttg aaggaggag ttttgatccg tggaacccct  480
cagctctgct accaggacat ggttttgtgg aaggatgtcc tccgtaagaa taaccagctg  540
gctcctgtcg acatggacac caatcgttcc cgggcctgtc caccttgtgc cccaacctgc  600
aaagacaatc actgttgggg tgagagtcct gaagactgtc agatcttgac tggcaccatc  660
tgtactagtg gctgtgcccg gtgcaagggc cggctgccca ctgactgttg ccatgagcag  720
tgtgctgcag gctgcacggg tcccaagcat tctgactgcc tggcctgcct ccacttcaat  780
catagtggta tctgtgagct gcactgcccg gccctcatca cctacaacac agacaccttc  840
gagtccatgc tcaaccctga gggtcgctac acctttggtg ccagctgtgt gaccacctgc  900
ccctacaact acctctccac ggaagtggga tcctgcactc tggtctgtcc ccgaacaac   960
caagaggtca gctgagga cggaacacag cggtgtgaga atgcagcaa gccctgtgct  1020
ggagtatgct atggtctggg catggagcac ctccgagggg cgagggccat caccagtgac  1080
aatatccagg agtttgctgg ctgcaagaag atctttggga gcctggcatt tttgccggag  1140
agctttgatg ggaaccctc ctccggcgtt gccccactga gccagagca tctccaagtg  1200
ttcgaaaccc tggaggagat cacaggttac ctatacattt cagcatggcc agagagcttc  1260
caagacctca gtgtcttcca gaaccttcgg gtcattcggg acggattct ccatgatggt  1320
gcttactcat tgacgttgca aggcctgggg attcactcac tggggctacg ctcactgcgg  1380
gagctgggca gtggattggc tctcattcac cgcaacaccc atctctgctt tgtaaacact  1440
gtaccttggg accagctctt ccggaacccg caccaggcc tactccacag tgggaaccgg  1500
ccagaagagg catgtggtct tgagggcttg gtctgtaact cactgtgtgc ccgtgggcac  1560
tgctgggggc cagggcccac ccagtgtgtc aactgcagtc agttcctccg ggccaggag  1620
tgtgtggagg agtgccgagt atggaagggg ctccccaggg agtatgtgag gggcaagcac  1680
tgtctgccat gccaccccga gtgtcagcct caaaacagct cggagacctg ctatggatcg  1740
gaggctgacc agtgtgaggc ttgtgcccac tacaaggact catcttcctg tgtggctcgc  1800
tgccccagtg gtgtgaagcc agacctctcc tacatgccta tctggaagta cccggatgag  1860
gagggcatat gtcagccatg ccccatcaac tgcacccact catgtgtgga cctggacgaa  1920
cgaggctgcc cagcagagca gagagccagc ccagtgacgt ctcagaacga ggacttaggc  1980
ccctccagcc ccatggacag caccttctac cgttcactgc tggaggatga tgacatgggg  2040
gagctggtcg atgctgaaga gtacctggta ccccagcagg gattcttctc cccagaccct  2100
gccctaggta ctgggagcac agcccaccgc agacaccgca gctcgtcggc caggagtggc  2160
ggtggtgagc tgacactggg cctggagccc tcggaagaag agccccccag atctccactg  2220
gctccctccg aagggctgg ctccgatgtg tttgatggtg acctggcagt ggggtaacc  2280
aaaggactgc agagcctctc tccacatgac ctcagccctc tacagcggta cagtgaggat  2340
cccacattac ctctgccccc cgagactgat ggctacgttg ctccctggc ctgcagcccc  2400
cagcccgagt atgtgaacca gccagaggtt cggcctcagt ctcccttgac ccagagggt  2460
cctccgcctc ccatccgacc tgctggtgct actctagaaa gacccaagac tctctctcct  2520
gggaaaaatg gggttgtcaa agacgttttt gcctttgggg tgctgtgga gaaccctgaa  2580
tacctagcac ccagagcagg cactgcctct cagccccacc cttctcctgc cttcagccca  2640
gcctttgaca acctctatta ctgggaccag aactcatcgg agcagggtcc tccaccaagt  2700
acctttgaag ggacccccac tgcagagaac cctgagtacc taggcctgga tgtgccagta  2760
ggaatgggcg cgctgttcta a                                          2781
```

Fig. 26 (SEQ ID NO:31)

```
Gly Met Gly Ala Leu Phe
             5
```

Fig. 27 (SEQ ID NO:32)

```
ggaatgggcg cgctgttc    18
```

HER-2/NEU FUSION PROTEINS

CROSS-REFERENCES TO RELATED APPLICATIONS

The present application claims the benefit of U.S. patent application Ser. No. 09/493,480, filed Jan. 28, 2000 and U.S. provisional patent application No. 60/117,976, filed Jan. 29, 1999.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Despite enormous investments of financial and human resources, cancer remains one of the major causes of death. For example, cancer is the leading cause of death in women between the ages of 35 and 74. Breast cancer is the most common malignancy in women and the incidence for developing breast cancer is on the rise. It is estimated that one in nine women will be diagnosed with the disease. Standard approaches to cure breast cancer have centered around a combination of surgery, radiation and chemotherapy. These approaches have resulted in some dramatic successes in certain malignancies. However, breast cancer is most often incurable, when diagnosed beyond a certain stage. Alternative approaches to early diagnosis and therapy are necessary.

A common characteristic of malignancies is uncontrolled cell growth. Cancer cells appear to undergo a process of transformation from the normal phenotype to a malignant phenotype capable of autonomous growth. Amplification and overexpression of somatic cell genes is considered to be a common primary event that results in the transformation of normal cells to malignant cells. The malignant phenotypic characteristics encoded by the oncogenic genes are passed on during cell division to the progeny of the transformed cells.

At least forty oncogenes operative in malignant cells and responsible for, or associated with, transformation have been identified. These oncogenes have been classified into different groups based on the putative function or location of their gene products, such as the protein expressed by the oncogene.

Oncogenes are believed to be essential for certain aspects of normal cellular physiology. In this regard, the Her-2/neu oncogene appears to be a member of the tyrosine kinase family of receptor-like glycoproteins, and shares a high degree of identity with the epidermal growth factor receptor (EGFR). Her-2/neu presumably plays a role in cell growth and/or differentiation. Her-2/neu appears to induce malignancies through quantitative mechanisms that result from increased or deregulated expression of an essentially normal gene product.

The p185 glycoprotein is the protein product of the Her-2/neu oncogene. The Her-2/neu gene is amplified and p185 is overexpressed in a variety of cancers including breast, ovarian, colon, lung and prostate cancer. p185 is related to malignant transformation, and is found in 50–60% of ductal in situ carcinomas, in 20–40% of invasive breast cancers, and in a substantial fraction of adenocarcinomas arising in the ovaries, prostate, colon and lung. Her-2/neu expression is intimately associated not only with malignant phenotype, but also with the aggressiveness of the malignancy. Her-2/neu overexpression is correlated with a poor prognosis in both breast and ovarian cancers.

p185 is a transmembrane protein with a predicted relative molecular mass of 185 kD that is about 1255 amino acids in length. p185 has an extracellular domain (ECD) of about 645 amino acids with at least a 40% identity to EGFR, a highly hydrophobic transmembrane domain, and a carboxy terminal intracellular domain (ICD) of about 580 amino acids with at least an 80% identity to EGFR.

There is a need for anti-cancer vaccines that can target a malignancy with which the Her-2/neu oncogene is associated, and for compositions and methods that can elicit and enhance an immune response to the Her-2/neu gene. The present invention is directed to these, as well as other, important ends.

SUMMARY OF THE INVENTION

The present invention provides Her-2/neu p185 fusion proteins, nucleic acid molecules that encode Her-2/neu fusion proteins, and viral vectors that comprise polynucleotide sequences encoding Her-2/neu fusion proteins, for uses that include the immunization of warm-blooded animals against malignancies with which the Her-2/neu oncogene is associated. In one embodiment, the fusion proteins of the present invention further comprise a TcP0 motif. In another embodiment, the fusion proteins of the invention further comprise an NS1 antigen or an immunogenic fragment thereof, preferably attached to the N-terminus of the fusion protein. Fusion proteins or nucleic acid molecules according to the invention may be present in compositions that include a pharmaceutically acceptable carrier or diluent, e.g., an oil-in water emulsion, and optionally include one or more additional active ingredients, such as an immunostimulatory substance, e.g., SBAS-2, SBAS-4, 3D-MPL, QS21, or a combination of 3D-MPL and QS21. The compositions of the invention are useful as, and can be in the form of vaccines. The fusion proteins, nucleic acid molecules, viral vectors, pharmaceutical compositions and/or vaccines may be administered on a one-time basis (e.g., for an individual with an elevated risk of acquiring or reacquiring a malignancy or when a malignancy is suspected) or on a periodic basis (e.g., for an individual with an elevated risk of acquiring or reacquiring a malignancy or when a malignancy is suspected). Compounds or compositions of the present invention are useful in treating one or more existing tumors, or preventing tumor occurrence or reoccurrence, in warm-blooded animals including humans.

The present invention also provides methods for inhibiting or preventing the development of a cancer in a patient by eliciting or enhancing and immune response to the Her-2/neu protein, comprising administering to a patient a pharmaceutical composition or vaccine as recited above. The patient may be afflicted with, e.g., breast, ovarian, colon, lung or prostate cancer, in which case the methods provide treatment for the disease, or a patient considered at risk for such a disease may be treated prophylactically. In one embodiment, the administration of the pharmaceutical composition or vaccine comprises transfecting cells of a warm-blooded animal ex vivo with a nucleic acid molecule of the invention or infecting cells of a warm-blooded animal ex vivo with a viral vector comprising a nucleic acid molecule of the invention, and subsequently delivering the transfected or infected cells to the warm-blooded animal. The viral vector is preferably an adenovirus or an alphavirus.

The present invention further provides, within other aspects, methods for removing tumor cells from a biological sample, comprising contacting a biological sample with T cells that specifically react with a Her-2/neu fusion protein, wherein the step of contacting the sample is performed under conditions and for a time sufficient to permit the removal of cells expressing the protein from the sample. Within related aspects, methods are provided for inhibiting the development of a cancer in a patient, comprising administering to a patient a biological sample treated as described supra.

In another embodiment, methods are provided for stimulating and/or expanding T cells specific for a Her-2/neu fusion protein, comprising contacting T cells with one or more of: (i) a fusion protein as described above; (ii) a polynucleotide encoding such a fusion protein; and/or (iii) an antigen presenting cell that expresses such a fusion protein; under conditions and for a time sufficient to permit the stimulation and/or expansion of T cells. Isolated T cell populations comprising T cells prepared as described above are also provided. Within further aspects, the present invention provides methods for inhibiting the development of a cancer in a patient, comprising administering to a patient an effective amount of a T cell population as described above.

In yet another embodiment, the present invention further provides methods for inhibiting the development of a cancer in a patient, comprising the steps of: (a) incubating CD4$^+$ and/or CD8$^+$ T cells isolated from a patient with one or more of: (i) a Her-2/neu fusion protein; (ii) a polynucleotide encoding such a fusion protein; and (iii) an antigen-presenting cell that expresses such a fusion protein; and (b) administering to the patient an effective amount of the proliferated T cells, thereby inhibiting the development of a cancer in the patient. Proliferated cells may, but need not, be cloned prior to administration to the patient.

Finally, the invention provides a method of making a Her-2/neu fusion protein, the method comprising the steps of (a) introducing into a cell an expression vector comprising a polynucleotide encoding a Her-2/neu fusion protein; (b) culturing the transfected cell; and (c) purifying the expressed protein. In a preferred embodiment, the cell is a CHO or a BHK cell. In another preferred embodiment, the cell is cultured in suspension, under serum-free conditions. In yet another embodiment the expressed protein is purified by a two-step procedure, comprising an anion exchange chromatography on Q sepharose High Performance Columns, and a hydrophobic chromatography on Phenyl Sepharose 6 Fast Flow low substitution.

These and other aspects of the present invention will become apparent upon reference to the following detailed description and attached drawings.

BRIEF DESCRIPTION OF THE DRAWINGS

FIG. 7 shows the full length amino acid sequence of the human Her-2/neu protein (SEQ ID NO:1).

FIG. 8 shows the full length amino acid sequence of the rat Her-2/neu protein (SEQ ID NO:2). The kinase domain spans the region from amino acid 721 to amino acid 998, inclusively.

FIG. 9 shows the amino acid sequence of the extracellular domain of the human Her-2/neu protein (SEQ ID NO:3).

FIG. 10 shows the amino acid sequence of the phosphorylation domain (PD) of the human Her-2/neu protein (SEQ ID NO:4).

FIG. 11 shows the amino acid sequence of a preferred portion of the phosphorylation domain (ΔPD) of the human Her-2/neu protein (SEQ ID NO:5).

FIG. 12 shows the amino acid sequence of a fusion protein comprising the extracellular domain (ECD) and the phosphorylation domain (PD) of the human Her-2/neu protein (SEQ ID NO:6).

FIG. 13 shows the amino acid sequence of a fusion protein comprising the extracellular domain (ECD) and a preferred portion of the phosphorylation domain (ΔPD) of the human Her-2/neu protein (SEQ ID NO:7).

FIG. 14 shows the amino acid sequence of the extracellular domain (ECD) of the rat Her-2/neu protein (SEQ ID NO:8).

FIG. 15 shows the full length nucleotide sequence (SEQ ID NO:9) of a DNA molecule encoding the human Her-2/neu protein and the deduced amino acid sequence of the encoded protein. This full length nucleotide sequence is described in WO 96/30514.

FIG. 16 shows the full length nucleotide sequence (SEQ ID NO:10) of a DNA molecule encoding the rat Her-2/neu protein. This full length nucleotide sequence is described by Bargmann et al. (1986) *Nature* 319:226–30, and GEN-BANK/X03362.

FIG. 19 shows the nucleotide sequence of a DNA molecule encoding the mouse Her-2/neu protein (SEQ ID NO:11).

FIG. 20 shows the amino acid sequence of the mouse Her-2/neu protein (SEQ ID NO:14).

FIG. 22 shows the amino acid sequence of the mouse ECD-PD fusion protein (SEQ ID NO:27).

FIG. 23 shows the nucleotide sequence of a cDNA molecule encoding the mouse ECD-PD fusion protein (SEQ ID NO:28).

FIG. 24 shows the amino acid sequence of the mouse ECD-PD-TcP0 fusion protein (SEQ ID NO:29).

FIG. 25 shows the nucleotide sequence of a cDNA molecule encoding the mouse ECD-PD-TcP0 fusion protein (SEQ ID NO:30).

FIG. 26 shows the amino acid sequence of the TcP0 peptide (SEQ ID NO:31).

FIG. 27 shows a nucleotide sequence encoding the TcP0 peptide (SEQ ID NO:32).

DESCRIPTION OF THE SPECIFIC EMBODIMENTS

I. Introduction

Figure 1:
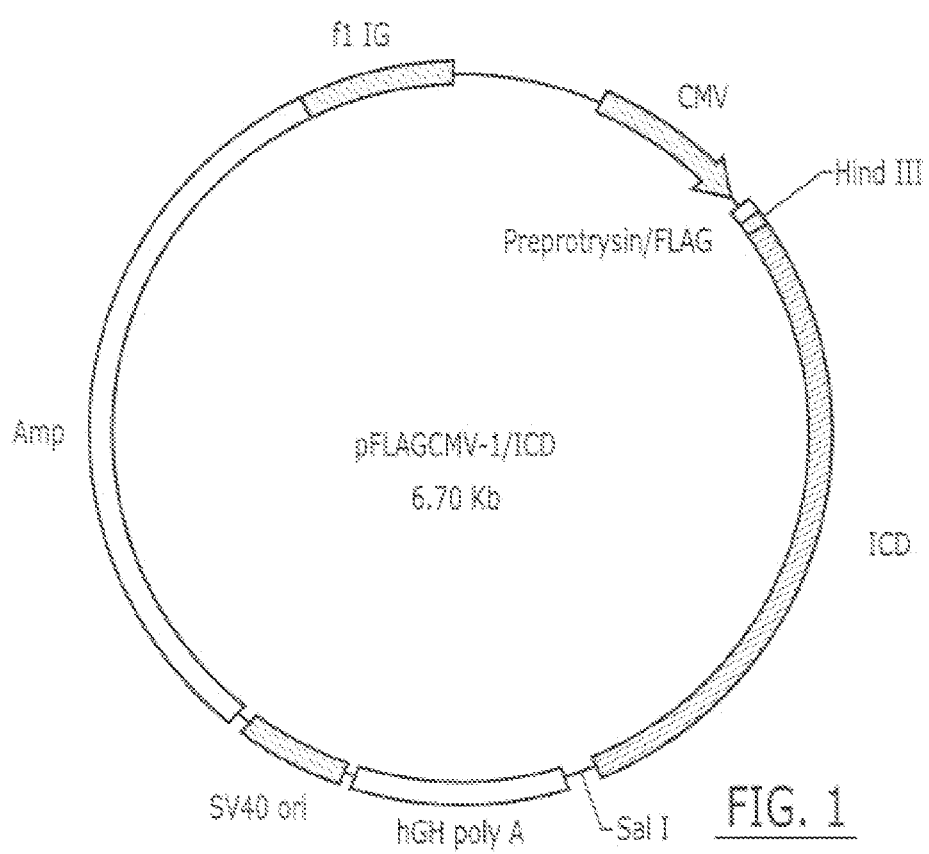
FIG. 1 shows a map of the pFLAGCMV-1/ICD expression plasmid, which has a size of 6.7 kb.

The present invention is directed to compounds and compositions capable of modulating, preferably eliciting or enhancing, immunity to the protein product of Her-2/neu oncogene expression, including for malignancies in a warm-blooded animal where an amplified Her-2/neu gene with a malignancy does not require that the protein expression product of the gene be present on the tumor. For example, overexpression of the gene may be involved with initiation and early stages of tumor formation, but the protein expression may subsequently be reduced or absent. The present invention may be used to elicit or enhance an effective immune response to convert a Her-2/neu positive tumor to Her-2/neu negative, in addition to preventing the establishment of Her-2/neu positive tumors and provoking the regression of existing Her-2/neu positive tumors.

The following abbreviations are used throughout the specification: "ECD" refers to the extracellular domain, "ICD" refers to the intracellular domain, "PD" refers to the phosphorylation domain (i.e., the domain that is phosphorylated) that is within the intracellular domain, "ΔPD" refers to a fragment of the phosphorylation domain that is within the phosphorylation domain, and "KD" refers to the kinase domain that is within the intracellular domain. "Delta Her-2/neu" refers to a Her-2/neu protein containing an amino acid change in PD that eliminates the kinase activity. For example, the nucleotide sequence encoding the mouse Delta Her-2/neu protein (Delta mNeu) comprises an A to T nucleotide change at position 2261 of the cDNA encoding the mouse Her-2/neu protein that results in a Lysine to a Methionine amino acid change. The product of expression of the Her-2/neu gene is referred to herein as the "Her-2/neu protein," also known and referred to as "p185" or "c-erbB2."

II. Definitions

The "Her-2/neu ECD-ICD fusion protein," also referred to herein as "ECD-ICD" or "ECD-ICD fusion protein," refers to a fusion protein (or fragments thereof) comprising the extracellular domain (or fragments thereof) and the intracellular domain (or fragments thereof) of the Her-2/neu protein. As used herein, the ECD-ICD fusion protein does not include a substantial portion of the Her-2/neu transmembrane domain, and preferably does not include any of the Her-2/neu transmembrane domain.

The "Her-2/neu ECD-PD fusion protein," also referred to as "ECD-PD" or "ECD-PD fusion protein," or the "Her-2/neu ECD-ΔPD fusion protein," also referred to as "ECD-ΔPD" or "ECD-ΔPD fusion protein," refer to fusion proteins (or fragments thereof) comprising the extracellular domain (or fragments or fragments thereof) and phosphorylation domain (or fragments or fragments thereof, e.g., the ΔPD or the PD of the Delta Her-2/neu protein) of the Her-2/neu protein. The ECD-PD and ECD-ΔPD fusion proteins do not include a substantial portion of the Her-2/neu transmembrane domain, and preferably do not include any of the Her-2/neu transmembrane domain.

The terms "Her-2/neu ECD-ICD fusion protein" and "Her-2/neu ECD-PD fusion protein" and their related terms are also understood to refer to fragments thereof, homologs thereof and functional equivalents thereof (collectively referred to as "variants"), such as those in which one or more amino acids is inserted, deleted or replaced by other amino acid(s) or non-amino acid(s) which, in preferred embodiments of the invention, either (i) increase the elicitation or enhancement of an immune response as compared to the Her-2/neu protein, or (ii) do not substantially affect elicitation or enhancement of an immune response as compared to the Her-2/neu protein (e.g., a variant that stimulates a response by helper T cells or cytotoxic T cells or that stimulates the production of antibodies). Specific, non-limiting, examples of variants including exemplary fragments, homologs and functional equivalents of the Her-2/neu ECD-ICD fusion protein and Her-2/neu ECD-PD fusion protein are described in more detail herein. Variants can be "substantially identical" or "substantially similar" to a fusion protein comprising native polypeptide components, and retain the ability to stimulate an immune response.

A "fusion protein" refers to a protein having at least two polypeptides covalently linked, in which one polypeptide comes from one protein sequence or domain and the other polypeptide comes from another protein sequence or domain. The polypeptides can be linked either directly or via a covalent linker, e.g., an amino acid linker, such as a polyglycine linker, or another type of chemical linker, e.g., a carbohydrate linker, a lipid linker, a fatty acid linker, a polyether linker, e.g., PEG, etc. (see, e.g., Hermanson (1996) *Bioconjugate techniques*). The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. The term "fusion protein" also refers to conservatively modified variants, polymorphic variants, alleles, mutant, subsequences and interspecies homologues of the polypeptides that make up the fusion protein. Fusion proteins may be produced by covalently linking a chain of amino acids from one protein sequence to a chain of amino acids from another protein sequence, e.g., by preparing a recombinant polynucleotide contiguously encoding the fusion protein. Fusion proteins can comprise 2, 3, 4 or more different chains of amino acids from the same or different species. The different chains of amino acids in a fusion protein may be directly spliced together or may be indirectly spliced together via a chemical linking group or an amino acid linking group. The fusion protein may optionally comprise other components, as described in more detail herein.

The term "protein" is used herein interchangeably with "polypeptide" and "peptide."

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605–2608; Rossolini et al. (1994) *Mol. Cell. Probes* 8:91–98). The term nucleic acid is used interchangeably with gene, cDNA, mRNA, oligonucleotide, and polynucleotide.

A polynucleotide sequence comprising a fusion protein of the invention hybridizes under stringent conditions to each of the nucleotide sequences encoding each individual polypeptide of the fusion protein. The polynucleotide sequences encoding the individual polypeptides of the fusion polypeptide therefore include conservatively modified variants, polymorphic variants, alleles, mutants, subsequences, and interspecies homologs.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99% or higher, compared to a reference sequence using the programs described herein, preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like. "Substantial identity" of amino acid sequences for these purposes normally means sequence identity of at least 40%. Preferred percent identity of polypeptides can be any integer from 40% to 100%. More preferred embodiments include at least 60%, 65%, 70%, 75%, 80%, 85%, 90%, 95%, or 99%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Optimal alignment of sequences for comparison may be conducted by the local identity algorithm of Smith and Waterman (1981) *Add. APL. Math.* 2:482, by the identity alignment algorithm of Needleman and Wunsch (1970) *J. Mol. Biol.* 48:443, by the search for similarity method of Pearson and Lipman (1988) *Proc. Natl. Acad. Sci. U.S.A.* 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

A preferred example of algorithms that are suitable for determining percent sequence identity and sequence similarity are the BLAST and BLAST 2.0 algorithms, which are described in Altschul et al. (1977) *Nuc. Acids Res.* 25:3389–3402 and Altschul et al. (1990) *J. Mol. Biol.* 215:403–410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

Another indication that nucleotide sequences are substantially identical is if two molecules hybridize to each other, or to a third nucleic acid, under moderately, and preferably highly, stringent conditions. Stringent conditions are sequence dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5–10° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent conditions will be those in which the salt concentration is less than about 1.0 M sodium ion, typically about 0.01 to 1.0 M sodium ion concentration (or other salts)

at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

For the purpose of the invention, suitable "moderately stringent conditions" include, for example, prewashing in a solution of 5×SSC, 0.5% SDS, 1.0 mM EDTA (pH 8.0), hybridizing at 50° C.–65° C., 5×SSC overnight, followed by washing twice at 65° C. for 20 minutes with each of 2×, 0.5× and 0.2×SSC (containing 0.1% SDS). Such hybridizing DNA sequences are also within the scope of this invention.

"Proliferation of T cells," as described herein, includes the multiplication of T cells as well as the stimulation of T cells leading to multiplication, i.e., the initiation of events leading to mitosis and mitosis itself. Methods for detecting proliferation of T cells are discussed below.

III. Fusion Proteins of the Invention

A. Intra- and Extracellular Domains of the Her-2/neu Protein

The Her-2/neu protein was selected as a target for anti-cancer vaccines based on observations of Her-2/neu as described above. One of the major obstacles to this approach is the difficulty of isolating a sufficient amount of Her-2/neu protein. One attempt to address this problem was to express the ECD and ICD separately in mammalian cells. The ECD expressed at a high level as a secreted protein, i.e., about 20 mg of the ECD protein were purified from one liter of mouse cell culture. However, the level of expression of ICD was low, i.e., only about 0.2 mg of the ICD protein were purified from one liter of HEK-293 cultured cells. In addition, the resulting ICD protein was very labile in cell lysate, creating numerous unexpected problems for purification of useful quantities.

As discussed above, Her-2/neu is an oncogenic self protein, and immunological tolerance to self proteins can dampen the immune response. The level of immunological tolerance to different portions of any particular protein may depend upon whether the expressed portion of the protein resides within or without the cell membrane. The ECD resides on the cell surface and is shed. By contrast, the ICD and portions thereof reside inside the cell and are not shed. The ECD readily comes in contact with the body's immune system, whereas the ICD and portions thereof are relatively sequestered from the body's immune system. As a result, the level of immunologic tolerance to ECD is greater than that to the ICD portion of the Her-2/neu protein. Thus, for vaccines according to the present invention, ICD protein and ICD peptides, and variants thereof, including PD proteins and PD peptides, induce a relatively greater level of immune response than ECD protein and ECD peptides.

Although the ICD and its variants are more immunogenic than the ECD and its variants, antibodies to ECD and its variants are beneficial and possibly desirable. The ECD resides at the cell surface whereas the ICD and portions thereof are not secreted and are sequestered inside the cell. Thus, antibody responses to the ECD can have a greater therapeutic benefit, and accordingly are preferred according to the invention. The ECD by itself is not very immunogenic. Since the ICD (including the PD and ΔPD) is more immunogenic than the ECD, an ECD-ICD fusion protein and/or an ECD-PD fusion protein are more immunogenic than the ECD alone. The ECD-ICD and/or the ECD-PD fusion proteins are expected to be more effective for inducing antibodies to the ECD than the ECD alone, and are a preferred embodiment of the invention.

In the present invention, the ECD or its variants is combined, linked or fused (either directly or indirectly) with the ICD or its variants, preferably with the PD or its variants. The ECD provides the structural conformation for inducing antibodies that react with Her-2/neu protein at the cell surface, while the ICD or PD increases the immunogenicity of the ECD. The combination is surprisingly more effective for inducing an immune response to the ECD than the ECD alone.

The ECD, or portions thereof, can be combined with the ICD or its variants, including portions of the ICD or with the PD or its variants, including portions of the PD (e.g., the ΔPD or the PD of the Delta Her-2/neu protein). The ECD of the present invention is preferably a human, a rat or a mouse ECD. The human ECD is set forth in FIG. 9 and as SEQ ID NO:3. The rat ECD is set forth in FIG. 14 and as SEQ ID NO:8.

The ICD of the present invention is preferably a human, a rat or a mouse ICD. The human ICD is set forth in FIG. 7 and SEQ ID NO:1 as inclusively spanning the region of Lys 676 to Val 1255. The rat ICD is set forth in FIG. 8 and SEQ ID NO:2 as inclusively spanning the region of Lys 677 to Val 1256.

The PD of the present invention is preferably a human, a rat or a mouse PD. The human PD is set forth in FIG. 10 and as SEQ ID NO:4. The human PD may be the human ΔPD, which is set forth in FIG. 11 and as SEQ ID NO:5. The rat PD is shown in FIG. 8 and SEQ ID NO:2 as inclusively spanning the region of Gln 991 to Val 1256. The rat PD may be the rat ΔPD, which is shown in FIG. 8 and SEQ ID NO:2 as inclusively spanning the region of Gln 991 to Arg 1049.

In one embodiment, a human ECD can be fused with either (i) a human ICD or a rat ICD or (ii) a human PD or ΔPD, or a rat PD or ΔPD. In another embodiment, a rat ECD can be fused with either (i) a human ICD or a rat ICD or (ii) a human PD or ΔPD, or a rat PD or ΔPD. In yet another embodiment, a mouse ECD can be fused with a mouse PD.

The Her-2/neu PD is 268 amino acids in length, is intracellular, and can be phosphorylated by protein tyrosine kinases. This region shares no identity with the corresponding part of other tyrosine kinase receptors. Thus, the specificity and uniqueness of this domain makes it particularly preferred for use as a tumor vaccine. However, the expression of this domain alone in bacteria and mammalian cells is problematic. For example, the resultant PD protein is very labile and is not appropriate for large scale production. In one embodiment, this invention has solved such problems by fusing all or part of the intracellular domain or the phosphorylation domain to all or part of the Her-2/neu extracellular domain. The ECD-ICD fusion proteins and the ECD-PD fusion proteins of the invention are soluble, are secreted and are stable in culture media. This system can provide large quantities of intracellular domain or phosphorylation domain protein for cancer vaccine development, preferably breast cancer vaccine development, but will be useful for vaccines against any cancer characterized by Her-2/neu expression. In addition to allowing increased expression of the intracellular domain or phosphorylation domain, or variants thereof, as a fusion protein with the extracellular domain or its variants, the ECD-ICD and ECD-PD fusion proteins provide for an improved vaccine formulation.

The PD was secreted by introducing a secretion signal sequence preceding the N-terminus of the PD to yield a soluble, secreted recombinant protein. The secretion process is preferred since the recombinant proteins accumulate in the culture media. Because the protein is not associated with the intracellular proteins, proteolysis is limited. The protein can thus be purified more easily and economically.

As described in Example 3, the pFLAGCMV-1 expression plasmid (Kodak) was used to determine which region of the Her-2/neu intracellular domain was able to be secreted. The proteins were expressed as fusion proteins with a preprotrypsin secretion signal and FLAG-Tag at their N-terminus. HEK-293 cells were transfected with such constructs, and cell and culture media were assayed for FLAG-Tag fusion proteins by western blot with FLAG-Tag M2 antibody as probe. The results in FIG. 4 demonstrate that neither full length ICD nor KD was secreted, but that the PD was soluble and was secreted and detected in the culture media. The results indicate that the full length structure ICD or KD protein did not result in secretion, that is in passage of the protein through the cell membrane.

Figure 6A:
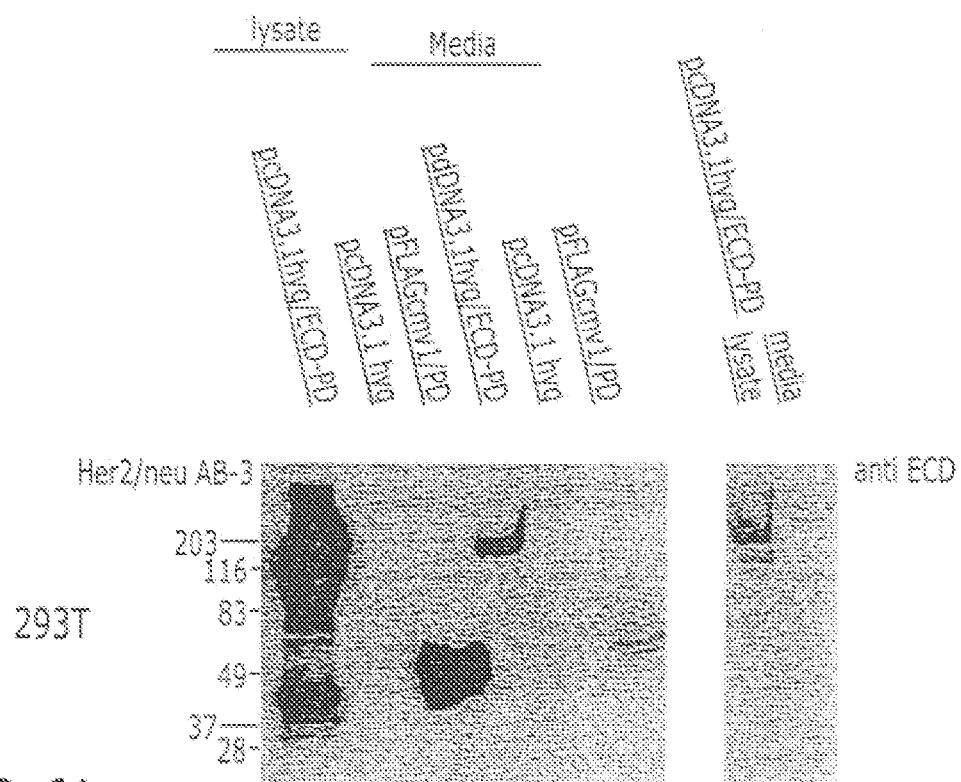
FIG. 6 illustrates the results of the expression of the ECD-PD fusion protein in HEK-293 and CHO cells, and shows that the fusion protein was secreted into the culture media, as described in Example 4.
Figure 6B:
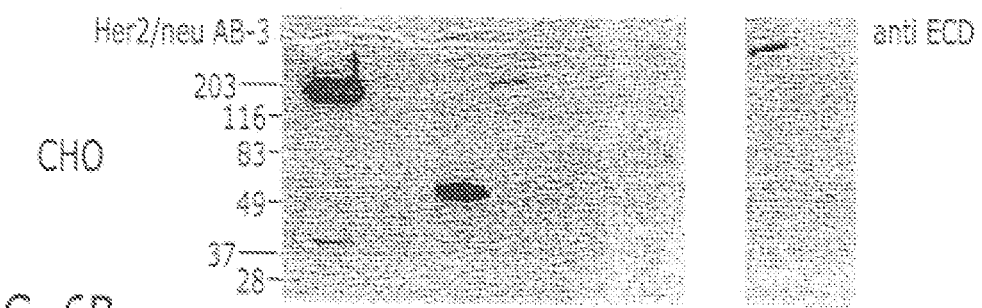

As described in Example 4, since the ECD has a secretion signal sequence and can be expressed well as a secreted protein, the ECD was used as a fusion partner for PD. The ECD-PD fusion protein was expressed in HEK-293 cells. The secretion of soluble ECD-PD fusion protein was determined by ELISA assay with Her-2/neu ECD-specific antibodies, followed by western blot with Her-2/neu PD-specific antibodies. As shown in FIG. 6, the soluble ECD-PD expressed in HEK-293 and was secreted into the culture medium.

B. Immunogenicity of the Fusion Proteins of the Invention

In a preferred embodiment, the present invention is directed to a fusion protein based on particular portions (e.g., Her-2/neu ECD-ICD fusion protein or Her-2/neu ECD-PD fusion protein) of the protein expression product of the Her-2/neu gene, which is capable of eliciting an antibody response and can be recognized by thymus-dependent lymphocytes ("T cells"). Accordingly, the autochthonous immune T cell response can be used prophylactically or to treat malignancies in which Her-2/neu is or has been overexpressed. In another aspect, the present invention is directed to the use of nucleic acid molecules directing the expression of such ECD-ICD fusion proteins or =ECD-PD fusion proteins, or their variants, alone or in a viral vector for immunization.

In general, $CD4^+$ T cell populations are considered to function as helpers or inducers through the release of lymphokines when stimulated by a specific antigen; however, a subset of $CD4^+$ cells can act as cytotoxic T lymphocytes (CTL). Similarly, $CD8^+$ T cells are considered to function by directly lysing antigenic targets; however, under a variety of circumstances they can secrete lymphokines to provide helper or DTH function. Despite the potential of overlapping function, the phenotypic CD4 and CD8 markers are linked to the recognition of peptides bound to class I or class II MHC antigens. The recognition of an antigen in the context of class I or class II MHC mandates that $CD4^+$ and $CD8^+$ T cells respond to different antigens or to the same antigen presented under different circumstances. The binding of immunogenic peptides to class II MHC antigens most commonly occurs for antigens ingested by antigen presenting cells.

As disclosed within the present invention, an ECD-ICD fusion protein or an ECD-PD fusion protein of the protein expression product of the Her-2/neu oncogene is recognized by T cells. Circulating Her-2/neu ECD-ICD fusion protein or Her-2/neu ECD-PD fusion protein is degraded to peptide fragments. Peptide fragments from the ECD-ICD fusion protein or ECD-PD fusion protein bind to major histocompatibility complex (MHC) antigens. By display of a peptide bound to MHC antigen on the cell surface and recognition by host T cells of the combination of peptide plus self MHC antigen, the Her-2/neu ECD-ICD or the Her-2/neu ECD-PD fusion protein (including that expressed on a malignant cell) are immunogenic to T cells. The exquisite specificity of the T cell receptor enables individual T cells to discriminate between protein fragments which differ by a single amino acid residue.

During the immune response to a peptide fragment from an ECD-ICD or an ECD-PD fusion protein, T cells expressing a T cell receptor with high affinity binding of the peptide-MHC complex binds to the peptide-MHC complex and thereby become activated and induced to proliferate. In the first encounter with a peptide, small numbers of immune T cells will secrete lymphokines, proliferate and differentiate into effector and memory T cells. The primary immune response will occur in vivo but has been difficult to detect in vitro. A subsequent encounter with the same antigen by the memory T cells will lead to a faster and more intense immune response. The secondary response will occur either in vivo or in vitro. The in vitro response is easily gauged by measuring the degree of proliferation, the degree of cytokine production, or the generation of cytolytic activity of the T cell population re-exposed to the antigen. Substantial proliferation of the T cell population in response to a particular antigen is considered to be indicative of prior exposure to or priming with the antigen.

C. Fusion Proteins of the Invention

In one embodiment, the compounds of the present invention comprise Her-2/neu ECD-ICD fusion proteins or variants, or polynucleotides that encode such ECD-ICD fusion proteins. Preferably, the nucleic acid molecules are DNA molecules. In the Her-2/neu ECD-ICD fusion proteins of the invention, the ECD and ICD polypeptide components can be directly fused or fused via a linker, e.g., an amino acid linker or another type of chemical linker. In a preferred embodiment, the ECD-ICD fusion proteins of the present invention comprise all or a portion of the Her-2/neu ECD fused directly to all or a portion of the Her-2/neu ICD.

In additional embodiments, the size of the ECD in the ECD-ICD fusion protein can be altered by sequentially removing anywhere from 1 to about 100 amino acids from the carboxyl terminus of the ECD, preferably about 100 amino acids. Similarly, the size of the ICD in the ECD-ICD fusion protein can be altered by sequentially removing anywhere from 1 to about 100 amino acids from the N-terminus and/or the C-terminus of the ICD. The resulting variant forms may be selected on the basis of their antigenicity and/or immunogenicity using appropriate screening methods as described in the literature and herein, for use according to the invention.

In another embodiment, the compounds of the present invention comprise Her-2/neu ECD-PD fusion proteins, or variants, or nucleic acid molecules that encode such ECD-PD fusion proteins. In one embodiment, the Her-2/neu ECD is fused to the Her-2/neu ΔPD. Preferably, the nucleic acid molecules are DNA molecules. In the Her-2/neu ECD-PD fusion proteins of the invention, the ECD and PD or ΔPD polypeptide components can be directly fused or fused via a linker, e.g., a peptide linker. In a preferred embodiment, the ECD-PD fusion protein of the present invention comprises the Her-2/neu ECD fused directly to the Her-2/neu PD or to the Her-2/neu ΔPD. Here and throughout the specification, a preferred embodiment of the fusion proteins of the invention is the Her-2/neu PD fusion protein.

In another embodiment, the size of the ECD in the ECD-PD fusion protein is altered by sequentially removing anywhere from 1 to about 100 amino acids from the carboxyl terminus of the ECD, preferably about 100 amino acids. Similarly, the size of the PD in the ECD-PD fusion protein can be altered by sequentially removing amino acids from the N-terminus of the PD. Again, the preferred embodiment is PD. Other variant forms may be selected on the basis of their antigenicity and/or immunogenicity using appropriate screening methods as described in the literature and herein, for use according to the invention.

Table 1 below shows that removing 100 amino acids from the carboxyl terminus of the ECD does not have any impact on the expression level and stability of the ECD-PD fusion protein.

TABLE 1

$ECD_{truncated}$-PD Summary

| Clone I.D. | area of deletion (bp/aa) | # of bp | # of aa | relative expression |
|---|---|---|---|---|
| A5 | 1655–1882/552–628 | 228 | 76 | *** |
| B4 | 1660–1866/554–622 | 207 | 69 | ** |
| B9 | 1595–1891/532–631 | 297 | 99 | *** |
| C2 | 1681–1902/561–634 | 222 | 74 | * |
| C7 | 1612–1902/538–634 | 291 | 97 | ***** |
| F10 | 1634–1951/545–651 | 318 | 106 | **** |
| ECD-PD WT | — | — | — | * |

Variants of the ECD-ICD fusion protein and the ECD-PD fusion protein also include various structural forms of the native ECD-ICD fusion protein and ECD-PD fusion protein, respectively. Due to the presence of ionizable amino and carboxyl groups, for example, a Her-2/neu ECD-ICD or ECD-PD fusion protein can be in the form of an acidic or basic salt, or may be in a neutral form. Individual amino acid residues may also be modified by oxidation or reduction.

Other variants within the scope of the invention include ECD-ICD fusion proteins or ECD-PD fusion proteins in which the primary amino acid structure native Her-2/neu ECD-ICD protein or native Her-2/neu ECD-PD protein, respectively, is modified by forming covalent or aggregative conjugates with other peptides or polypeptides, or chemical moieties such as glycosyl groups, lipids, phosphate, acetyl groups and the like. Covalent derivatives may be prepared, for example, by linking particular functional groups to amino acid side chains or at the N- or C-terminus. In somes embodiments, the fusion proteins of the invention further comprise a TcP0 peptide motif (SEQ ID NO:31).

The present invention also includes Her-2/neu ECD-ICD fusion proteins and Her-2/neu ECD-PD fusion proteins with or without glycosylation. ECD-ICD fusion proteins and ECD-PD fusion proteins expressed in yeast or mammalian expression systems may be similar to, or slightly different in molecular weight and glycosylation pattern from, the native molecules, depending upon the expression system. Expression of DNA encoding polypeptides in bacteria such as *E. coli* typically provides non-glycosylated molecules. N-glycosylation sites of eukaryotic proteins are characterized by the amino acid triplet Asn-$A_1$-Z, wherein $A_1$ is any amino acid except Pro, and Z is Ser or Thr. Variants of Her-2/neu ECD-ICD or ECD-PD fusion proteins having inactivated N-glycosylation sites can be produced by techniques known to one skilled in the art, such as oligonucleotide synthesis and ligation or site-specific mutagenesis techniques, and are within the scope of the invention. Alternatively, N-linked glycosylation sites can be added to a Her-2/neu ECD-ICD or ECD-PD fusion protein.

The ECD-ICD fusion proteins of the present invention, which will be understood to include variants, include any possible combination between human and non-human polypeptides. Non-human polypeptides comprise polypeptides from any mammal, such as, e.g., rat, mouse, guinea pig, horse, cow, pig, sheep, dog, etc. In one embodiment, the ECD-ICD fusion proteins include:

(i) human ECD—human ICD fusion proteins, such as those formed by linking the human ECD of FIG. 9 (SEQ ID NO:3) with the human ICD, which is the amino acid sequence inclusively spanning Lys 676 to Val 1255, as shown in FIG. 7 (SEQ ID NO:1), with or without a chemical and/or amino acid linking group, and variants thereof;

(ii) rat ECD—rat ICD fusion proteins, such as those formed by linking the rat ECD of FIG. 14 (SEQ ID NO:8) with the rat ICD, which is the amino acid sequence inclusively spanning Lys 677 to Val 1256, as shown in FIG. 8 (SEQ ID NO:2), with or without a chemical and/or amino acid linking group, and variants thereof;

(iii) human ECD—rat ICD fusion proteins, such as those formed by linking the human ECD shown in FIG. 9 (SEQ ID NO:3) with the rat ICD, which is the amino acid sequence inclusively spanning Lys 677 to Val 1256, as shown in FIG. 8 (SEQ ID NO:2), with or without a chemical and/or amino acid linking group, and variants thereof; and (iv) rat ECD—human ICD fusion proteins, such as those formed by linking the rat ECD, as shown in FIG. 14 (SEQ ID NO:8), with the human ICD, which is the amino acid sequence inclusively spanning Lys 676 to Val 1255, as shown in FIG. 7 (SEQ ID NO:1), with or without a chemical and/or amino acid linking group, and variants thereof.

Any variants of the ECD-ICD fusion proteins of the present invention are included as embodiments of the present invention. In one embodiment, such variants are substantially identical or substantially similar to the native Her-2/neu ECD-ICD protein and retain the ability to stimulate an immune response. Human DNA sequences that encode the ECD protein are shown, for example, in FIG. 15 (SEQ ID NO:9) as inclusively spanning nucleotide 1 to nucleotide 1959. Human DNA sequences that encode the ICD protein are shown, for example, in FIG. 15 (SEQ ID NO:9) as inclusively spanning nucleotide 2026 to nucleotide 3765. The effect of any sequence modification on the ability of a Her-2/neu ECD-ICD protein to produce an immune response may be readily determined, for example, by analyzing the ability of the mutated Her-2/neu ECD-ICD protein to induce a T cell response using, for example, the methods described herein, or by analyzing the ability of the mutated Her-2/neu ECD-ICD protein to produce antibodies.

The ECD-PD fusion proteins of the present invention, which will be understood to include variants, include any possible combination between human and non-human polypeptides. Non-human polypeptides comprise, e.g., rat, mouse, guinea pig, horse, cow, pig, sheep, dog, etc. In one embodiment, the ECD-PD fusion proteins include:

(i) human ECD—human PD fusion proteins, such as shown in FIG. 12 (SEQ ID NO:6) and variants thereof, including fusion proteins formed by linking the human ECD of FIG. 9 (SEQ ID NO:3) with the human PD of FIG. 10

(SEQ ID NO:4) with or without a chemical and/or amino acid linking group, and variants thereof;

(ii) rat ECD—rat PD fusion proteins, such as those formed by linking the rat ECD of FIG. 14 (SEQ ID NO:8) with the rat PD, which is the amino acid sequence inclusively spanning Gln 991 to Val 1256, as shown in FIG. 8 (SEQ ID NO:2), with or without a chemical and/or amino acid linking group, and variants thereof;

(iii) human ECD—rat PD fusion proteins, such as those formed by linking the human ECD shown in FIG. 9 (SEQ ID NO:3) with the rat PD, which is the amino acid sequence inclusively spanning Gln 991 to Val 1256, as shown in FIG. 8 (SEQ ID NO:2), with or without a chemical and/or amino acid linking group, and variants thereof; and (iv) rat ECD—human PD fusion proteins, such as those formed by linking the rat ECD, as shown in FIG. 14 (SEQ ID NO:8), with the human PD, as shown in FIG. 10 (SEQ ID NO:4), with or without a chemical and/or amino acid linking group, and variants thereof.

(v) mouse ECD—mouse PD fusion proteins, such as those shown in FIG. 22 (SEQ ID NO:27).

Any variants of the ECD-PD fusion proteins of the present invention are included as embodiments of the present invention. In one embodiment, such variants are substantially identical or substantially similar to the native Her-2/neu ECD-PD protein and retain the ability to stimulate an immune response. Human DNA sequences that encode the ECD protein are shown, for example, in FIG. 15 (SEQ ID NO:9) as inclusively spanning nucleotide 1 to nucleotide 1959. Human DNA sequences that encode the PD protein are shown, for example, in FIG. 15 (SEQ ID NO:9) as inclusively spanning nucleotide 2968 to nucleotide 3765. Mouse DNA sequences that encode the mouse ECD-PD fusion proteins are shown in FIG. 23 (SEQ ID NO:28). The effect of any sequence modification on the ability of a Her-2/neu ECD-PD protein to produce an immune response may be readily determined, for example, by analyzing the ability of the mutated Her-2/neu ECD-PD protein to induce a T cell response using, for example, the methods described herein, or by analyzing the ability of the mutated Her-2/neu ECD-PD protein to produce antibodies.

In another embodiment, the ECD-PD fusion proteins are ECD-ΔPD fusion proteins of the present invention, which will be understood to include variants, including any possible combination between human and non-human polypeptides. Non-human polypeptides comprise, e.g., rat, mouse, guinea pig, horse, cow, pig, sheep, dog, etc. In one embodiment, the ECD-ΔPD fusion proteins include:

(i) human ECD—human ΔPD fusion proteins, such as shown in FIG. 13 (SEQ ID NO:7) and variants thereof, including fusion proteins formed by linking the human ECD of FIG. 9 (SEQ ID NO:3) with the human ΔPD of FIG. 11 (SEQ ID NO:5) with or without a chemical and/or amino acid linking group, and variants thereof;

(ii) rat ECD—rat ΔPD fusion proteins, such as those formed by linking the rat ECD of FIG. 14 (SEQ ID NO:8) with the rat ΔPD, which is the amino acid sequence inclusively spanning Gln 991 to Arg 1049, as shown in FIG. 8 (SEQ ID NO:2), with or without a chemical and/or amino acid linking group, and variants thereof;

(iii) human ECD—rat ΔPD fusion proteins, such as those formed by linking the human ECD shown in FIG. 9 (SEQ ID NO:3) with the rat ΔPD, which is the amino acid sequence inclusively spanning Gln 991 to Arg 1049, as shown in FIG. 8 (SEQ ID NO:2), with or without a chemical and/or amino acid linking group, and variants thereof; and (iv) rat ECD—human ΔPD fusion proteins, such as those formed by linking the rat ECD, as shown in FIG. 14 (SEQ ID NO:8), with the human ΔPD, as shown in FIG. 11 (SEQ ID NO:5), with or without a chemical and/or amino acid linking group, and variants thereof.

Any variants of the ECD-ΔPD fusion proteins of the present invention are included as embodiments of the present invention. In one embodiment, such variants are substantially identical or substantially similar to the native Her-2/neu ECD-ΔPD protein and retain the ability to stimulate an immune response. Human DNA sequences that encode the ECD protein are shown, for example, in FIG. 15 (SEQ ID NO:9) as inclusively spanning nucleotide 1 to nucleotide 1959. Human DNA sequences that encode the ΔPD protein are shown, for example, in FIG. 15 (SEQ ID NO:9) as inclusively spanning nucleotide 2968 to nucleotide 3144. The effect of any sequence modification on the ability of a Her-2/neu ECD-ΔPD protein to produce an immune response may be readily determined, for example, by analyzing the ability of the mutated Her-2/neu ECD-ΔPD protein to induce a T cell response using, for example, the methods described herein, or by analyzing the ability of the mutated Her-2/neu ECD-ΔPD protein to produce antibodies.

In a preferred embodiment, the Her-2/neu ECD-PD fusion proteins of the invention are ECD-PD fusion proteins.

Within certain specific embodiments, the fusion proteins of the invention may comprise a fusion partner, such as, e.g., an immunological fusion partner or an expression enhancer. A fusion partner may, for example, assist in providing T helper epitopes (an immunological fusion partner), preferably T helper epitopes recognized by humans, or may assist in expressing the fusion protein (an expression enhancer) at higher yields than the recombinant fusion protein. Certain preferred fusion partners are both immunological and expression enhancing fusion partners. Other fusion partners may be selected so as to increase the solubility of the fusion protein or to enable the fusion protein to be targeted to desired intracellular compartments. Still further fusion partners include affinity tags, which facilitate the purification of the fusion protein of interest.

Also provided are fusion proteins that comprise a fusion polypeptide as described herein together with an unrelated immunogenic protein. Preferably, the immunogenic protein is capable of eliciting a recall response. Examples of such proteins include tetanus, tuberculosis and hepatitis proteins (see, e.g., Stoute et al. (1997) *New Engl. J. Med.* 336:86–91).

In other embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100–110 amino acids), and the protein D derivative may be lipidated. Within certain preferred embodiments, the first 109 residues of a Lipoprotein D fusion partner are included on the N-terminus to provide the fusion protein with additional exogenous T-cell epitopes and to increase the expression level in *E. coli* (thus functioning as an expression enhancer). The lipid tail ensures optimal presentation of the fusion protein to antigen presenting cells. Other fusion partners include the non-structural protein from influenzae virus, NS1 (hemaglutinin), or an immunogenic portion thereof (see, e.g., WO 99/40188 and WO 93/04175). Typically, the N-terminal 81 amino acids are used, although different fragments that include T-helper epitopes may be used. In one embodiment, the fusion proteins of the present invention further comprise the NS1 fusion partner or an immunogenic fragment thereof, preferably attached to the N-terminal region of the fusion protein. The fusion proteins comprising the NS1 partner are preferably recombinantly expressed in BHK cells, as described infra.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see, *Biotechnology* 10:795–798 (1992)). Within a preferred embodiment, a repeat portion of LYTA may be incorporated into a fusion protein. A repeat portion is found in the C-terminal region starting at residue 178. A particularly preferred repeat portion incorporates residues 188–305.

In a preferred embodiment, the fusion proteins of the invention further comprise a TcP0 peptide motif, which enhances the immunogenicity of the fusion protein. TcP0 is a 6 amino acid peptide from a ribosomal P protein that has been shown to induce epitope spreading. The TcP0 motif can be attached to the fusion protein at different sites, but is preferably fused to the C-terminus of the fusion protein. The amino acid sequence of TcP0 is shown in FIG. 26 (SEQ ID NO:31), and the nucleic acid sequence encoding TcP0 is shown in FIG. 27 (SEQ ID NO:32). Recombinant nucleic acids encoding a fusion protein comprising the TcP0 motif can be obtained using standard techniques or as described infra. Recombinant nucleic acids are constructed so that, preferably, the TcP0 polynucleotide sequence is located 3' to the fusion protein of interest.

In another preferred embodiment, the fusion proteins of the present invention further comprise a fusion partner. Preferred fusion partners include, but are not limited to, e.g., Ra12 or LeIF. In particular, the invention provides materials and methods for using a Ra12 or a LeIF sequence as a fusion partner to facilitate the stable and high yield expression of recombinant fusion polypeptides or break tolerance.

Ra12 is a 14 kD C-terminal fragment of the *M tuberculosis* MTB32A coding sequence, which is expressed at high levels on its own and remains soluble throughout the purification process. LeIF is a *Leishmania* antigen which is homologous to the eukaryotic ribosomal protein eIF and which is capable of stimulating a Th1 and/or CTL immune response (see, e.g., U.S. Pat. Nos. 5,876,966, 5,876,735, and 5,879,687). The present invention utilizes these properties of the Ra12 and LeIF polypeptides and provides recombinant nucleic acid molecules, expression vectors, host cells, and methods for stable and high yield expression of fusion polypeptides comprising, in addition to the Her-2/neu fusion polypeptides, a Ra12 or LeIF polypeptide. Recombinant nucleic acids, which encode a fusion polypeptide comprising a Ra12 or LeIF polypeptide and a fusion protein of interest, can be readily constructed by conventional genetic engineering techniques. Recombinant nucleic acids are constructed so that, preferably, the fusion partner polynucleotide sequence is located 5' to a selected fusion protein sequence. It may also be appropriate to place an fusion partner polynucleotide sequence 3' to the polynucleotide sequence of the fusion protein of interest or to insert the polynucleotide sequence of the fusion protein into a site within an fusion partner polynucleotide sequence. In addition, any suitable polynucleotide that encodes a fusion partner or a portion or other variant thereof as described herein can be used in constructing recombinant fusion nucleic acids of the present invention.

Nucleic acids encoding the fusion partner polypeptides of this invention can be prepared by any suitable method known in the art. Exemplary methods include cloning and restriction of appropriate sequences or direct chemical synthesis by methods such as the phosphotriester method of Narang et al. (1979) *Meth. Enzymol.* 68:90–99; the phosphodiester method of Brown et al. (1979) *Meth. Enzymol.* 68:109–151; the diethylphosphoramidite method of Beaucage et al. (1981) *Tetra. Lett.* 22:1859–1862; and the solid support method of U.S. Pat. No. 4,458,066.

Recombinant nucleic acids that encode a fusion polypeptide comprising a fusion partner polypeptide and a selected fusion protein can be prepared using any methods known in the art. As described above, recombinant nucleic acids are constructed so that, preferably, the fusion partner polynucleotide sequence is located 5' to the polynucleotide sequence encoding the fusion protein of interest. The fusion partner and fusion protein polynucleotide sequences can also be modified to facilitate their fusion and subsequent expression.

The recombinant nucleic acids can further comprise other nucleotide sequences such as sequences that encode affinity tags to facilitate protein purification protocol.

D. Variants of the Fusion Proteins of the Invention $CD4^+$ T cells generally recognize antigens that have been external to the tumor cells. By contrast, under normal circumstances, binding of peptides to class I MHC occurs only for proteins present in the cytosol and synthesized by the target itself, proteins in the external environment are excluded. An exception to this is the binding of exogenous peptides with a precise class I binding motif which are present outside the cell in high concentration. Thus, $CD4^+$ and $CD8^+$ T cells have broadly different functions and tend to recognize different antigens as a reflection of where the antigens normally reside.

Another way to make amino acid substitutions to produce variants of the present invention is to identify and replace amino acids in T cell motifs with potential to bind to class II MHC molecules (for $CD4^+$ T cell response) or class I MHC molecules (for $CD8^+$ T cell response). Peptide segments (of a Her-2/neu ECD-ICD or ECD-PD fusion protein) with a motif with theoretical potential to bind to class II MHC molecules may be identified by computer analysis. For example, a protein sequence analysis package, T Sites, that incorporates several computer algorithms designed to distinguish potential sites for T cell recognition can be used (Feller et al. (1991) *Nature* 349:720–721). Two searching algorithms are used: (1) the AMPHI algorithm described by Margalit (Feller et al. (1991) *Nature* 349:720–721; Margalit et al. (1987) *J. Immunol.* 138:2213–2229) identifies epitope motifs according to alpha-helical periodicity and amphipathicity; (2) the Rothbard and Taylor algorithm identifies epitope motifs according to charge and polarity pattern (Rothbard et al. (1988) *EMBO J.* 7:93–100). Segments with both motifs are most appropriate for binding to class II MHC molecules. $CD8^+$ T cells recognize peptides bound to class I MHC molecules. Parker et al. (1994) *J. Immunol.* 152:163 have determined that peptides binding to particular MHC molecules share discernible sequence motifs. A peptide motif for binding in the groove of HLA-A2.1 has been defined by Edman degradation of peptides stripped from HLA-A2.1 molecules of a cultured cell line (Table 2, from Falk et al. (1991) *Nature* 351:290–296). The method identified the typical or average HLA-A2.1 binding peptide as being 9 amino acids in length with dominant anchor residues occurring at positions 2 (L) and 9 (V). Commonly occurring strong binding residues have been identified at positions 2 (M), 4 (E,K), 6 (V), and 8 (K). The identified motif represents the average of many binding peptides.

TABLE 2

The HLA-A2.1 Restricted Motif

| | Amino Acid Position | | | | | | | | |
|---|---|---|---|---|---|---|---|---|---|
| | 1 | 2 | 3 | 4 | 5 | 6 | 7 | 8 | 9 | Point Assignment |
| Dominant Binding Anchor Residue | | L | | | | | | | V | +3 |
| Strong Binding Residue | | M | | E | | V | | K | | +2 |
| Weak Binding Residue | I | | K | A | I | G | I | A | E | L | +1 |
| | L | Y | P | K | L | Y | S | | |
| | F | F | D | Y | T | H | | | |
| | K | P | T | N | | | | | |
| | M | M | | G | | | | | |
| | Y | S | | V | | | | | |
| | | | | H | | | | | |

The derived peptide motif as currently defined is not particularly stringent. Some HLA-A2.1 binding peptides do not contain both dominant anchor residues and the amino acids flanking the dominant anchor residues play major roles in allowing or disallowing binding. Not every peptide with the current described binding motif will bind, and some peptides without the motif will bind. However, the current motif is valid enough to allow identification of some peptides capable of binding. Of note, all MHC molecules and respective motifs place 6 amino acids between the dominant anchor amino acids at residues 2 and 9.

Following identification of peptide motifs within Her-2/neu ECD-ICD or ECD-PD fusion proteins, amino acid substitutions can be made conservatively or non-conservatively. The latter type of substitutions are intended to produce an improved ECD-ICD or ECD-PD fusion protein or polypeptide that is more potent and/or more broadly cross-reactive. An example of a more potent protein or peptide is one that binds with higher affinity to the same MHC molecule as the natural protein or polypeptide, without affecting recognition by T cells specific for natural protein or polypeptide. An example of a polypeptide with broader cross-reactivity is one that induces more broadly cross-reactive immune responses (i.e., binds to a greater range of MHC molecules) than natural polypeptide. Similarly, one or more amino acids residing between peptide motifs and having a spacer function (e.g., do not interact with a MHC molecule or T cell receptor) can be substituted conservatively or non-conservatively. It will be evident to one of ordinary skill in the art that polypeptides containing one or more amino acid substitutions can be tested for beneficial or adverse immunological interactions by a variety of assays, including those described herein for the ability to stimulate T cell recognition.

Variants within the scope of this invention can also, or alternatively, contain other modifications, including the deletion or addition of amino acids, that have minimal influence on the desired immunological properties of the polypeptide, as described supra. It will be appreciated by one of ordinary skill in the art that truncated forms or non-native extended forms of a Her-2/neu ECD-ICD or ECD-PD fusion protein can be used, provided the desired immunological properties are at least roughly equivalent to that of full length, native Her-2/neu ECD-ICD or ECD-PD fusion protein. Cysteine residues may be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

IV. Preparing the Fusion Proteins of the Invention

A. Polynucleotides Encoding Fusion Proteins

In one embodiment, the present invention relates to isolated or purified polynucleotides that encode the Her-2/neu fusion proteins. In accordance with the invention, any nucleotide sequence which encodes the amino acid sequence of the fusion protein of interest can be used to generate recombinant molecules which direct the expression of the fusion protein.

In order to clone full-length coding sequences or homologous variants to generate the Her-2/neu fusion polynucleotides, labeled DNA probes designed from any portion of the Her-2/neu nucleotide sequences or their complements may be used to screen a genomic or cDNA library, to identify the coding sequence of each individual component of the fusion protein. The Her-2/neu nucleotide sequences can be from any suitable mammal, e.g., human, rat, mouse, horse, cow, pig, sheep, dog, etc.

In one embodiment, the Her-2/neu sequence is from a human, a rat, or a mouse. The nucleotide sequence of the mouse Her-2/neu gene is shown in FIG. 19 (SEQ ID NO:11). Mouse Her-2/neu can also be amplified from mouse brain RNA using the following primers: 5' primer: CCATGGAGCTGGCGGCCTGGTGCCGTTG (SEQ ID NO:12) and 3' primer: GGCCTTCTGGTTCATACTGGCACATCCAGGC (SEQ ID NO:13). The mouse Her-2/neu amino acid sequence is shown in FIG. 20 (SEQ ID NO:14). A variant amino acid sequence for mouse Her-2/neu is described in Nagata et al. (1997) *J. Immunol.* 159:1336–1343.

Such clones may be isolated by screening an appropriate expression library for clones that express a full length Her-2/neu protein. The library preparation and screen may generally be performed using methods known to one of ordinary skill in the art, such as methods described in Sambrook et al., *Molecular Cloning: A Laboratory Manual*, Cold Spring Harbor Laboratories, Cold Spring Harbor, N.Y. (1989). Briefly, a bacteriophage expression library may be plated and transferred to filters. The filters may then be incubated with a detection reagent. In the context of this invention, a "detection reagent" is any compound capable of binding to the Her-2/neu protein, which may then be detected by any of a variety of means known to one of ordinary skill in the art. Typical detection reagents contain a "binding agent," such as Protein A, Protein G, IgG or a lectin, coupled to a reporter group. Preferred reporter groups include enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenz-thiazoline sulfonic acid. Plaques containing genomic or cDNA sequences that express Her-2/neu protein are isolated and purified by techniques known to one of ordinary skill in the art. Appropriate methods may be found, for example, in Sambrook et al., supra.

Isolation of coding sequences may also be carried out by the polymerase chain reaction (PCR) using two degenerate oligonucleotide primer pools designed on the basis of the coding sequences disclosed herein. The desired nucleic acids can also be cloned using other well known amplification techniques. Examples of protocols sufficient to direct persons of skill through in vitro amplification methods, including PCR, ligase chain reaction (LCR), Qβ-replicase amplification and other RNA polymerase mediated techniques are found in Sambrook et al., supra, and Ausubel et al. *Current Protocols in Molecular Biology* (1994), as well as in U.S. Pat. No. 4,683,202; *PCR Protocols A Guide to Methods and Applications* (Innis et al. eds. 1990); Arnheim & Levinson *C&EN* pp. 36–47 (Oct. 1, 1990); *The Journal of NIH Research* 3:81–94 (1991); Kwoh et al. (1989) *Proc. Natl. Acad. Sci. USA* 86:1173; Guatelli et al. (1990) *Proc. Natl. Acad. Sci. USA* 87:1874; Lomell et al. (1989) *J. Clin. Chem.* 35:1826; Landegren et al. (1988) *Science* 241:1077–1080; Van Brunt (1990) *Biotechnology* 8:291–294; Wu et al. (1989) *Gene* 4:560; and Barringer et al. (1990) *Gene* 89:117. Improved methods of cloning in vitro amplified nucleic acids are described in U.S. Pat. No. 5,426,039. Suitable primers for use in the amplification of the nucleic acids of the invention can be designed based on the sequences provided herein.

In accordance with the invention, a polynucleotide of the invention which encodes a fusion protein, fragment thereof, or functional equivalent thereof may be used to generate recombinant nucleic acid molecules that direct the expression of the fusion protein, fragment thereof, or functional equivalent thereof, in appropriate host cells. The fusion polypeptide products encoded by such polynucleotides may be altered by molecular manipulation of the coding sequence.

Due to the inherent degeneracy of the genetic code, other DNA sequences which encode substantially the same or a functionally equivalent amino acid sequence, may be used in the practice of the invention for the expression of the fusion polypeptides. Such DNA sequences include those which are capable of hybridizing to the coding sequences or their complements disclosed herein under low, moderate or high stringency conditions as described herein.

Altered nucleotide sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues, which result in a silent change thus producing a functionally equivalent antigenic epitope. Such conservative amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine and tyrosine; and amino acids with nonpolar head groups include alanine, valine, isoleucine, leucine, phenylalanine, proline, methionine and tryptophan.

The nucleotide sequences of the invention may be engineered in order to alter the fusion protein coding sequence for a variety of ends, including but not limited to, alterations which modify processing and expression of the gene product. For example, mutations may be introduced using techniques which are well known in the art, e.g., to insert or delete restriction sites, to alter glycosylation patterns, phosphorylation, to create and/or destroy translation, initiation, and/or termination sequences, or to create variations in coding regions, to facilitate further in vitro modification, etc. One of skill will recognize many ways of generating alterations in a given nucleic acid construct. Such well-known methods include, e.g., site-directed mutagenesis, PCR amplification using degenerate oligonucleotides, exposure of cells containing the nucleic acid to chemical mutagenic agents or radiation, chemical synthesis of a desired oligonucleotide (e.g., in conjunction with ligation and/or cloning to generate large nucleic acids) and other well-known techniques (see, e.g., Giliman et al. (1979) *Gene* 8:81–97; Hutchinson et al. (1978) *J. Biol. Chem.* 253:6551; Roberts et al. (1987) *Nature* 328: 731–734). Preferably, the manipulations do not destroy immunogenicity of the fusion polypeptides.

In one embodiment of the invention, the coding sequence of a fusion protein may be synthesized in whole or in part, using chemical methods well known in the art (see, e.g., Caruthers et al. (1980) *Nuc. Acids Res. Symp. Ser.* 7:215–233; Crea et al. (1980) *Nuc. Acids Res.* 9(10):2331; Matteucci et al. (1980) *Tetrahedron Letter* 21:719 (1980); and Chow et al. (1981) *Nuc. Acids Res.* 9(12):2807–2817).

B. Polypeptide Synthesis

Alternatively, the fusion polypeptide itself can be produced using chemical methods to synthesize an amino acid sequence in whole or in part. For example, peptides can be synthesized by solid phase techniques such as, e.g., the Merrifield solid phase synthesis method, in which amino acids are sequentially added to a growing chain of amino acids (see, Merrifield (1963) *J. Am. Chem. Soc.* 85:2149–2146). Equipment for automated synthesis of polypeptides is commercially available from suppliers such as Perkin Elmer Biosystems, Inc. (Foster City, Calif.), and may generally be operated according to the manufacturer's instructions. The synthesized peptides can then be cleaved from the resin and purified, e.g., by preparative high performance liquid chromatography (see, Creighton, *Proteins Structures and Molecular Principles*, pp. 50–60 (1983)). The composition of the synthetic fusion polypeptides may be confirmed by amino acid analysis or sequencing (e.g., the Edman degradation procedure; see, Creighton, *Proteins, Structures and Molecular Principles*, pp. 34–49 (1983)).

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

C. Linking Groups

In another embodiment, the polypeptides of the fusion protein, e.g., ECD and ICD or ECD and PD, are joined via a linking group. The linking group can be a chemical crosslinking agent, including, for example, succinimidyl-(N-maleimidomethyl)-cyclohexane-1-carboxylate (SMCC).

The linking group can also be an additional amino acid sequence(s), including, for example, a polyglycine linking group.

In a specific embodiment, the coding sequences of each polypeptide in the fusion protein are directly joined at their amino- or carboxy-terminus via a peptide bond in any order.

Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala, may also be used in the linker sequence. Amino acid sequences which may be usefully employed as linkers include those disclosed in Maratea et al. (1985) *Gene* 40:39–46; Murphy et al. (1986) *Proc. Natl. Acad. Sci. USA* 83:8258–8262; and in U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

Other chemical linkers include carbohydrate linkers, lipid linkers, fatty acid linkers, polyether linkers, e.g., PEG, etc. (see, e.g., Hermanson (1996) *Bioconjugate Techniques*).

D. Additional Polypeptides

As described supra, the fusion protein may be linked to one or more additional polypeptides. For example, the fusion polypeptide may be linked to one or more copies of one of the two polypeptides of the fusion protein. Alternatively, the fusion protein may be linked to an additional heterologous polypeptide, such as, e.g., Ra12 or LeIF, or to a peptide motif such as, e.g., TcP0, as described supra. The fusion polypeptide may also be fused to an affinity tag for ease of purification upon expression. For example, multiple histidine residues encoded by the tag allow the use of metal chelate affinity chromatography methods for the purification of fusion polypeptides. Other examples of affinity tag molecules include, e.g., Strep-tag, PinPoint, maltose binding protein, glutathione S-transferase, etc. (see, e.g., Glick & Pasternak, *Molecular Biotechnology Principles and Applications of Recombinant DNA* ($2^{nd}$ ed. 1999)).

In one embodiment, the fusion polypeptide is optionally linked to a lipid moiety, such as mycolic acid, lipoaribdomanin ("LAMs"), or trehalose derivatives.

As described above, in one embodiment, such a fusion protein is produced by recombinant expression of a nucleic acid encoding the fusion protein. Such a fusion product can be made by ligating the appropriate nucleic acid sequences encoding the desired amino acid sequences to each other by methods known in the art, in the proper coding frame, and expressing the product by methods known in the art. Alternatively, such a product may be made by protein synthetic techniques, e.g., by use of a peptide synthesizer. Coding sequences for other molecules such as a cytokine or an adjuvant can be added to the fusion polynucleotide as well.

E. Sequence Modifications

Variants of the fusion proteins of the invention that retain the ability to stimulate an immune response may generally be identified by modifying the sequence in one or more of the aspects described above and assaying the resulting fusion protein for the ability to stimulate an immune response, e.g., a T cell response or an antibody response. For example, such assays may generally be performed by contacting T cells with the modified fusion protein and assaying the response. Naturally occurring variants of the individual polypeptide components of the fusion protein may also be isolated by, for example, screening an appropriate cDNA or genomic library with a DNA sequence encoding each individual polypeptide or a variant thereof.

The above-described sequence modifications may be introduced using standard recombinant techniques or by automated synthesis of the modified fusion protein. For example, mutations can be introduced at particular loci by synthesizing oligonucleotides containing a mutant sequence, flanked by restriction sites enabling ligation to fragments of the native sequence. Following ligation, the resulting reconstructed sequence encodes an analogue having the desired amino acid insertion, substitution, or deletion.

Alternatively, oligonucleotide-directed site-specific mutagenesis procedures can be used to provide a gene in which particular codons are altered according to the substitution, deletion, or insertion required. Exemplary methods of making the alterations set forth above are described by Walder et al. (1986) *Gene* 42:133; Bauer et al. (1985) *Gene* 37:73; Craik (1985) *BioTechniques* January:12–19; Smith et al. (1981) *Genetic Engineering: Principles and Methods*, Plenum Press; and U.S. Pat. Nos. 4,518,584 and 4,737,462.

Mutations in nucleotide sequences constructed for expression of such Her-2/neu fusion proteins must, of course, preserve the reading frame of the coding sequences and preferably will not create complementary regions that could hybridize to produce secondary mRNA structures, such as loops or hairpins, which would adversely affect the translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed Her-2/neu fusion protein mutants screened for the desired activity. Not all mutations in a nucleotide sequence which encodes a Her-2/neu fusion protein will be expressed in the final product. For example, nucleotide substitutions may be made to enhance expression, primarily to avoid secondary structure loops in the transcribed mRNA (see, e.g., European Patent Application 75,444A), or to provide codons that are more readily translated by the selected host, such as the well-known *E. coli* preference codons for *E. coli* expression.

F. Expression Vectors

The Her-2/neu fusion proteins, and variants thereof, of the present invention, are preferably produced by recombinant DNA methods. Such methods include inserting a DNA sequence encoding a Her-2/neu fusion protein into a recombinant expression vector and expressing the DNA sequence in a recombinant microbial, mammalian, fungal or insect cell expression system under conditions promoting expression and, preferably, secretion of the fusion protein. DNA sequences encoding the Her-2/neu fusion proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors contain a DNA sequence encoding a Her-2/neu fusion protein operably linked to suitable transcriptional or translational regulatory elements derived from mammalian, fungal, microbial, viral or insect genes. Such regulatory elements include a transcriptional promoter, an optional operator sequence to control transcription, a sequence encoding suitable mRNA ribosomal binding sites, and sequences which control the termination of transcription and translation. An origin of replication and a selectable marker to facilitate recognition of transformants may additionally be incorporated.

DNA regions are "operably linked" when they are functionally related to each other. For example, DNA for a signal peptide (secretory leader) is operably linked to DNA for a polypeptide if it is expressed as a precursor which participates in the secretion of the polypeptide; a promoter is "operably linked" to a coding sequence if it controls the transcription of the sequence; or a ribosome binding site is "operably linked" to a coding sequence if it is positioned so as to permit translation. Generally, "operably linked" means contiguous and, in the case of secretory leaders, in reading frame. DNA sequences encoding Her-2/neu fusion proteins which are to be expressed in a microorganism will preferably contain no introns that could prematurely terminate transcription of DNA into mRNA.

Expression vectors for bacterial use may comprise a selectable marker and a bacterial origin of replication derived from commercially available plasmids comprising genetic elements of the well known cloning vector pBR322 (ATCC 37017). Such commercial vectors include, e.g., pKK223-3 (Pharmacia Fine Chemicals, Uppsala, Sweden), pGEMI (Promega Biotec, Madison, Wis.), pET28b (Novagen) and pPDM (a modified pET28b, Corixa). These pBR322 "backbone" sections are combined with an appropriate promoter and the structural sequence to be expressed. *E. coli* is typically transformed using derivatives of pBR322, a plasmid derived from an *E. coli* species (Bolivar et al. (1977) *Gene* 2:95). pBR322 contains genes for ampicillin and tetracycline resistance and thus provides simple means for identifying transformed cells. Promoters commonly used in recombinant microbial expression vectors include the β-lactamase (penicillinase) and lactose promoter system (Chang et al. (1978) *Nature* 275:615; and Goeddel et al. (1979) *Nature* 281:544), the tryptophan (trp) promoter system (Goeddel et al. (1980) *Nucl. Acids Res.* 8:4057; and European Patent Application 36,776) and the tac promoter (Maniatis, *Molecular Cloning: A Laboratory Manual*, Cold Spring Harbor Laboratory, p. 412 (1982)). A particularly useful bacterial expression system uses the phage $\lambda P_L$ promoter and cI857ts thermolabile repressor. Plasmid vectors available from the American Type Culture Collection which incorporate derivatives of the $\lambda P_L$ promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for alcohol oxidase, metallothionein, 3-phosphoglycerate kinase (Hitzeman et al. (1980) *J. Biol. Chem.* 255:2073) or other glycolytic enzymes (Hess et al. (1968) *J. Adv. Enzyme Reg.* 7:149; and Holland et al. (1978) *Biochem.* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in, e.g., European Patent Application No. 73,657.

Preferred yeast vectors can be assembled using DNA sequences from pBR322 for selection and replication in *E. coli* ($Amp^r$ gene and origin of replication) and yeast DNA sequences including a glucose-repressible ADH2 promoter and α-factor secretion leader. The ADH2 promoter has been described by Russell et al. (1982) *J. Biol. Chem,* 258:2674 and Beier et al. (1982) *Nature* 300:724. The yeast α-factor leader, which directs secretion of heterologous proteins, can be inserted between the promoter and the structural gene to be expressed (see, e.g., Kurjan et al. (1982) *Cell* 30:933; and Bitter et al. (1984) *Proc. Natl. Acad. Sci. USA* 81:5330. The leader sequence may be modified to contain, near its 3' end, one or more useful restriction sites to facilitate fusion of the leader sequence to foreign genes.

The transcriptional and translational control sequences in expression vectors to be used in transforming vertebrate cells may be provided by viral sources. For example, commonly used promoters and enhancers are derived, e.g., from polyoma, adenovirus 2, simian virus (SV40), and human cytomegalovirus. DNA sequences derived from the SV40 viral genome, for example, the SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al. (1978) *Nature* 273:113). Smaller or larger SV40 fragments may also be used, provided the approximately 250 bp sequence extending from the Hind III site toward the Bgl II site located in the viral origin of replication is included. Further, viral genomic promoter, control and/or signal sequences may be used, provided such control sequences are compatible with the host cell chosen. Exemplary vectors can be constructed as disclosed by Okayama et al. (1983) *Mol. Cell. Biol.* 3:280.

A useful system for stable high level expression of mammalian receptor cDNAs in C127 murine mammary epithelial cells can be constructed substantially as described by Cosman et al. (1986) *Mol. Immunol.* 23:935. A suitable eukaryotic vector for expression of the fusion proteins of the invention is pDC406 (McMahan et al. (1991) *EMBO J.* 10:2821 which includes regulatory sequences derived from SV40, human immunodeficiency virus (HIV), and Epstein-Barr virus (EBV). Other vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique. Additional suitable mammalian expression vectors include, for example, the pBIB and CR1012 vectors. Any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in mammalian cells are also suitable.

In addition to the transcriptional and translational control sequences, some expression systems have markers that provide gene amplification, such as neomycin, thymidine kinase, hygromycin B phosphotransferase, and dihydrofolate reductase.

A useful cell line that allows for episomal replication of expression vectors, such as pDC406 and pDC409, which contain the EBV origin of replication, is CV-1/EBNA (ATCC CRL 10478). The CV-1/EBNA cell line was derived by transfection of the CV-1 cell line with a gene encoding Epstein-Barr virus nuclear antigen-I (EBNA-1) and constitutively expresses EBNA-1 driven from human CMV immediate-early enhancer/promoter.

Preferred vectors for expression in mammalian cultured cells include pFLAGCMV-1 (Kodak), pcDNA3.1/hyg (Invitrogen), pEE14-GS (CellTech), pBIB and VR1012 (Hartikka et al. (1996) *Hum. Gene Ther.* 7(10):1205–1217).

G. Host Cells

Transformed host cells are cells which have been transformed or transfected with expression vectors constructed using recombinant DNA techniques and which contain sequences encoding Her-2/neu fusion proteins of the present invention. Transformed host cells may express the desired Her-2/neu fusion proteins, but host cells transformed for purposes of cloning or amplifying Her-2/neu DNA do not need to express the Her-2/neu fusion proteins. Expressed Her-2/neu fusion proteins will preferably be secreted into the culture medium or supernatant, depending on the DNA selected. One skilled in the art will appreciate that if Her-2/neu fusion proteins are secreted into the culture supernatant, then they are also soluble in the culture supernatant.

Any of the well known procedures for introducing foreign nucleotide sequences into host cells may be used to introduce the expression vector. These include the use of reagents such as Superfect (Qiagen), liposomes, calcium phosphate transfection, polybrene, protoplast fusion, electroporation, microinjection, plasmid vectors, viral vectors, biolistic particle acceleration (the gene gun), or any of the other well known methods for introducing cloned genomic DNA, cDNA, synthetic DNA or other foreign genetic material into a host cell (see, e.g., Sambrook et al., supra).

Suitable host cells for expression of recombinant proteins include prokaryotes, yeast or higher eukaryotic cells under the control of appropriate promoters. Prokaryotes include gram negative or gram positive organisms, for example *E. coli* or Bacilli. Higher eukaryotic cells include established cell lines of insect or mammalian origin as described below. Cell-free translation systems could also be used to produce Her-2/neu fusion proteins using RNAs derived from DNA constructs. Appropriate cloning and expression vectors for use with bacterial, fungal, yeast, and mammalian cellular hosts are described, for example, by Pouwels et al., *Cloning Vectors: A Laboratory Manual*, Elsevier, NY (1985).

Prokaryotic expression hosts may be used for expression of Her-2/neu fusion proteins that do not require extensive proteolytic and disulfide processing. Prokaryotic expression vectors generally comprise one or more phenotypic selectable markers, e.g., a gene encoding a protein conferring antibiotic resistance or supplying an autotrophic requirement, and an origin of replication recognized by the host to ensure amplification within the host. Suitable prokaryotic hosts for transformation include *E. coli* (e.g., BL21 (DE3) CodonPlus *E. coli*), *Bacillus subtilis*, *Salmonella typhimurium*, and various species within the genera *Pseudomonas, Streptomyces*, and *Staphylococcus*, although other hosts may also be used.

Recombinant Her-2/neu fusion proteins may also be expressed in yeast hosts such as *P. pastoris*. Yeast of other genera, such as *Saccharomyces, Schizosaccharomyces* or *Kluyveromyces*, may also be used. Expression in *Pichia* is achieved by ligation of the gene to be expressed into a bacterial shuttle vector (e.g., the pPICZ series from Invitrogen Co.), transformation of the yeast with this vector and chromosomal integration into the alcohol oxidase (AOX) locus of the yeast genome. Selection for recombinant yeast is then performed using, e.g., Zeocin (Invitrogen Co.) and protein expression is induced by the addition of methanol to the growth medium (Higgin et al., "*Pichia* Protocols," *Methods in Molecular Biology*, Vol. 103, Humana Press (1998)). Suitable strains of *Pichia* for protein expression include, e.g., the SMD1168 *Pichia* strain. Expression systems based on other methodologies, such as the ESP system (Stratagene) may also be used.

Suitable yeast transformation protocols are known to one of skill in the art. An exemplary technique described by Hind et al. (1978) *Proc. Natl. Acad. Sci. USA* 75:1929 involves selecting for Trp$^+$ transformants in a selective medium consisting of 0.67% yeast nitrogen base, 0.5% casamino acids, 2% glucose, 10 mg/ml adenine and 20 mg/ml uracil. Host strains transformed by vectors comprising the ADH2 promoter may be grown for expression in a rich medium consisting of 1% yeast extract, 2% peptone, and 1% glucose supplemented with 80 mg/ml adenine and 80 mg/ml uracil. Derepression of the ADH2 promoter occurs upon exhaustion of medium glucose. Crude yeast supernatants are harvested by filtration and held at 4° C. prior to further purification.

Various mammalian or insect (e.g., *Spodoptera* or *Trichoplusia*) cell culture systems can also be used to express recombinant polypeptides. Baculovirus systems for production of heterologous polypeptides in insect cells are reviewed, for example, by Luckow et al. (1988) *BioTechnology* 6:47. Examples of suitable mammalian host cell lines include the COS-7 lines of monkey kidney cells, described by Gluzman (1981) *Cell* 23:175, and other cell lines capable of expressing an appropriate vector including, e.g., CV-1/EBNA (ATCC CRL 10478), L cells, C127, 3T3, Chinese hamster ovary (CHO), COS, NS-1, HeLa, Human embryonic Kidney Fibroblasts (HEK 293), BHK and HEK293 cell lines. Mammalian expression vectors may comprise non-transcribed elements (e.g., an origin of replication, a suitable promoter and/or an enhancer linked to the gene to be expressed, and other 5' or 3' flanking nontranscribed sequences) and 5' or 3' nontranslated sequences (e.g., necessary ribosome binding sites, a polyadenylation site, splice donor and acceptor sites, and transcriptional termination sequences). Preferred mammalian expression systems are the Chinese hamster ovary (CHO), the HEK293 and the BHK cell lines.

H. Purification of the Fusion Proteins of the Invention

Purified Her-2/neu fusion proteins may be prepared by culturing suitable host/vector systems to express the recombinant translation products of the DNAs of the present invention, which are then purified from culture media or cell extracts. For example, supernatants from systems which secrete recombinant polypeptides into culture media may be first concentrated using a commercially available protein concentration filter, such as, e.g., an Amicon or Millipore Pellicon ultrafiltration unit. Following the concentration step, the concentrate may be applied to a suitable purification matrix. For example, a suitable affinity matrix may comprise a counter structure protein (i.e., a protein to which a Her-2/neu fusion protein binds in a specific interaction based on structure) or lectin or antibody molecule bound to a suitable support.

Alternatively, an anion exchange resin can be used, for example, a matrix or substrate having pendant diethylaminoethyl (DEAE) groups. The matrices can be acrylamide, agarose, dextran, cellulose, polystyrene, sepharose or other types commonly used in protein purification. Alternatively, a cation exchange step can be used. Suitable cation exchangers include various insoluble matrices comprising sulfopropyl or carboxy-methyl groups, preferably sulfopropyl groups. Gel filtration chromatography also provides a means of purifying Her-2/neu fusion proteins. The fusion proteins of the invention are preferably purified by anion exchange chromatography using, e.g., monoQ columns or Q sepharose High Performance chromatography.

Affinity chromatography is another preferred method of purifying Her-2/neu fusion proteins. For example, monoclonal antibodies against the Her-2/neu fusion proteins may be useful in affinity chromatography purification, by using methods that are well-known in the art.

Finally, one or more reverse-phase high performance liquid chromatography (RP-HPLC) steps using hydrophobic RP-HPLC media (e.g., silica gel having pendant methyl or other aliphatic groups) may be used to further purify Her-2/neu fusion protein compositions. Some or all of the foregoing purification steps, in various combinations, can also be used to provide a homogeneous recombinant protein or polypeptide.

Recombinant Her-2/neu fusion proteins produced in bacterial culture may be purified by initial extraction from cell pellets, followed by one or more concentration, salting-out, aqueous ion exchange or size exclusion chromatography steps. High performance liquid chromatography (HPLC) may be used for final purification steps. Microbial cells used in expression of recombinant Her-2/neu fusion proteins can be disrupted by any convenient method, including freeze-thaw cycling, sonication, mechanical disruption, or use of cell lysing agents.

Fermentation of yeast cells which express Her-2/neu fusion proteins as a secreted protein greatly simplifies purification. The secreted recombinant proteins resulting from a large-scale fermentation can be purified by methods analogous to those disclosed by Urdal et al. (1984) *J. Chromatog.* 296:171. This reference describes two sequential, reverse-phase HPLC steps for purification of recombinant human GM-CSF on a preparative HPLC column.

Preparations of Her-2/neu fusion proteins synthesized in recombinant cultures may contain non-Her-2/neu cell components, including proteins, in amounts and of a character which depend upon the purification steps taken to recover the Her-2/neu fusion proteins from the culture. These components are ordinarily of yeast, prokaryotic or non-human eukaryotic origin. Such preparations are typically free of other proteins which may be normally associated with the Her-2/neu protein as it is found in nature in its species of origin.

Automated synthesis provides an alternate method for preparing proteins and polypeptides of this invention. For example, any of the commercially available solid-phase techniques may be used, such as, e.g., the Merrifield solid phase synthesis method, in which amino acids are sequentially added to a growing amino acid chain (see, Merrifield (1963) *J. Am. Chem. Soc.* 85:2149–2146). Equipment for automated synthesis of polypeptides is commercially available from suppliers such as Applied Biosystems, Inc. (Foster City, Calif.), and may generally be operated according to the manufacturer's instructions.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

V. Binding Agents

The present invention further provides agents, such as antibodies and antigen-binding fragments thereof, that specifically bind to a Her-2/neu fusion protein of the invention. As used herein, an antibody, or antigen-binding fragment thereof, is said to "specifically bind" to a Her-2/neu fusion protein if it reacts at a detectable level, i.e., at least two fold over background signal (within, for example, an ELISA) with a Her-2/neu fusion protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ l/mol. The binding constant maybe determined using methods well known in the art.

Binding agents may be further capable of differentiating between patients with and without a cancer, such as breast, ovarian, colon, lung or prostate cancer, using the representative assays provided herein. In other words, antibodies or other binding agents that bind to a Her-2/neu fusion protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, plasma, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art (see, e.g., Harlow and Lane, *Antibodies: A Laboratory Manual*, Cold Spring Harbor Laboratory (1988)). In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising, e.g., a fusion polypeptide or the sequence corresponding to the junction between the individual polypeptides of a fusion protein of interest (referred to as "junction region"), is initially injected into any of a wide variety of mammals (e.g., mice, rats, rabbits, sheep or goats). In this step, the fusion protein of interest or the junction region of the fusion protein of the invention may serve as the immunogen without modification. Alternatively, particularly for relatively short sequences, a superior immune response may be elicited if the sequence is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the fusion polypeptide may then be purified from such antisera by, for example, affinity chromatography using the fusion polypeptide coupled to a suitable solid support.

Polyclonal antibodies raised to a fusion protein of the invention can be selected to obtain only those polyclonal antibodies that are specifically immunoreactive with the fusion protein of interest and not with the individual polypeptide components of the fusion proteins. This selection may be achieved by subtracting out antibodies that cross-react with the individual polypeptide components of the fusion protein of interest.

Alternatively, antibodies that recognize each or all of the individual polypeptide components of a fusion protein may be useful in the context of the present invention.

Monoclonal antibodies specific for an immunogenic fusion polypeptide of interest may be prepared, for example, using the technique of Kohler and Milstein (1976) *Eur. J. Immunol.* 6:511–519, and improvements thereto. Briefly, these methods involve the preparation of immortal cell lines capable of producing antibodies having the desired specificity (i.e., reactivity with the fusion polypeptide of interest). Such cell lines may be produced, e.g., from spleen cells obtained from an animal immunized as described above. The spleen cells are then immortalized by, e.g., fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the fusion polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The fusion polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, supra) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, *Diptheria* toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, including, e.g., U.S. Pat. No. 4,671,958.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and by acid-catalyzed hydrolysis (e.g., U.S. Pat. No. 4,569,789).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as, e.g., albumins (e.g., U.S. Pat. No. 4,507,234), peptides and polysaccharides such as, e.g., aminodextran (e.g., U.S. Pat. No.

4,699,784). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562 discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Examples of available suitable antibodies to the fusion proteins of the invention include, but are not limited to, the 8029K rabbit polyclonal antibody, the mouse monoclonal c-neu-3 antibody (Calbiochem), and the mouse monoclonal HERCEPTIN® Her-2/neu antibody (U.S. Pat. No. 5,677, 171). The monoclonal c-neu-3 antibody recognizes a sequential epitope in the PD domain which is deleted (1242–1255 aa) in the ECD-ΔPD construct. The HERCEPTIN® Her-2/neu antibody binds to a conformational epitope in the ECD domain.

VI. T Cells

Immunotherapeutic compositions may also, or alternatively, comprise T cells specific for a fusion protein of the present invention. Such cells may generally be prepared in vitro or ex vivo, using standard procedures. For example, T cells may be isolated from bone marrow, peripheral blood or a fraction of bone marrow or peripheral blood of a patient, using a commercially available cell separation system (see also, U.S. Pat. Nos. 5,240,856 and 5,215,926; WO 89/06280; WO 91/16116 and WO 92/07243). Alternatively, T cells may be derived from related or unrelated humans, non-human mammals, cell lines or cultures.

T cells may be stimulated with a Her-2/neu fusion polypeptide, a polynucleotide encoding a Her-2/neu fusion protein and/or an antigen presenting cell (APC) that expresses such a fusion polypeptide. Such stimulation is performed under conditions and for a time sufficient to permit the generation of T cells that are specific for the fusion polypeptide. Preferably, a Her-2/neu fusion polypeptide or polynucleotide is present within a delivery vehicle, such as a microsphere, to facilitate the generation of specific T cells.

T cells are considered to be specific for a Her-2/neu fusion polypeptide if the T cells kill target cells coated with the fusion polypeptide or expressing a polynucleotide encoding the fusion polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al. (1994) *Cancer Res.* 54:1065–1070. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a Her-2/neu fusion polypeptide (100 ng/ml-100 µg/ml, preferably 200 ng/ml–25 µg/ml) for 3–7 days should result in at least a two fold increase in proliferation of the T cells. Contact as described above for 2–3 hours should result in the activation of the T cells, as measured using standard cytokine assays in which a two fold increase in the level of cytokine release (e.g., TNF or IFN-γ) is indicative of T cell activation (see, Coligan et al., *Current Protocols in Immunology*, vol. 1, Wiley Interscience, Greene (1998)). T cells that have been activated in response to a Her-2/neu fusion polypeptide, polynucleotide or fusion polypeptide-expressing APC may be CD4$^+$ and/or CD8+. Her-2/neu fusion protein-specific T cells may be expanded using standard techniques. Within preferred embodiments, the T cells are derived from a patient, or from a related or unrelated donor, and are administered to the patient following stimulation and expansion.

For therapeutic purposes, CD4$^+$ or CD8$^+$ T cells that proliferate in response to a Her-2/neu fusion polypeptide, polynucleotide or APC can be expanded in number either in vitro or in vivo. Proliferation of such T cells in vitro may be accomplished in a variety of ways. For example, the T cells can be re-exposed to a Her-2/neu fusion polypeptide with or without the addition of T cell growth factors, such as interleukin-2, and/or stimulator cells that synthesize a Her-2/neu fusion polypeptide. Alternatively, one or more T cells that proliferate in the presence of a Her-2/neu fusion protein can be expanded in number by cloning. Methods for cloning cells are well known in the art, and include limiting dilution. Following expansion, the cells may be administered back to the patient as described, for example, by Chang et al. (1996) *Crit. Rev. Oncol. Hematol.* 22:213.

VII. Pharmaceutical Compositions and Vaccines Comprising Fusion Proteins of the Invention In another preferred embodiment, the present invention is directed to compositions comprising Her-2/neu fusion proteins, or variants thereof, and Her-2/neu ICD proteins, or variants thereof. The fusion proteins are preferably ECD-ICD fusion proteins, ECD-PD fusion proteins, or variants thereof, of the present invention, as described in detail herein. The ICD protein is preferably the human ICD protein, which spans the region from Lys 676 to Val 1255, inclusively, as shown in FIG. 7 (SEQ ID NO:1), or the rat ICD protein, which is the amino acid sequence inclusively spanning Lys 677 to Val 1256 as shown in FIG. 8 (SEQ ID NO:2). Alternatively, the Her-2/neu ICD protein can be any variant or portion of the ICD protein that is immunogenic or that provides enhanced immunogenicity to the composition. For example, the portion of the ICD protein may be the Her-2/neu PD protein, as described herein, the Her-2/neu ΔPD protein, as described herein, the Her-2/neu KD protein, as described herein, or a Her-2/neu ICD protein where anywhere from 1 to 100 amino acids are sequentially removed from the N-terminus or C-terminus of the ICD protein. In addition, amino acid substitutions can generally be made in a variety of ways to provide other embodiments of variants within the present invention. In one embodiment, conservative amino acid substitutions are made, as described supra.

Within certain aspects, polypeptides, polynucleotides, T cells and/or binding agents described herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see, e.g., U.S. Pat. No. 4,235,877). Vaccine preparation is generally described in, for example, Powell and Newman, eds., *Vaccine Design* (the subunit and adjuvant approach), Plenum Press, NY (1995). Vaccines may be designed to generate antibody immunity and/or cellular immunity such as that arising from CTL or $CD4^+$ T cells.

Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine. Polypeptides may, but need not be, conjugated to other macromolecules as described, for example, within U.S. Pat. Nos. 4,372,945 and 4,474,757. Pharmaceutical compositions and vaccines may generally be used for prophylactic and therapeutic purposes.

A pharmaceutical composition or vaccine may contain a polynucleotide encoding one or more of the Her-2/neu fusion proteins, e.g., Her-2/neu ECD-ICD and/or Her-2/neu ECD-PD, as described above, such that the fusion protein is generated in situ. Such a polynucleotide may comprise DNA, RNA, a modified nucleic acid or a DNA/RNA hybrid. As noted above, a polynucleotide may be present within any of a variety of delivery systems known to those of ordinary skill in the art, including nucleic acid expression systems, bacteria and viral expression systems. Numerous gene delivery techniques are well known in the art, such as those described by Rolland (1998) *Crit. Rev. Therap. Drug Carrier Systems* 15:143–198, and references cited therein. Appropriate nucleic acid expression systems contain the necessary DNA sequences for expression in the patient (such as a suitable promoter and terminating signal). Bacterial delivery systems involve the administration of a bacterium (such as *Bacillus* Calmette-Guerin) that expresses an immunogenic portion of the fusion protein on its cell surface or secretes such an epitope.

In a preferred embodiment, the DNA may be introduced using a viral expression system (e.g., vaccinia, pox virus, retrovirus, adenovirus or alphavirus such as SFV), which may involve the use of a part of a virus, of a non-pathogenic (defective), replication competent virus or of a whole virus.

In one illustrative embodiment, retroviruses provide a convenient and effective platform for gene delivery systems. A selected nucleotide sequence encoding a fusion protein of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) *BioTechniques* 7:980–990; Miller (1990) *Human Gene Therapy* 1:5–14; Scarpa et al. (1991) *Virology* 180:849–852; Burns et al. (1993) *Proc. Natl. Acad. Sci. USA* 90:8033–8037; and Boris-Lawrie and Temin (1993) *Curr. Opin. Genet. Develop.* 3:102–109).

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) *J. Virol.* 57:267–274; Bett et al. (1993) *J. Virol.* 67:5911–5921; Mittereder et al. (1994) *Human Gene Therapy* 5:717–729; Seth et al. (1994) *J. Virol.* 68:933–940; Barr et al. (1994) *Gene Therapy* 1:51–58; Berkner (1988) *BioTechniques* 6:616–629; and Rich et al. (1993) *Human Gene Therapy* 4:461–476).

Various adeno-associated virus (AAV) vector systems have also been developed for polynucleotide delivery. AAV vectors can be readily constructed using techniques well known in the art (see, e.g., U.S. Pat. Nos. 5,173,414 and 5,139,941; PCT Publication Nos. WO 92/01070 and WO 93/03769; Lebkowski et al. (1988) *Mol. Cell. Biol.* 8:3988–3996; Vincent et al. (1990) *Vaccines* 90 (Cold Spring Harbor Laboratory Press); Carter (1992) *Current Opinion in Biotechnology* 3:533–539; Muzyczka (1992) *Current Topics in Microbiol. and Immunol.* 158:97–129; Kotin (1994) *Human Gene Therapy* 5:793–801; Shelling and Smith (1994) *Gene Therapy* 1:165–169; and Zhou et al. (1994) *J. Exp. Med.* 179:1867–1875).

Additional viral vectors useful for delivering the nucleic acid molecules encoding fusion proteins of the present invention by gene transfer include those derived from the pox family of viruses, such as vaccinia virus and avian poxvirus. By way of example, vaccinia virus recombinants expressing the novel molecules can be constructed as follows. The DNA encoding a fusion protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the fusion protein of interest into the viral genome. The resulting TK.sup.(-) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more fusion proteins described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products (see, e.g., Elroy-Stein and Moss (1990) *Proc. Natl. Acad. Sci. USA* 87:6743–6747; Fuerst et al. (1986) *Proc. Natl. Acad. Sci. USA* 83:8122–8126).

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses (see, e.g., WO 91/12882; WO 89/03429; and WO 92/03545).

Any of a number of alphavirus vectors (e.g., Semliki Forest Virus) can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. (1993) *J. Biol. Chem.* 268:6866–6869 and Wagner et al. (1992) *Proc. Natl. Acad. Sci. USA* 89:6099–6103, can also be used for gene delivery under the invention.

Additional illustrative information on these and other known viral-based delivery systems can be found, for example, in Fisher-Hoch et al. (1989) *Proc. Natl. Acad. Sci. USA* 86:317–321; Flexner et al. (1989) *Ann. N.Y. Acad. Sci.* 569:86–103; Flexner et al. (1990) *Vaccine* 8:17–21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner (1988) *Biotechniques* 6:616–627; Rosenfeld et al. (1991) *Science* 252:431–434; Kolls et al. (1994) *Proc. Natl. Acad. Sci. USA* 91:215–219; Kass-Eisler et al. (1993) *Proc. Natl. Acad. Sci. USA* 90:11498–11502; Guzman et al. (1993) *Circulation* 88:2838–2848; and Guzman et al. (1993) *Cir. Res.* 73:1202–1207.

Techniques for incorporating DNA into such expression systems are well known to those of ordinary skill in the art. The DNA may also be "naked," as described, for example, in Ulmer et al. (1993) *Science* 259:1745–1749 and reviewed by Cohen (1993) *Science* 259:1691–1692. The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

It will be apparent that a vaccine may contain pharmaceutically acceptable salts of the polynucleotides and fusion polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883. The Her-2/neu fusion protein may be encapsulated within the biodegradable microsphere or associated with the surface of the microsphere. In one embodiment, an ECD-ICD fusion protein described herein is encapsulated within a biodegradable microsphere. Alternatively or in addition, an ECD-PD fusion protein described herein is encapsulated within a biodegradable microsphere. The microsphere can comprise, e.g., both an ECD-ICD fusion protein and an ECD-PD fusion protein. Preferably the microsphere be less than about 25 µm, preferably about 1 µm to about 10 µm. Encapsulation in liposomes is described, e.g., in U.S. Pat. No. 4,235,877.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immune response enhancers or immunostimulatory substances may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and variants thereof (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition can be designed to induce, e.g., an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see, Mosmann and Coffinan (1989) *Ann. Rev. Immunol.* 7:145–173.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see, U.S. Pat. Nos. 4,436,727; 4,877,611; 4,866,034; and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al. (1996) *Science* 273: 352. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2, SBAS-4 or SBAS-6 or variants thereof, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720.

In a preferred embodiment, the adjuvant is SBAS-2 or SBAS-4 (see, e.g., EP 735898B1).

Any vaccine provided herein may be prepared using well known methods that result in a combination of antigen, immune response enhancer and a suitable carrier or excipient. The compositions described herein may be administered as part of a sustained release formulation (i.e., a formulation such as a capsule or sponge that effects a slow release of compound following administration). Such formulations may generally be prepared using well known technology (see, e.g., Coombes et al. (1996) *Vaccine* 14:1429–1438) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly (lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254; and PCT applications WO 94/20078; WO/94/23701; and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau et al. (1998) *Nature* 392:245–251) and have been shown to be effective as a physiological adjuvant for eliciting prophylactic or therapeutic antitumor immunity (see, Timmerman et al. (1999) *Ann. Rev. Med.* 50:507–529). In general, dendritic cells may be identified based on their typical shape (stellate in situ, with marked cytoplasmic processes (dendrites) visible in vitro), their ability to take up, process and present antigens with high efficiency, and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see, Zitvogel et al. (1998) *Nature Med.* 4:594–600).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APCs with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a fusion protein of the invention (or variant thereof) such that the fusion protein, or a variant thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al. (1997) *Immunology and cell Biology* 75:456–460. Antigen loading of dendritic cells may be achieved by incubating dendritic cells or progenitor cells with the fusion protein of interest, DNA (naked or within a plasmid vector) or RNA; or with fusion protein-expressing recombinant bacteria or viruses (e.g., vaccinia, fowlpox, adenovirus or lentivirus vectors). Prior to loading, the fusion protein of interest may be covalently conjugated to an immunological partner that provides T cell help (e.g., a carrier molecule). Alternatively, a dendritic cell may be pulsed with a non-conjugated immunological partner, separately or in the presence of the fusion protein.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

It will be evident to one skilled in the art that a Her-2/neu fusion protein or nucleic acid for a vaccine may be prepared synthetically or may be naturally derived.

VIII. Immune Response to Fusion Proteins of the Invention

A. Detection of an Immune Response to Fusion Proteins of the Invention

In one aspect of the invention, Her-2/neu fusion proteins (or polynucleotides that encode Her-2/neu fusion proteins) are used to generate an immune response to the Her-2/neu protein, including that expressed in a malignancy in which a Her-2/neu oncogene is associated. Representative examples of such malignancies include breast, ovarian, colon, lung and prostate cancers. An immune response to the Her-2/neu protein, once generated by Her-2/neu fusion proteins, can be long-lived and can be detected long after immunization, regardless of whether the protein is present or absent in the body at the time of testing. An immune response to the Her-2/neu protein generated by reaction to a Her-2/neu fusion protein can be detected by examining for the presence or absence, or enhancement, of specific activation of $CD4^+$ or $CD8^+$ T cells or by antibodies. For instance, T cells isolated from an immunized individual by routine techniques (e.g., by Ficoll/Hypaque density gradient centrifugation of peripheral blood lymphocytes) are incubated with a Her-2/neu fusion protein. For example, T cells may be incubated in vitro for 2–9 days (typically 4 days) at 37° C. with a Her-2/neu fusion protein (typically, 5 μg/ml of whole protein or graded numbers of cells synthesizing Her-2/neu protein). It may be desirable to incubate another aliquot of a T cell sample in the absence of Her-2/neu fusion protein to serve as a control.

Specific activation of $CD4^+$ or $CD8^+$ T cells may be detected in a variety of ways. Methods for detecting specific T cell activation include, but are not limited to, detecting the proliferation of T cells, the production of cytokines (e.g., lymphokines), or the generation of cytolytic activity (i.e., generation of cytotoxic T cells specific for a Her-2/neu fusion protein). For $CD4^+$ T cells, a preferred method for detecting specific T cell activation is the detection of the proliferation of T cells. For $CD8^+$ T cells, a preferred method for detecting specific T cell activation is the detection of the generation of cytolytic activity.

Detection of the proliferation of T cells may be accomplished by a variety of known techniques. For example, T cell proliferation can be detected by measuring the rate of DNA synthesis. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyltetrazolium. Alternatively, synthesis of lymphokines (e.g., interferon-gamma) can be measured or the relative number of T cells that can respond to intact $p185^{Her-2/neu}$ protein may be quantified.

B. Detection of Antibody Production in Response to Fusion Proteins of the Invention The present invention is also directed to Her-2/neu fusion proteins that, in addition to being immunogenic to T cells, appear to stimulate B-cells to produce antibodies capable of recognizing Her-2/neu fusion proteins. Detection of such antibodies provides another way to diagnose a malignancy in which a Her-2/neu oncogene is associated with the malignancy. Antibodies specific (i.e., which exhibit a binding affinity of about $10^7$ l/mole or better) for Her-2/neu fusion proteins may be found in a variety of body fluids including sera and ascites. Briefly, a body fluid sample is isolated from a warm-blooded animal, such as a human, for whom it is desired to determine whether antibodies specific for the fusion proteins are present. The body fluid is incubated with Her-2/neu fusion proteins under conditions and for a time sufficient to permit immunocomplexes to form between the Her-2/neu fusion proteins and antibodies specific for the fusion proteins. For example, a body fluid and Her-2/neu fusion proteins may be incubated at 46° C. for 24–48 hours. Following the incubation, the reaction mixture is tested for the presence of immunocomplexes. Detection of one or more immunocomplexes formed between Her-2/neu fusion protein and antibodies specific for Her-2/neu fusion protein may be accomplished by a variety of known techniques, such as radioimmunoassays (RIA) and enzyme linked immunosorbent assays (ELISA).

Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "western blot" method of Gordon et al. (U.S. Pat. No. 4,452,901); immunoprecipitation of labeled ligand (Brown et al. (1980) *J. Biol. Chem.* 255:4980–4983); enzyme-linked immunosorbent assays (ELISA) as described, for example, by Raines et al. (1982) *J. Biol. Chem.* 257:5154–5160; immunocytochemical techniques, including the use of fluorochromes (Brooks et al. (1980) *Clin. Exp. Immunol.* 39:477); and neutralization of activity (Bowen-Pope et al. (1984) *Proc. Natl. Acad. Sci. USA* 81:2396–2400). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

For detection purposes, Her-2/neu fusion proteins (i.e., antigens) may either be labeled or unlabeled. When unlabeled, fusion proteins find use in agglutination assays. In addition, unlabeled fusion proteins can be used in combination with labeled molecules that are reactive with immunocomplexes, or in combination with labeled antibodies (second antibodies) that are reactive with the antibody directed against Her-2/neu fusion protein, such as antibodies specific for immunoglobulin. Alternatively, the fusion protein can be directly labeled. Where it is labeled, the reporter group can include, e.g., radioisotopes, fluorophores, enzymes, luminescers, dye particles and the like. These and other labels are well known in the art and are described, for example, in U.S. Pat. Nos. 3,766,162; 3,791,932; 3,817,837; 3,996,345; and 4,233,402.

Typically in an ELISA, the fusion protein of interest is adsorbed to the surface of a microtiter well. Residual protein-binding sites on the surface are then blocked with an appropriate agent, such as bovine serum albumin (BSA), heat-inactivated normal goat serum (NGS), or BLOTTO (buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1%–5.0% by weight) of protein, such as BSA, NGS, or BLOTTO. After incubating for a sufficient length of time to allow specific binding to occur, the well is washed to remove unbound protein and then incubated with an anti-species specific immunoglobulin antibody labeled with a reporter group. The reporter group can be chosen from a variety of enzymes, including, e.g., horseradish peroxidase, beta-galactosidase, alkaline phosphatase, and glucose oxidase. Sufficient time is allowed for specific binding to occur, then the well is again washed to remove unbound conjugate, and the substrate for the enzyme is added. Color is allowed to develop and the optical density of the contents of the well is determined visually or instrumentally.

In one preferred embodiment of this aspect of the present invention, a reporter group is bound to the Her-2/neu fusion protein of interest. The step of detecting immunocomplexes involves removing substantially any unbound Her-2/neu fusion protein and then detecting the presence or absence of the reporter group.

In another preferred embodiment, a reporter group is bound to a second antibody capable of binding to the antibodies specific for Her-2/neu fusion proteins. The step of detecting immunocomplexes involves (a) removing substantially any unbound antibody, (b) adding the second antibody, (c) removing substantially any unbound second antibody and then (d) detecting the presence or absence of the reporter group. Where the antibody specific for the Her-2/neu fusion protein of interest is derived from a human, the second antibody is an anti-human antibody.

In a third preferred embodiment for detecting immunocomplexes, a reporter group is bound to a molecule capable of binding to the immunocomplexes. The step of detecting involves (a) adding the molecule, (b) removing substantially any unbound molecule, and then (c) detecting the presence or absence of the reporter group. An example of a molecule capable of binding to the immunocomplexes is protein A.

It will be evident to one skilled in the art that a variety of methods for detecting the immunocomplexes may be used within the present invention. Reporter groups suitable for use in any of the methods include, e.g., radioisotopes, fluorophores, enzymes, luminescers, and dye particles.

In a related aspect of the present invention, detection of immunocomplexes formed between Her-2/neu fusion proteins and antibodies in body fluid which are specific for Her-2/neu fusion proteins may be used to monitor the effectiveness of cancer therapy, which involves a Her-2/neu fusion protein, for a malignancy in which the Her-2/neu oncogene is associated. Samples of body fluid taken from an individual prior to and subsequent to initiation of therapy may be analyzed for the immunocomplexes by the methodologies described above. Briefly, the number of immunocomplexes detected in both samples are compared. A substantial change in the number of immunocomplexes in the second sample (post-therapy initiation) relative to the first sample (pre-therapy) reflects successful therapy.

IX. Cancer Therapy

In further aspects of the present invention, the compositions described herein may be used for immunotherapy of cancer, such as breast, ovarian, colon, lung and prostate cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs. Administration may be by any suitable method, including administration by intravenous, intraperitoneal, intramuscular, subcutaneous, intranasal, intradermal, anal, vaginal, topical, sublingual and oral routes.

Within certain embodiments, immunotherapy may be active immunotherapy, in which treatment relies on the in vivo stimulation of the endogenous host immune system to react against tumors with the administration of immune response-modifying agents (such as fusion polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed supra, T lymphocytes (such as CD8$^+$ cytotoxic T lymphocytes and CD4$^+$ T-helper tumor-infiltrating lymphocytes), killer cells (such as Natural Killer cells and lymphokine-activated killer cells), B cells and antigen-presenting cells (such as dendritic cells and macrophages) expressing a fusion protein provided herein. T cell receptors and antibody receptors specific for the fusion polypeptides recited herein may be cloned, expressed and transferred into other vectors or effector cells for adoptive immunotherapy. The fusion polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive fusion polypeptides as provided herein may be used to rapidly expand antigen-specific T cell cultures in order to generate a sufficient number of cells for immunotherapy. In particular, antigen-presenting cells, such as dendritic, macrophage or B cells, may be pulsed with immunoreactive fusion polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al. (1997) *Immunological Reviews* 157:177).

Alternatively, a vector expressing a fusion polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more fusion polypeptides, the amount of each fusion protein present in a dose ranges from about 1 µg to 5 mg, preferably 100 µg to 5 mg, and most preferably 5 µg to 250 µg per kg of host. Suitable dose sizes will vary with the size of the patient, but will typically range from about 0.1 ml to about 5 ml.

Preferably, an initial or primary immunization will be made with a Her-2/neu fusion protein having, e.g., at least one of an ECD and/or a ICD or PD, and a subsequent or booster immunization will be made with a Her-2/neu fusion protein having, e.g., at least one of a ECD and/or a ICD or PD. Preferred ECD-ICD and/or ECD-PD fusion proteins for immunization include those described herein. It will be appreciated by one skilled in the art that the present invention contemplates the use of an intact Her-2/neu fusion protein as well as division of the Her-2/neu fusion protein into a plurality of peptides. In addition, variants of the entire Her-2/neu protein, such as, e.g., the Delta Her-2/Neu protein (e.g., the mouse Delta Her-2/neu protein) described herein can also be used for immunization in the context of the present invention. Neither intact human p185$^{Her-2/Neu}$ protein nor a peptide having the amino acid sequence of the entire Her-2/neu ECD domain (or a portion of the Her-2/neu ECD domain) are used alone for immunization.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a Her-2/neu protein or fusion protein generally correlate with an improved clinical outcome. Such immune responses may generally be evaluated using standard proliferation, cytotoxicity or cytokine assays, which may be performed using samples obtained from a patient before and after treatment.

X. Detecting Cancer

A. Methods of Detecting Cancer

In general, a cancer may be detected in a patient based on the presence of Her-2/neu proteins and/or polynucleotides encoding such proteins in a biological sample (such as blood, sera, plasma, urine and/or tumor biopsies) obtained from the patient. In other words, such proteins may be used as markers to indicate the presence or absence of a cancer such as, e.g., breast, ovarian, colon, lung, prostate cancer, etc. The binding agents provided herein generally permit detection of the level of Her-2/neu protein that binds to the agent in the biological sample. Polynucleotide primers and probes may be used to detect the level of mRNA encoding a Her-2/neu tumor protein, which is also indicative of the presence or absence of a cancer. In general, a Her-2/neu tumor sequence should be present at a level that is at least three fold higher in tumor tissue than in normal tissue.

There are a variety of assay formats known to those of ordinary skill in the art for using a binding agent to detect polypeptide markers in a sample (see, e.g., Harlow and Lane, supra). In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of a binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent.

Suitable polypeptides for use within such assays include full length Her-2/neu tumor proteins and portions thereof to which the binding agent binds, and Her-2/neu fusion proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of a binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast, ovarian, colon, lung or prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast, ovarian, colon, lung or prostate cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins, or binding agents of the present invention. The above descriptions are intended to be exemplary only. For example, it will be apparent to those of ordinary skill in the art that the above protocols may be readily modified to use Her-2/neu polypeptides to detect antibodies that bind to such polypeptides in a biological sample. The detection of such Her-2/neu protein specific antibodies may correlate with the presence of a cancer.

A cancer may also, or alternatively, be detected based on the presence of T cells that specifically react with a Her-2/neu fusion protein in a biological sample. Within certain methods, a biological sample comprising $CD4^+$ and/or $CD8^+$ T cells isolated from a patient is incubated with a Her-2/neu fusion polypeptide, a polynucleotide encoding such a fusion polypeptide and/or an APC that expresses at least such fusion polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with a Her-2/neu fusion polypeptide (e.g., 5–25 µg/ml). It may be desirable to incubate another aliquot of a T cell sample in the absence of Her-2/neu fusion polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a Her-2/neu protein in a biological sample. For example, at least two oligonucleotide primers may be employed in a polymerase chain reaction (PCR) based assay to amplify a portion of a Her-2/neu cDNA derived from a biological sample, wherein at least one of the oligonucleotide primers is specific for (i.e., hybridizes to) a polynucleotide encoding the Her-2/neu protein. The amplified cDNA is then separated and detected using techniques well known in the art, such as gel electrophoresis. Similarly, oligonucleotide probes that specifically hybridize to a polynucleotide encoding a Her-2/neu protein or fusion protein may be used in a hybridization assay to detect the presence of a polynucleotide encoding the Her-2/neu protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a Her-2/neu protein, or fusion protein, that is at least 10 nucleotides, and preferably at least 20 nucleotides, in length. Preferably, oligonucleotide primers and/or probes hybridize to a polynucleotide encoding a Her-2/neu protein or fusion protein described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited SEQ ID NO:9, 10 or 11. Techniques for both PCR based assays and hybridization assays are well known in the art (see, for example, Mullis et al. (1987) *Cold Spring Harbor Symp. Quant. Biol.* 51:263; Erlich ed., *PCR Technology*, Stockton Press, NY (1989)).

One preferred assay employs RT-PCR, in which PCR is applied in conjunction with reverse transcription. Typically, RNA is extracted from a biological sample such as a biopsy tissue and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, Her-2/neu proteins or fusion proteins and polynucleotides encoding such proteins or fusion proteins may be used as markers for monitoring the progression of cancer. In this embodiment, assays as described above for the diagnosis of a cancer may be performed over time, and the change in the level of reactive polypeptide(s) evaluated. For example, the assays may be performed every 24–72 hours for a period of 6 months to 1 year, and thereafter performed as needed. In general, a cancer is progressing in those patients in whom the level of polypeptide detected by the binding agent increases over time. In contrast, the cancer is not progressing when the level of reactive polypeptide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple Her-2/neu fusion protein markers may be assayed within a given sample. It will be apparent that binding agents specific for different proteins provided herein may be combined within a single assay. Further, multiple primers or probes may be used concurrently. The selection of tumor protein markers may be based on routine experiments to determine which combinations result in optimal sensitivity. In addition, or alternatively, assays for tumor proteins provided herein may be combined with assays for other known tumor antigens.

B. Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a Her-2/neu fusion protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a Her-2/neu protein in a biological sample. Such kits generally comprise at least one oligonucleotide probe or primer, as described above, that hybridizes to a polynucleotide encoding a Her-2/neu protein or fusion protein. Such an oligonucleotide may be used, for example, within a PCR or hybridization assay. Additional components that may be present within such kits include a second oligonucleotide and/or a diagnostic reagent or container to facilitate the detection of a polynucleotide encoding a Her-2/neu protein.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

XI. Examples

In the examples, general molecular biology reagents, such as oligonucleotide primers, lipofectamine and restriction endonucleases, were primarily obtained from Gibco/BRL (Grand Island, N.Y.). Restriction endonucleases, Aat II and PflM-I were obtained from New England Biolabs (Beverly, Mass.). The Her-2/neu ELISA assay kit and Her-2/neu specific monoclonal antibody Ab-3 were purchased from Oncogene Science (Manhasset, N.Y.). The pFLAGCMV-1 expression vector and FLAG-Tag M2 antibody were purchased from Kodak (Rochester, N.Y.). Pfu polymerase was obtained from Stratagene (La Jolla, Calif.). The pcDNA3.1/hyg expression vector was purchased from Invitrogen (Carlsbad, Calif.).

Example 1

Figure 2:
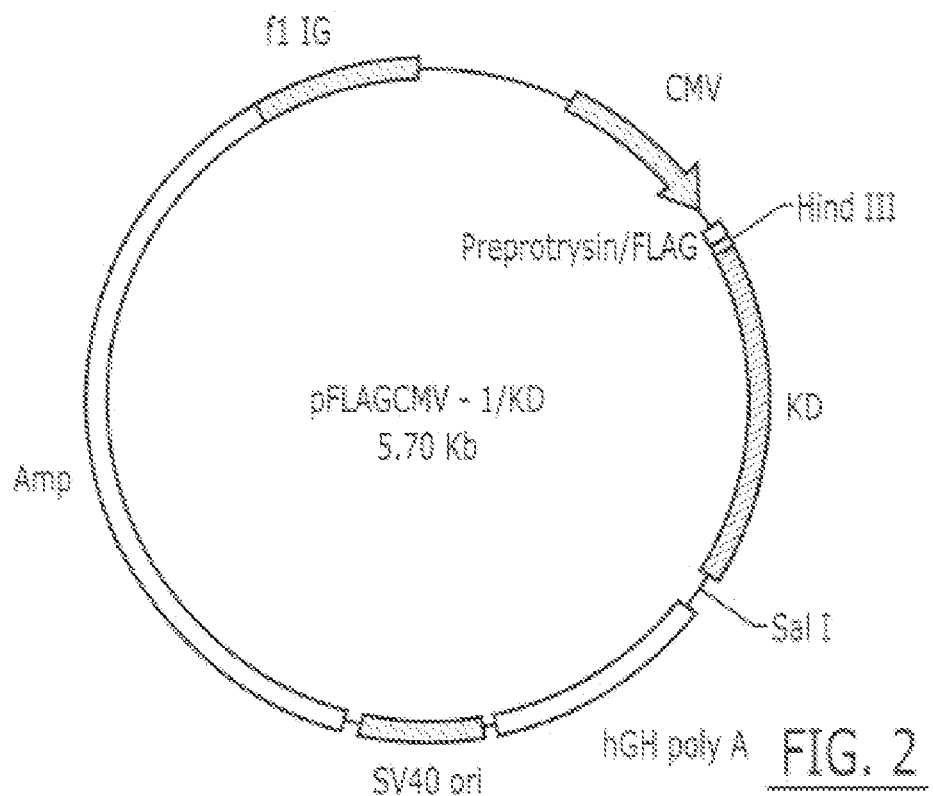
FIG. 2 shows a map of the pFLAGCMV-1/KD expression plasmid, which has a size of 5.7 kb.
Figure 3:
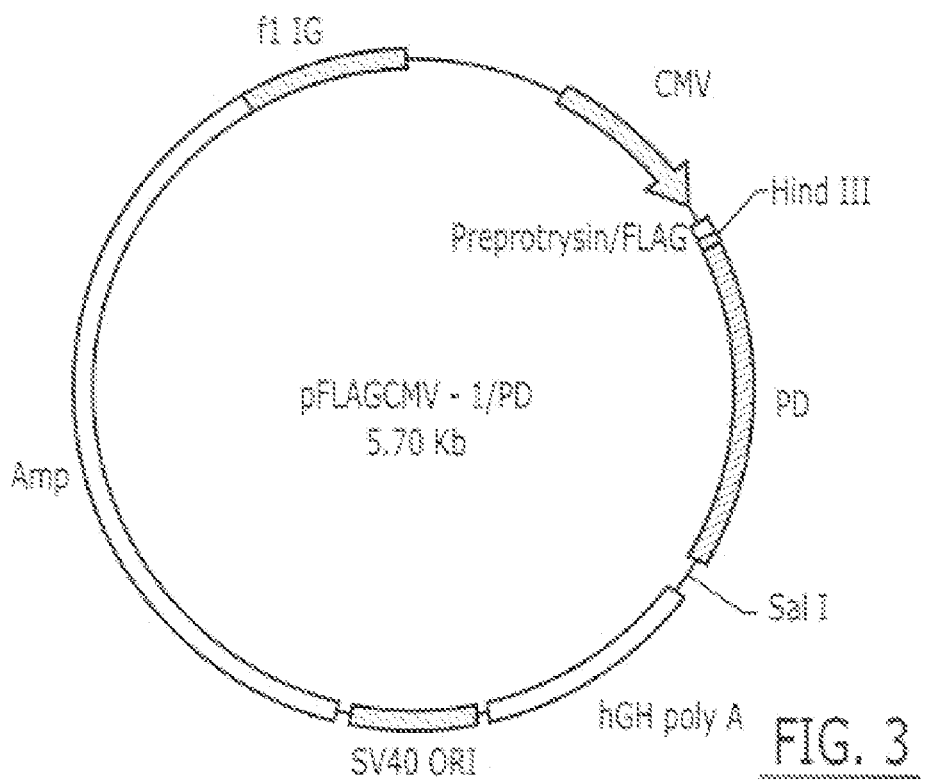
FIG. 3 shows a map of the pFLAGCMV-1/PD expression plasmid, which has a size of 5.7 kb.

Cloning of the ICD, KD and PD Fragments of HER-2/NEU into the pFLAGCMV-1 Expression Vector The DNA fragments of Her-2/neu that encode the intracellular domain (ICD), kinase domain (KD) and phosphorylation domain (PD) were obtained separately by polymerase chain reaction. Restriction digestion sites, Hind III and Xho I, were introduced at their 5' and 3' end respectively. This design allowed the cloning of the DNA fragments into the pFLAGCMV-1 expression vector (Kodak) in frame with a preprotrypsin leader sequence and a FLAG-Tag sequence at their N-terminus. The PCR products were gel purified and cloned into the Hind III and Sal I sites of pFLAGCMV-1. The resulting expression plasmids were designated as pFLAGCMV-V-1/ICD (FIG. 1), pFLAGCMV-1/KD (FIG. 2) and pFLAGCMV-1/PD (FIG. 3).

Example 2

Cloning of the ECD-PD Fusion Protein into the pcDNA3.1/hyg Expression Vector

Figure 5:
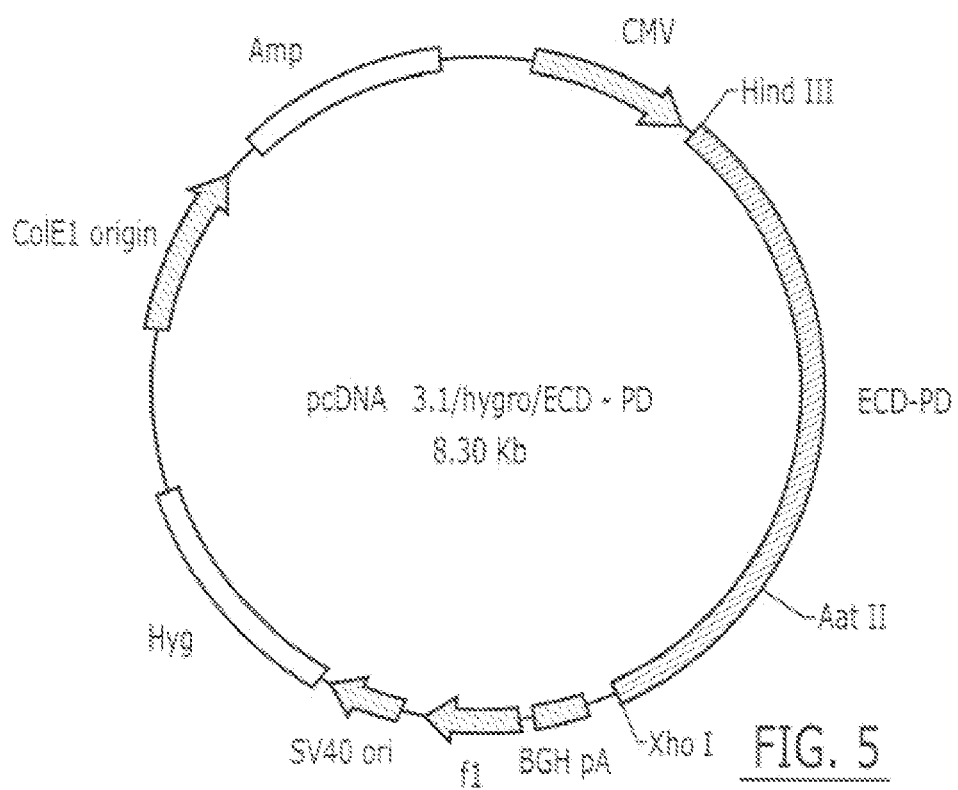
FIG. 5 shows a map of the pcDNA3.1/hygro/ECD-PD expression vector, which has a size of 8.3 kb.

The DNA fragment encoding the Her-2/neu PD was amplified by polymerase chain reaction. After gel purification, it was cloned into the Aat II and Xho I sites of the pT7-Her-2/neu plasmid. This procedure generated a new cloning vector, pT7/ECD-PD which linked the ECD and PD together (including a Ser from the transmembrane domain). The pT7/ECD-PD plasmid was digested with Hind III and Xho I at 37° C. for 1 hour. The 2.7 kb DNA fragment encoding the ECD-PD fusion protein was gel purified and subcloned into the Hind III and Xho I sites of pcDNA3.1/hyg (Invitrogen). The resulting expression vector was designated as pcDNA3.1/hyg/ECD-PD (FIG. 5).

Example 3

Expression of the ICD, KD and PD Fragments of HER-2/NEU in HEK-293 Cells

The pFLAGCMV-1 expression plasmid (Kodak) was used to determine which region of the Her-2/neu intracellular domain could be secreted in culture media. The proteins were expressed as fusions with a preprotrypsin secretion signal and a FLAG-Tag at their N-terminus, as described in Example 1.

Transfection and growth of ICD, KD and PD expressing cell lines was conducted as follows: human embryonic kidney fibroblasts (HEK-293 cells) were grown in Dulbecco's modified Eagle's medium containing 10% fetal calf serum. One day prior to transfection, $1.5 \times 10^5$ cells were seeded into each well of a six-well dish. Transfection was carried out using 1 μg of plasmid DNA by lipofectamine (Gibco/BRL) in serum free media. Culture media and cells were harvested 72 hours later. For selection of stable transformants, the transfected cells were grown in media containing 200 μg/ml hygromycin.

Cells and culture media were assayed for FLAG-Tag fusion proteins by Western blot analysis as follows: culture media and cell lysates from transfected HEK-293 cells were separated on 7.5% SDS polyacrylamide gel. The proteins were transferred electrophoretically to polyvinylidene difluoride (PVDF) filters. The PVDF filters were first incubated with 5% bovine serum albumin in TBST (20 mM Tris, pH 7.5, 150 mM NaCl, 0.01% Tween 20), then incubated for 1 hour with the primary antibody, and finally incubated for another hour with peroxidase-conjugated goat anti-mouse antibody. Immunoblots were developed using ECL system (Amersham Corp.). The mouse monoclonal antibody, c-neu Ab-3 ("Ab-3") (Oncogene Science), was used for detecting the Her-2/neu protein. Ab-3 recognizes the carboxyl terminal of the human Her-2/neu protein. For detecting FLAG-Tag fusion proteins, the M2 monoclonal antibody (Kodak) was used as primary antibody in the analysis.

Figure 4:
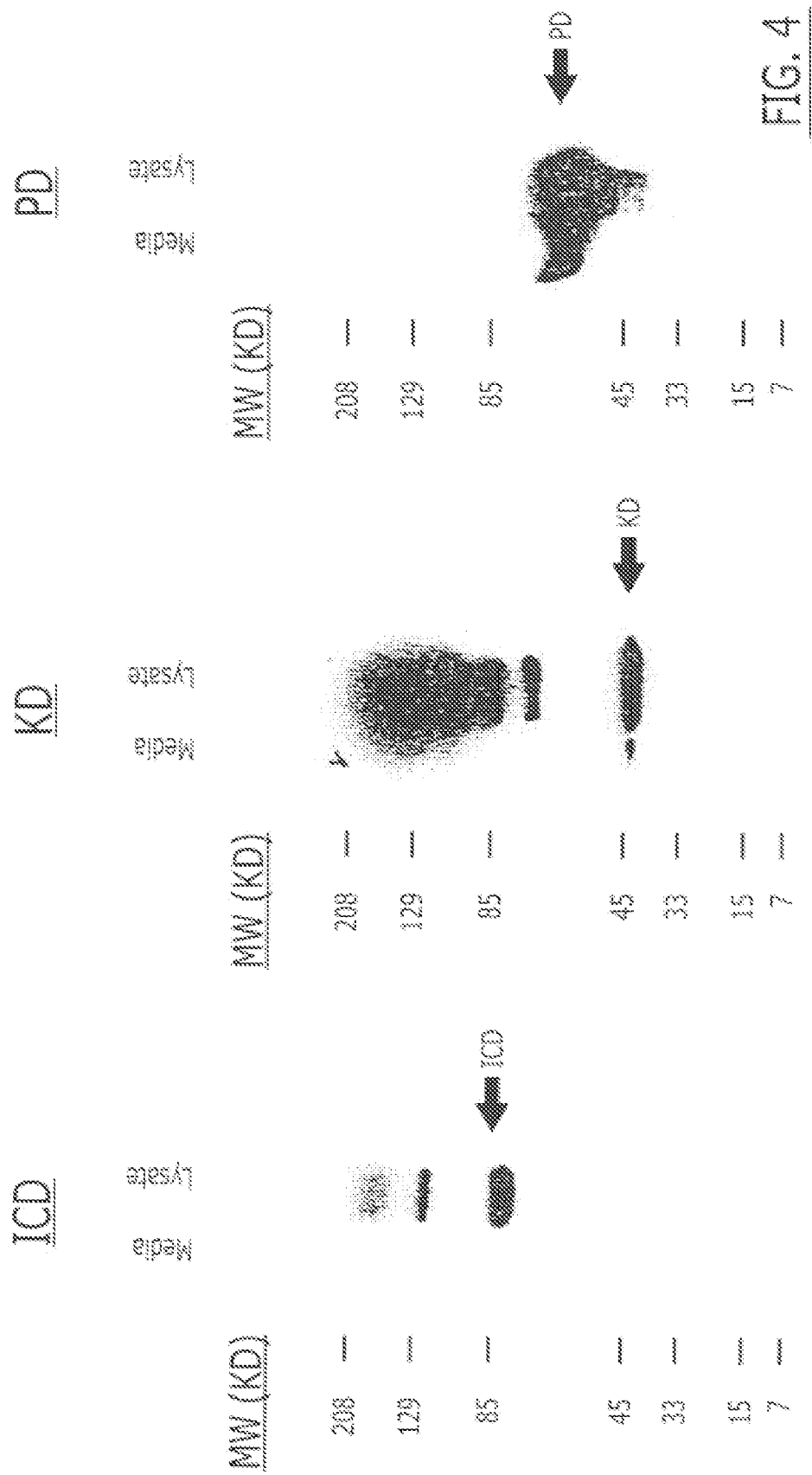
FIG. 4 shows that the Her-2/neu phosphorylation domain was secreted into the culture media, and that the Her-2/neu intracellular domain and Her-2/neu kinase domain were not secreted into the culture media, as described in Example 3.

The results presented in FIG. 4 show that neither full length ICD nor KD were secreted, but that PD was detected in the culture media. The results indicate that the structure of KD did not permit passage of the protein through the cell membrane.

Example 4

Expression of the ECD-PD Fusion Protein in HEK-293 and CHO Cells Using the pcDNA3.1/hyg Expression Vector The ECD-PD fusion protein with a preprotrypsin secretion signal and FLAG-Tag at its N-terminus was constructed, as described in Example 2.

Transfection and growth of ECD-PD expressing cell lines was conducted as follows: HEK-293 cells and Chinese hamster ovary cells (CHO) were grown in Dulbecco's modified Eagle's medium containing 10% fetal calf serum. One day prior to transfection, $1.5 \times 10^5$ cells were seeded into each well of a six-well dish. Transfection was carried out using 1 µg of plasmid DNA by lipofectamine (Gibco/BRL) in serum free media. Culture media and cells were harvested 72 hour later. For selection of stable transformants, the transfected cells were grown in media containing 200 µg/ml hygromycin.

The secretion of the soluble ECD-PD fusion protein was determined by an ELISA assay with Her-2/neu ECD specific antibodies as follows: the microplate was pre-coated with the Her-2/neu specific mouse antibody (Oncogene Science) to capture Her-2/neu protein in the samples. Test samples were incubated in the microplate overnight at room temperature, incubated for 1 hour with detector antibody, and incubated for another hour with a horseradish peroxidase-conjugated goat anti-rabbit antibody. After adding the peroxidase substrate o-phenylenediamine, a colored product was formed. The colored product was quantitated by spectrophotometry. Absorbance at 490 nm reflected the amount of Her-2/neu protein in the samples.

Thereafter, the secretion of the soluble ECD-PD fusion protein was determined by Western blot analysis with Her-2/neu PD specific antibodies as follows: culture media and cell lysates from transfected HEK-293 cells were separated on 7.5% SDS polyacrylamide gel. For western blot analysis, the proteins were transferred electrophoretically to PVDF filters. The PVDF filters were incubated with 5% bovine serum albumin in TBST, incubated for 1 hour with the primary antibody, and incubated for another hour with peroxidase-conjugated goat anti-mouse antibody. Immunoblots were developed using the ECL system (Amersham Corp.). The mouse Ab-3 monoclonal antibody (Oncogene Science), was used for detecting the Her-2/neu protein in the present experiments. Ab-3 recognizes the carboxyl terminal of human Her-2/neu protein. For detecting FLAG-Tag fusion proteins, M2 monoclonal antibody (Kodak) was used as primary antibody in the analysis. The results are presented in FIG. 6.

Example 5

Cloning of the Human ECD-ΔPD Fusion Protein into the pcDNA3.1/hyg Expression Vector The human ECD-ΔPD fusion protein, shown in FIG. 13 (SEQ ID NO:7), was prepared by polymerase chain reaction (PCR) with the following primers:

```
PDM-251  5'-cctgaatcgcgaacccaagtgtgcaccggcac-3'   (SEQ ID NO:15) Tm 69° C.

PDM-279  5'-ctggactcgagtcattagcggtgcctgtggtgg-3'  (SEQ ID NO:16) Tm 69° C.
```

The polymerase chain reaction conditions were: 10 µl 10× Pfu Buffer (Stratagene), 1 µl 10 mM dNTPs, 2 µl 10 µM each primer, 83 µl sterile water, 1.5 µl Pfu DNA polymerase, and 50 ng template at 96° C. for 2 minutes×1 cycle; (96° C. for 20 seconds, 69° C. for 15 seconds, 72° C. for 5 minutes)×40 cycles; 72° C. for 5 minutes×1 cycle. The PCR product was digested with Nru I and Xho I, and cloned into a pPDM His vector (a modified pET28 vector which has a His-tag in-frame with a blunt Restriction enzyme cutter Eco 72I), which was cut with Eco 72I and Xho I. The sequence was confirmed and the recombinant plasmid was then transformed into BL21 pLys S for E. coli expression. The plasmid construct was then digested with BamHI and XhoI and cloned into pcDNA3.1/hyg/ECD-PD which was cut with the same restriction enzymes.

Example 6

Expression in E. coli of Human ECD-PD-$C_T$-HIS Tag Fusion Protein

The human ECD-PD fusion protein was cloned into the pcDNA3.1/hyg vector as described in example 2 and was used as template for constructing the hECD-PD in frame with a C-terminal 6× histidine tag. The hECD-PD was amplified by PCR using the following primers:

```
AW028 hECD-PD sense primer, with Nco I site:
5'-GGGccatggggAGCACCCAAGTGTGCACCGGC-3
(SEQ ID NO:17)

AW029 hECD-PD antisense primer, with Xho I site
without stop:
5'-GGGctcgagCACTGGCACGTCCAGACCCAGG-3'
(SEQ ID NO:18)
```

The PCR product was then cut with the Nco I and Xho I restriction enzymes, purified, and ligated into the pET28b expression vector linearized with the same two restriction enzymes. The ligation product was transformed into NovaBlue cells and several colonies were selected for screening. Of those, the hECD-PD.$C_T$his clones were confirmed by DNA sequence and used for subsequent protein expression.

For protein expression, a hECD-PD.$C_T$his clone was transformed into BL21 (DE3) CodonPlus-RIU E. coli competent cells. A standard mini expression screen was carried out with clones from the transformation to determine the induction yield. The best results were obtained when the cells were grown in TB media at 37° C. for 2 hours.

Figure 17:
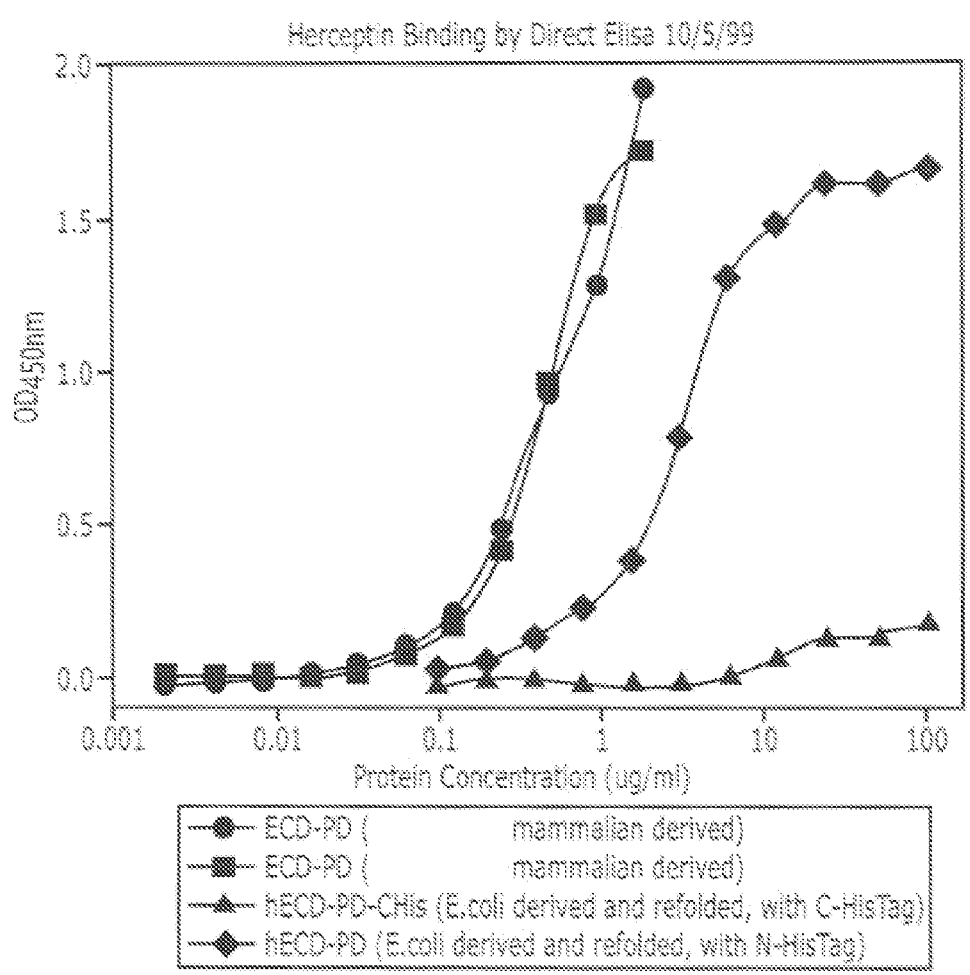
FIG. 17 illustrates the results of an ELISA assay for HERCEPTIN® Her-2/neu antibody binding to different ECD-PD fusion proteins produced either in mammalian cells or in *E. coli*. The fusion proteins produced in *E. coli* are in frame with a C- or N-terminal 6× histidine tag (noted C-His tag and N-His tag, respectively).

The E. coli produced hECD-PD.C$_T$his was then purified on a monoQ column, and refolded in 20 mM Tris-HCl (pH 8.0) buffer. The refolded protein was tested and found to be positive for HERCEPTIN® Her-2/neu antibody binding by Western blot and ELISA (FIG. 17). The HERCEPTIN® Her-2/neu antibody binding activity was, however, lost later on, probably due to denaturation of the protein.

Example 7

Expression in E. coli of Human N$_T$-HIS TAG-ECD-PD Fusion Protein

The human ECD-PD fusion protein was cloned into the pPDM expression vector with a 5'Nde I and a 3' Xho I restriction sites. The ECD-PD insert was fused in frame with a N-terminal 6× histidine tag.

For protein expression, the pPDM vector containing the N$_T$his-hECD-PD fusion protein was transformed into BL21 (DE3) CodonPlus-RIU E. coli competent cells. A standard mini expression screen was carried out with clones from the transformation to determine the induction yield. The best results were obtained when the cells were grown in TB media at 30° C. for 2 hours.

The E. coli derived unpurified N$_T$his-hECD-PD fusion protein was recognized by the mouse c-neu-3 antibody and by a rabbit anti-ECD antibody. Following purification, the E. coli derived N$_T$his-hECD-PD was recognized by HERCEPTIN® Her-2/neu antibody both in Western blots and in ELISA assays (FIG. 17).

Example 8

Expression in E. coli of Mouse ECD-PD-C$_T$ HIS Tag Fusion Protein

The mouse ECD-PD fusion protein was cloned into the pcDNA3.1 vector following a protocol similar to that described in example 2 for cloning the human ECD-PD fusion protein. This construct was then used as template for constructing the mECD-PD in frame with a C-terminal 6× histidine tag followed by a stop codon. The internal Nco I site in the mECD-PD/pcDNA3.1 construct (base pair 1932 of the ORF) was silently mutated by site-directed mutagenesis using the following primers:

```
AW038 primer:                        (SEQ ID NO:19)
5'-GGCCCCTCCAGCCCgATGGACAGCACCTTCTACCG-3'

AW039 primer:                        (SEQ ID NO:20)
5'-CGGTAGAAGGTGCTGTCCATcGGGCTGGAGGGGCC-3'
```

After the sequence was confirmed, the mECD-PD fusion construct was amplified by PCR using the following primers:

AW036 sense primer, with Nco I restriction site:
5'-GGGccatggGTACCCAAGTGTGTACCGG-3' (SEQ ID NO:21)

AW037 antisense primer, with Xho I restriction site:
5'-GGGctcgagTCAATGGTGATGGTGATGGTGTCATGGCACATCCAGGCC TAGGTACTCAGGG-3' (SEQ ID NO:22)

The PCR product was then cut with the Nco I and Xho I restriction enzymes, purified, and ligated into the pET28b expression vector linearized with the same two restriction enzymes.

The ligation product was transformed into NovaBlue and yielded multiple colonies. Four colonies were selected for sequence analysis. Of those, a mECD-PD.C$_T$his clone which had the correct sequence was transformed into BL21 (DE3) CodonPlus-RIU E. coli competent cells. A standard mini expression screen was carried out with clones from the transformation to determine the induction yield. The best results were obtained when the cells were grown in 2xYT media at 30° C. for 3 hours.

Example 9

Expression in E. coli of the Ra12-mECD-PD-C$_T$ HIS Tag Fusion Protein

The mouse ECD-PD fusion protein was cloned into the pET28b expression vector as described in Example 8. The Ra12 sequence was amplified using the following PCR fragments that added Nco I sites on the 5' and 3' ends:

```
Ra12.JC05:                           (SEQ ID NO:23)
5'-CCGccatggGCACGGCCGCGTCCGATAACTTCC-3'

Ra12.JC06:                           (SEQ ID NO:24)
5'-GCGccatggCGGCCGGGGGTCCCTCGGCC-3'
```

To obtain the Ra12 adjuvant fusion with mECD-PD, the Ra12 PCR product was then digested with the Nco I restriction enzyme, and ligated into the Nco I digested and CIAP treated pET28b-mECD-PD vector. The ligation product was transformed into NovaBlue cells and yielded multiple colonies. Due to the non-directional specific ligation reaction, twice as many clones were picked for plasmid miniprep. These clones were screened by digestion with the Afi III restriction enzyme for correct orientation of the insert. The sequence of a few correctly oriented clones was analyzed. One clone with a correct sequence was transformed into BL21 (DE3) CodonPlus-RIU E. coli competent cells for expression. A standard mini expression screen was carried out with clones from the transformation to determine the induction yield. The best results were obtained when the cells were grown in LB media at 37° C. for 3 hours.

Example 10

Expression in E. coli of LeIF.mECD-PD-C$_T$ HIS Tag Fusion Protein

The mouse ECD-PD fusion protein was cloned into the pET28b expression vector as described in Example 8. The LeIF sequence was amplified using the following PCR fragments that added Nco I sites on the 5' and 3' ends:

```
LeIF.JC03:                           (SEQ ID NO:25)
5'-CGCccatggCGCAGAATGATAAGATCGCCC-3'

LeIF.JC04:                           (SEQ ID NO:26)
5'-GCCccatggCGTCGCGCATGAACTTCTTCGTC-3'
```

To obtain the LeIF adjuvant fusion with mECD-PD, the LeIF PCR product was then digested by the Nco I restriction enzyme, and ligated into the Nco I digested and CIAP treated pET28b-mECD-PD vector. The ligation product was transformed into NovaBlue cells and yielded multiple colonies. Due to the non-directional specific ligation reaction, twice as many clones were picked for plasmid miniprep. These clones were screened by digestion with the Kpn I restriction enzyme for correct orientation of the insert. The sequence of a few correctly oriented clones was analyzed. One clone with a correct sequence was transformed into BL21 (DE3) CodonPlus-RIU *E. coli* competent cells for expression. A standard mini expression screen was carried out with clones from the transformation to determine the induction yield. The best results were obtained when the cells were grown in 2xYT media at 30° C. for 3 hours.

Example 11

Expression in *Pichia* of an ECD-PD Fusion Protein

The ECD-PD recombinant protein used for expression in *Pichia* had the same design as for CHO expression with two modifications: (i) the native secretion signal sequence of the Her-2/neu gene had been replaced by the *Saccharomyces cerevisiae* alpha pre-pro signal sequence; and (ii) the C-terminal part of the recombinant protein was elongated by one glycine and six histidines.

The ECD-PD fusion protein expression cassette was integrated into the SMD1168 *Pichia* strain using the Spheroplast method. Six multicopy integrant clones were selected among 250 clones by quantitative Dot Blot analysis. The selected clones were induced during 72 hours in Buffered Methanol-complex medium (BMMY-1% methanol) in shake-flasks conditions. The six candidate clones showed the same expression profile in the cell-free supernatants and in total cellular extracts.

In the cell-free supernatants, secretion of full-length ECD-PD recombinant protein was very weak and only detected on Western Blots using the c-neu-3 mouse antibody (Calbiochem). Secretion and accumulation (maximum after 72 hours) of a ±70 kDa protein was visible on Silver stained SDS-PAGE and detected on Western blot under non-reducing conditions with HERCEPTIN® Her-2/neu mouse antibody. This protein was not detected using the mouse c-neu-3 antibody or a mouse anti-histidine antibody (QIAGEN).

In total cellular extracts, no specific band was detected on SDS-PAGE using the Silver staining DAIICHI coloration kit. Two bands were detected on Western blots using the mouse c-neu-3 or the mouse anti-histidine antibody. One band has the same molecular size as that observed for the secreted ECD-PD product following expression in CHO cells. The other band appeared as a "smear" ranging from 100–120 kDa. These two signals could correspond to ECD-PD recombinant proteins retained in the E.R. and presenting various forms of glycosylations.

Example 12

Expression in CHOK1 Cells of ECD-PD and ECD-ΔPD Fusion Proteins

The pcDNA3.1/hyg/ECD-PD and pcDNA3.1/hyg/ECD-ΔPD plasmids were digested by the Xba I restriction enzyme and the DNA fragments encompassing the ECD-PD and ECD-ΔPD fusion proteins were gel purified as Xba I fragments of 2783 and 2166 bp, respectively. Each fragment was transferred into the pEE14-GS vector (CellTech) linearized with Xba I (cloning site downstream of the CMV immediate early promoter). After ligation, transformation was performed into DH5α competent *E. coli* cells. Out of sixteen colonies analyzed by restriction enzyme digestion, 2 positive colonies were found for ECD-PD, and 1 positive colony was found for ECD-ΔPD. The obtained plasmids were prepared at large scale and purified by double CsCl-EtBr gradient centrifugation. The plasmids were analyzed by restriction enzyme digestion and sequencing of the 5' and 3' junctions between insert and vector and no abnormalities were found.

Transfection of CHO-K1 cells derived from Master Cell Bank (MCB) CHO-K1 028W 1996/2 SHF P31, growing under suspension serum free conditions, was carried out with both the pEE14-ECD-PD and the pEE14-ECD-ΔPD plasmids using the classical DNA Ca Phosphate co-precipitation technique. Cells were counted 48 hours after transfection and transferred into 96-well plates at a density of 5000 cells/well. Transfected cells were selected according to the procedure of the glutamine synthetase (GS) expression system described by Crockett et al. ((1990) *Biotech.* 8:662) and amplified in the presence of 30 μM methionine sulphoximine (MSX) in GMEM medium containing no glutamine and supplemented with additives (glutamate/asparagine/nucleosides) and 5% dialysed Fetal Bovine Serum (FBS). Cells were washed three times during the first week and twice during the second week following transfection. During the third wash, 20% conditioned medium was added. During the fifth wash, the concentration of MSX was raised to 50 μM to increase the level of selection.

The MSX transfectant clones were transferred 3–5 weeks after transfection into 24-well plates and the culture supernatants were harvested. Expression of the ECD-PD or ECD-ΔPD fusion proteins was tested by Western blot analysis using Herceptin antibody under non reducing conditions. Expression of the ECD-PD fusion protein was detected in 18 out of 52 clones tested, while 13 out of 47 clones tested were positive for ECD-ΔPD expression. The selected clones expressing the fusion proteins were then readapted to suspension serum-free conditions. Based on the level of expression, growth and viability, 5 clones carrying the ECD-PD construct and 3 clones carrying the ECD-ΔPD construct were further evaluated and characterized. For the ECD-PD construct, clone 560 F3 showed the highest expression level.

Figure 18:
FIG. 18 shows a comparison of Her-2/neu ECD-PD fusion protein expression in CHO-K1, grown in suspension under serum-free conditions, and in *Pichia* cells.

Expression was evaluated at 33° C. in the presence or absence of sodium butyrate (2 mM) and of DMSO (2%). Some of the clones were inducible by NaB or DMSO. Expression in CHO-K1 cells of ECD-PD and ECD-ΔPD was analyzed by Western blots and SDS-PAGE followed by either Silver or Coomassie staining. The Herceptin and the c-neu-3 mouse monoclonal antibodies, as well as the 8029K rabbit polyclonal antibody were used for Western blot analysis. Analysis of the culture supernatants from ECD-PD and ECD-ΔPD clones showed a band in Coomassie/Silver stained gels at 150 kDa and at 98 kDa, respectively. The same bands were revealed by Herceptin and by the 8029K polyclonal antiserum, as well as by the c-neu-3 antibody for ECD-PD only (FIG. 18). The CHO-expressed Her-2/neu fusion proteins are recognized by the Herceptin antibody (FIG. 18).

The expression level of the fusion proteins was also followed in terms of stability during the different cell passages. Five ECD-PD clones and two ECD-ΔPD clones were followed during passages and the stability of expression was evaluated by Western blot analysis. Out of the seven analyzed clones, four were stable after more than 32 passages, although one of them showed a high mortality and the other presented big cells.

Small scale production runs were carried out with the two best ECD-PD and ECD-ΔPD clones. Cells were cultured in suspension under serum-free conditions for 120 hours at 33°

C. in the presence of 2 mM Sodium butyrate. The expression of both fusion proteins was evaluated by Western blot using the HERCEPTIN® Her-2/neu antibody and by SDS-PAGE followed by silver staining using the Daiichi kit. Both fusion proteins were found to be expressed at +/−100 µg/ml.

Example 13

Purification of ECD-PD and ECD-ΔPD Fusion Proteins Following Expression in CHO Cells Following expression in CHO cells and secretion, the ECD-PD and ECD-ΔPD fusion proteins were purified by anion exchange chromatography on Q sepharose High Performance columns. Before loading the supernatant onto the column, the pH was adjusted to 6.5 by adding 1N HCl. For the chromatography, 1 ml of Q Sepharose High Performance resin (Pharmacia) was used for a C10/10 column (Pharmacia).

The column was first equilibrated with 10 column volumes of $H_2O$ at 4 ml/min, followed by 1 column volume of 0.5 M NaOH at 4 ml/min, and 10 column volumes of Buffer A (20 mM Bis-Tris propane pH 6.5–50 mM NaCl) at 4 ml/min. The sample was then loaded onto the column and allowed to pass through at a flow rate of 1 ml/min. The column was then washed with Buffer A at 1 ml/min until the O.D. at 280 nm reached 0.1, and an additional wash step of 20 column volumes was then performed. Before elution, the flow stream was reversed and an additional wash step of 3 column volumes was performed.

The elution was carried out at 1 ml/min, first with Buffer B (20 mM Bis-Tris propane pH 6.5–250 mM NaCl), and then with Buffer C (20 mM Bis-Tris propane pH 6.5–1 mM NaCl). The fusion proteins of interest were eluted with buffer B.

The fusion proteins were further purified by hydrophobic chromatography on Phenyl Sepharose 6 Fast Flow low substitution. The eluate containing the ECD-PD and ECD-ΔPD fusion proteins (Buffer B eluate) was adjusted to obtain a concentration of 1M ammonium sulfate (AMS) by addition of solid AMS (140 g/liter of solution). The pH of the solution was checked to be 7.0.

For the chromatography, 0.5 ml of Phenyl Sepharose 6 Fast Flow low substitution (Pharmacia) was used with a C10/10 (Pharmacia). The column was then equilibrated with 10 column volumes of $H_2O$, at 4 ml/min, 1 column volume of 0.5 M NaOH, at 4 ml/min, and 10 column volumes of buffer D (1 mM $PO_4$ pH 7.0–1M AMS), at 4 ml/min. Following equilibration, the sample was loaded and allowed to pass through the column at a flow rate of 0.5 ml/min. The column was then washed in Buffer D at 0.5 ml/min until the O.D. at 280 nm reached the baseline, and then at 1 ml/min for 10 column volumes. Before elution, the flow stream was reversed and an additional wash step of 3 column volumes was performed. Elution was carried out at 1 ml/min with buffer E (1 mM $PO_4$ pH 7.0).

The purified fusion proteins were analyzed by SDS-PAGE followed by silver staining using the Daiichi kit, and by Western blot, using the 8029K rabbit polyclonal antibody or the mouse HERCEPTIN® Her-2/neu antibody. The analysis showed that the level of purity following the two purification steps was estimated at +/−90% by densitometry (Biorad GS-700 Imaging Densitometer). The Western blot analysis showed that the monomers remained the major band all along the purification, that the level of oxidation was not increased, and that the detection of the epitope of interest was not modified by the conditions of purification, as shown by using the HERCEPTIN® Her-2/neu antibody. The total amount of each fusion protein recovered was measured using a colorimetric protein assay (DOC TCA BCA). This assays estimated that 2 and 4 mg of ECD-PD and ECD-ΔPD fusion protein, respectively, were purified from 75 ml of culture, with a level of purity of +/−90%.

Example 14

Expression in Mammalian Cells of the Mouse ECD-PD and ECD-PDTcP0 Fusion Proteins Transiently transfected mammalian HEK293 cells were generated that expressed full-length mouse Neu, Delta mouse Neu, mouse ECD-PD and mouse ECD-PD-TcP0 recombinant proteins. Stable HEK clones that express mouse ECDPD and mouse ECD-PD-TcP0 recombinant proteins were also generated.

Figure 21:
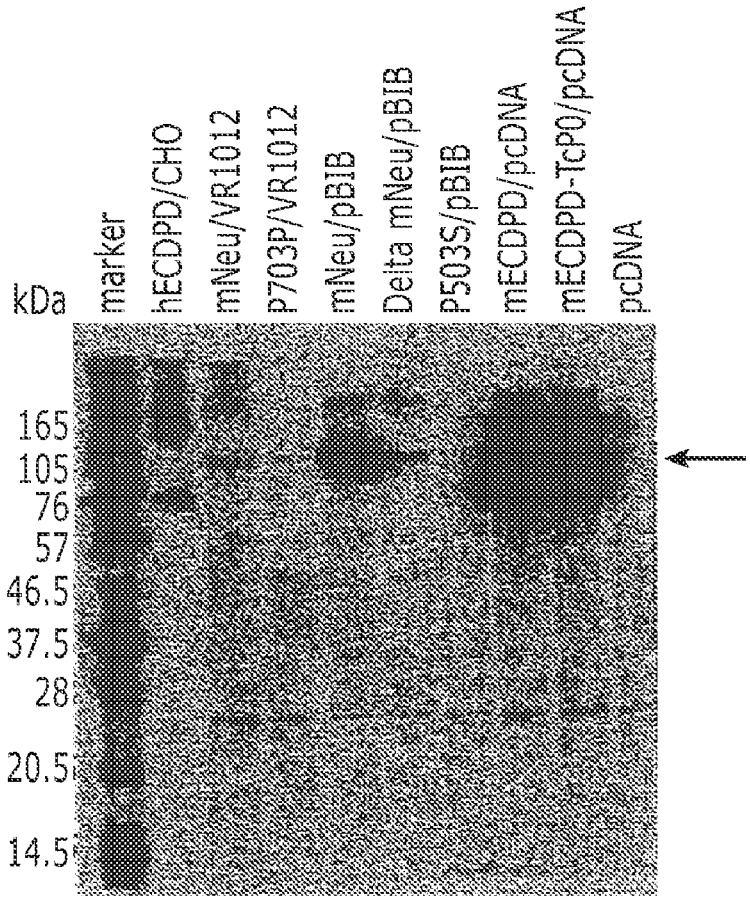
FIG. 21 shows the results of a Western blot analysis of the expression of the mouse Neu (mNeu), mouse delta Neu (Delta mNeu), mouse ECD-PD (mECDPD) and mouse ECD-PDTcP0 (mECD-PD-TcP0) recombinant proteins in HEK293 lysates. The cNeu3 anti-PD antibody was used for detection of the proteins. Delta mouse Neu has a mutated kinase domain, while mECD-PD-TcP0 contains a 6-mer peptide encoding a ribosomal P-peptide epitope.

For recombinant expression in mammalian cells, various forms of mouse Neu (mNeu) cDNAs were subcloned into mammalian expression vectors. Full-length mNeu (FIG. 19) was subcloned into pBIB and VR1012 vectors, and delta mNeu, which contained an engineered A-T basepair change (and subsequent lysine to methionine amino acid change) at position 2261 of the mNeu cDNA, was subcloned into the pBIB vector. A cDNA encoding the extracellular domain (ECD) and phosphorylation domain (PD), and a cDNA encoding the ECD, PD and 6 amino acid TcP0 domains were generated by PCR amplification using full-length mouse Neu cDNA as template. These ECD-PD and ECD-PD-TcP0 products were then subcloned into the mammalian expression vector pcDNA3.1 (Invitrogen) that was modified to contain the DHFR genomic fragment. All constructs were transfected into HEK293 cells (ATCC) using Fugene 6 reagent (Roche). Briefly, the HEK cells were plated at a density of 100,000 cells/ml in DMEM (Gibco) containing 10% FBS (Hyclone) and grown overnight. The following day, 2 µl of Fugene6 was added to 100 µl of DMEM containing no FBS and incubated for 15 minutes at RT. The Fugene6/DMEM mixture was then added to 1 µg of mNeu/ expression vector DNA and incubated for 15 minutes at RT. The Fugene/DNA mix was then added to the HEK293 cells and incubated for 48–72 hours at 37° C. with 7% $CO_2$. Cells were rinsed with PBS and then collected and pelleted by centrifugation. For Western blot analysis, whole cell lysates were generated by incubating the cells in Triton-X 100 containing lysis buffer for 30 minutes on ice. Lysates were then cleared by centrifugation at 10,000 rpm for 5 minutes at 4° C. Samples were diluted with SDS-PAGE loading buffer containing beta-mercaptoethanol, then boiled for 10 minutes prior to loading the SDS-PAGE gel. The proteins were transferred to nitrocellulose and probed using the mouse monoclonal Ab-3 (c-neu 3; CalBiochem) at a concentration of 1 µg/ml. The blot was revealed with a goat anti-mouse Ig coupled to HRP followed by incubation in ECL substrate (FIG. 21).

From the foregoing, it will be appreciated that, although specific embodiments of the invention have been described herein for the purpose of illustration, various modifications may be made without deviating from the spirit and scope of the invention.

What is claimed is:

1. An isolated fusion polypeptide comprising:
   (a) SEQ ID NO: 3; and
   (b) SEQ ID NO: 4;
   wherein (a) and (b) are joined by a chemical linker selected from the group consisting of non-amino acid chemical linkers and amino acid sequences of no more than 50 amino acids; and wherein said polypeptide does not comprise a Her-2/Neu transmembrane domain.

2. The polypeptide of claim 1, wherein (a) and (b) are joined via a non-amino acid chemical linker.

3. The polypeptide of claim 1, wherein (a) and (b) are joined via a sequence of no more than 50 amino acids.

4. The polypeptide of claim 1, further comprising a peptide having the sequence set forth in SEQ ID NO:31.

5. The polypeptide of claim 4, wherein said peptide having the sequence set forth in SEQ ID NO:31 is linked to the C-terminus of sequence (b).

6. The polypeptide of claim 1, further comprising an NS1 antigen or an immunogenic fragment thereof.

7. The polypeptide of claim 6, wherein the NS1 antigen or immunogenic fragment thereof is linked to the N-terminus of sequence (a).

8. A composition comprising the polypeptide of claim 1, and a physiologically acceptable carrier or diluent.

9. The composition of claim 8, further comprising an immunostimulatory substance.

10. The composition of claim 9, wherein the protein is presented in an oil-in-water emulsion.

11. The composition of claim 9, wherein the immunostimulatory substance is 3D-MPL, QS21, or a combination of 3D-MPL and QS21.

12. The polypeptide of claim 1, wherein the polypeptide is a secreted polypeptide.

13. An isolated fusion polypeptide comprising:
   (a) SEQ ID NO: 3; and
   (b) SEQ ID NO: 5;
   wherein (a) and (b) are joined by a chemical linker selected from the group consisting of non-amino acid chemical linkers and amino acid sequences of no more than 50 amino acids; and wherein said polypeptide does not comprise a Her-2/Neu transmembrane domain.

14. The polypeptide of claim 13, wherein (a) and (b) are joined via a non-amino acid chemical linker.

15. The polypeptide of claim 13, wherein (a) and (b) are joined via a sequence of no more than 50 amino acids.

16. The polypeptide of claim 13, further comprising a peptide having the sequence set forth in SEQ ID NO:31.

17. The polypeptide of claim 16, wherein said peptide of SEQ ID NO:31 is linked to the C-terminus of sequence (b).

18. A composition comprising the polypeptide of claim 13, and a physiologically acceptable carrier or diluent.

19. The composition of claim 18, further comprising an immunostimulatory substance.

20. The composition of claim 19, wherein the protein is presented in an oil-in-water emulsion.

21. The composition of claim 19, wherein the immunostimulatory substance is 3D-MPL, QS21, or a combination of 3D-MPL and QS21.

22. The polypeptide of claim 13, wherein the polypeptide is a secreted polypeptide.

23. The polypeptide of claim 13, further comprising an NS1 antigen or an immunogenic fragment thereof.

24. The polypeptide of claim 23, wherein the NS1 antigen or immunogenic fragment thereof is linked to the N-terminus of sequence (a).

25. An isolated fusion polypeptide comprising:
   (a) SEQ ID NO: 3; and
   (b) the amino acid sequence of the fragment Gln 991 to Val 1256, inclusive, of SEQ ID NO:2;
   wherein (a) and (b) are joined by a chemical linker selected from the group consisting of non-amino acid chemical linkers and amino acid sequences of no more than 50 amino acids.

26. An isolated fusion polypeptide comprising:
   (a) SEQ ID NO: 8; and
   (b) SEQ ID NO: 4;
   wherein (a) and (b) are joined by a chemical linker selected from the group consisting of non-amino acid chemical linkers and amino acid sequences of no more than 50 amino acids.

27. An isolated fusion polypeptide comprising:
   (a) SEQ ID NO: 8; and
   (b) the amino acid sequence of the fragment Gln 991 to Val 1256, inclusive, of SEQ ID NO:2;
   wherein (a) and (b) are joined by a chemical linker selected from the group consisting of non-amino acid chemical linkers and amino acid sequences of no more than 50 amino acids.

28. An isolated polypeptide comprising SEQ ID NO:29.

29. An isolated fusion polypeptide comprising:
   (a) SEQ ID NO: 3; and
   (b) the amino acid sequence of the fragment Gln 991 to Arg 1049, inclusive, of SEQ ID NO:2;
   wherein (a) and (b) are joined by a chemical linker selected from the group consisting of non-amino acid chemical linkers and amino acid sequences of no more than 50 amino acids.

30. An isolated fusion polypeptide comprising:
   (a) SEQ ID NO: 8; and
   (b) SEQ ID NO: 5;
   wherein (a) and (b) are joined by a chemical linker selected from the group consisting of non-amino acid chemical linkers and amino acid sequences of no more than 50 amino acids.

31. An isolated fusion polypeptide comprising
   (a) SEQ ID NO: 8; and
   (b) the amino acid sequence of the fragment Gln 991 to Arg 1049, inclusive, of SEQ ID NO:2;
   wherein (a) and (b) are joined by a chemical linker selected from the group consisting of non-amino acid chemical linkers and amino acid sequences of no more than 50 amino acids.

32. An isolated polypeptide comprising SEQ ID NO:6.

33. An isolated polypeptide comprising SEQ ID NO:7.

34. An isolated fusion polypeptide comprising:
   (a) SEQ ID NO: 3 linked directly to
   (b) the amino acid sequence of the fragment Gln 991 to Val 1256, inclusive, of SEQ ID NO:2.

35. An isolated fusion polypeptide comprising:
   (a) SEQ ID NO: 8 linked directly to
   (b) SEQ ID NO: 4.

36. An isolated fusion polypeptide comprising:
   (a) SEQ ID NO: 8 linked directly to
   (b) the amino acid sequence of the fragment Gln 991 to Val 1256, inclusive, of SEQ ID NO:2.

37. An isolated fusion polypeptide comprising:
   (a) SEQ ID NO: 3 linked directly to
   (b) the amino acid sequence of the fragment Gln 991 to Arg 1049, inclusive, of SEQ ID NO:2.

38. An isolated fusion polypeptide comprising:
   (a) SEQ ID NO: 8 linked directly to
   (b) SEQ ID NO: 5.

39. An isolated fusion polypeptide comprising:
   (a) SEQ ID NO: 8 linked directly to
   (b) the amino acid sequence of the fragment Gln 991 to Arg 1049, inclusive, of SEQ ID NO:2.

* * * * *

SEQUENCE LISTING

<160> NUMBER OF SEQ ID NOS: 32

<210> SEQ ID NO 1
<211> LENGTH: 1255
<212> TYPE: PRT
<213> ORGANISM: Homo sapiens
<220> FEATURE:
<223> OTHER INFORMATION: human Her-2/neu protein
<221> NAME/KEY: DOMAIN
<222> LOCATION: (1)..(653)
<223> OTHER INFORMATION: extracellular domain (ECD)
<221> NAME/KEY: DOMAIN
<222> LOCATION: (676)..(1255)
<223> OTHER INFORMATION: intracellular domain (ICD)
<221> NAME/KEY: DOMAIN
<222> LOCATION: (990)..(1255)
<223> OTHER INFORMATION: phosphorylation domain (PD)
<221> NAME/KEY: DOMAIN
<222> LOCATION: (990)..(1048)
<223> OTHER INFORMATION: fragment of the phosphorylation domain,
      preferred portion (delta PD)

<400> SEQUENCE: 1

Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg

-continued

```
                275                 280                 285
Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
                450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
                675                 680                 685

Arg Leu Leu Gln Glu Thr Glu Leu Val Glu Pro Leu Thr Pro Ser Gly
690                 695                 700
```

-continued

```
Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
            725                 730                 735

Gly Ile Trp Ile Pro Asp Gly Glu Asn Val Lys Ile Pro Val Ala Ile
        740                 745                 750

Lys Val Leu Arg Glu Asn Thr Ser Pro Lys Ala Asn Lys Glu Ile Leu
    755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
        820                 825                 830

Met Ser Tyr Leu Glu Asp Val Arg Leu Val His Arg Asp Leu Ala Ala
    835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
        900                 905                 910

Trp Glu Leu Met Thr Phe Gly Ala Lys Pro Tyr Asp Gly Ile Pro Ala
    915                 920                 925

Arg Glu Ile Pro Asp Leu Leu Glu Lys Gly Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
        980                 985                 990

Asp Leu Gly Pro Ala Ser Pro Leu Asp Ser Thr Phe Tyr Arg Ser Leu
    995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
            1045                1050                1055

Gly Asp Leu Thr Leu Gly Leu Glu Pro Ser Glu Glu Glu Ala Pro Arg
        1060                1065                1070

Ser Pro Leu Ala Pro Ser Glu Gly Ala Gly Ser Asp Val Phe Asp Gly
    1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120
```

-continued

```
Pro Ser Glu Thr Asp Gly Tyr Val Ala Pro Leu Thr Cys Ser Pro Gln
            1125                1130                1135

Pro Glu Tyr Val Asn Gln Pro Asp Val Arg Pro Gln Pro Pro Ser Pro
        1140                1145                1150

Arg Glu Gly Pro Leu Pro Ala Ala Arg Pro Ala Gly Ala Thr Leu Glu
    1155                1160                1165

Arg Pro Lys Thr Leu Ser Pro Gly Lys Asn Gly Val Val Lys Asp Val
1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
            1205                1210                1215

Phe Asp Asn Leu Tyr Tyr Trp Asp Gln Asp Pro Pro Glu Arg Gly Ala
        1220                1225                1230

Pro Pro Ser Thr Phe Lys Gly Thr Pro Thr Ala Glu Asn Pro Glu Tyr
    1235                1240                1245

Leu Gly Leu Asp Val Pro Val
   1250                1255

<210> SEQ ID NO 2
<211> LENGTH: 1256
<212> TYPE: PRT
<213> ORGANISM: Rattus sp.
<220> FEATURE:
<223> OTHER INFORMATION: rat Her-2/neu protein
<221> NAME/KEY: DOMAIN
<222> LOCATION: (1)..(654)
<223> OTHER INFORMATION: extracellular domain (ECD)
<221> NAME/KEY: DOMAIN
<222> LOCATION: (677)..(1256)
<223> OTHER INFORMATION: intracellular domain (ICD)
<221> NAME/KEY: DOMAIN
<222> LOCATION: (721)..(998)
<223> OTHER INFORMATION: kinase domain (KD)
<221> NAME/KEY: DOMAIN
<222> LOCATION: (991)..(1256)
<223> OTHER INFORMATION: phosphorylation domain (PD)
<221> NAME/KEY: DOMAIN
<222> LOCATION: (991)..(1049)
<223> OTHER INFORMATION: fragment of the phosphorylation domain,
      preferred portion (delta PD)

<400> SEQUENCE: 2

Met Glu Leu Ala Ala Trp Cys Arg Trp Gly Phe Leu Leu Ala Leu Leu
 1               5                  10                  15

Pro Pro Gly Ile Ala Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Val Pro Ala Asn Ala Ser Leu Ser Phe Leu Gln Asp Ile Gln Glu Val
65                  70                  75                  80

Gln Gly Tyr Met Leu Ile Ala His Asn Gln Val Lys Arg Val Pro Leu
                85                  90                  95

Gln Arg Leu Arg Ile Val Arg Gly Thr Gln Leu Phe Glu Asp Lys Tyr
            100                 105                 110

Ala Leu Ala Val Leu Asp Asn Arg Asp Pro Gln Asp Asn Val Ala Ala
        115                 120                 125

Ser Thr Pro Gly Arg Thr Pro Glu Gly Leu Arg Glu Leu Gln Leu Arg
    130                 135                 140
```

-continued

```
Ser Leu Thr Glu Ile Leu Lys Gly Gly Val Leu Ile Arg Gly Asn Pro
145                 150                 155                 160

Gln Leu Cys Tyr Gln Asp Met Val Leu Trp Lys Asp Val Phe Arg Lys
                165                 170                 175

Asn Asn Gln Leu Ala Pro Val Asp Ile Asp Thr Asn Arg Ser Arg Ala
            180                 185                 190

Cys Pro Pro Cys Ala Pro Ala Cys Lys Asp Asn His Cys Trp Gly Glu
        195                 200                 205

Ser Pro Glu Asp Cys Gln Ile Leu Thr Gly Thr Ile Cys Thr Ser Gly
    210                 215                 220

Cys Ala Arg Cys Lys Gly Arg Leu Pro Thr Asp Cys Cys His Glu Gln
225                 230                 235                 240

Cys Ala Ala Gly Cys Thr Gly Pro Lys His Ser Asp Cys Leu Ala Cys
                245                 250                 255

Leu His Phe Asn His Ser Gly Ile Cys Glu Leu His Cys Pro Ala Leu
            260                 265                 270

Val Thr Tyr Asn Thr Asp Thr Phe Glu Ser Met His Asn Pro Glu Gly
        275                 280                 285

Arg Tyr Thr Phe Gly Ala Ser Cys Val Thr Thr Cys Pro Tyr Asn Tyr
    290                 295                 300

Leu Ser Thr Glu Val Gly Ser Cys Thr Leu Val Cys Pro Pro Asn Asn
305                 310                 315                 320

Gln Glu Val Thr Ala Glu Asp Gly Thr Gln Arg Cys Glu Lys Cys Ser
                325                 330                 335

Lys Pro Cys Ala Arg Val Cys Tyr Gly Leu Gly Met Glu His Leu Arg
            340                 345                 350

Gly Ala Arg Ala Ile Thr Ser Asp Asn Val Gln Glu Phe Asp Gly Cys
        355                 360                 365

Lys Lys Ile Phe Gly Ser Leu Ala Phe Leu Pro Glu Ser Phe Asp Gly
    370                 375                 380

Asp Pro Ser Ser Gly Ile Ala Pro Leu Arg Pro Glu Gln Leu Gln Val
385                 390                 395                 400

Phe Glu Thr Leu Glu Glu Ile Thr Gly Tyr Leu Tyr Ile Ser Ala Trp
                405                 410                 415

Pro Asp Ser Leu Arg Asp Leu Ser Val Phe Gln Asn Leu Arg Ile Ile
            420                 425                 430

Arg Gly Arg Ile Leu His Asp Gly Ala Tyr Ser Leu Thr Leu Gln Gly
        435                 440                 445

Leu Gly Ile His Ser Leu Gly Leu Arg Ser Leu Arg Glu Leu Gly Ser
    450                 455                 460

Gly Leu Ala Leu Ile His Arg Asn Ala His Leu Cys Phe Val His Thr
465                 470                 475                 480

Val Pro Trp Asp Gln Leu Phe Arg Asn Pro His Gln Ala Leu Leu His
                485                 490                 495

Ser Gly Asn Arg Pro Glu Glu Asp Cys Gly Leu Glu Gly Leu Val Cys
            500                 505                 510

Asn Ser Leu Cys Ala His Gly His Cys Trp Gly Pro Gly Pro Thr Gln
        515                 520                 525

Cys Val Asn Cys Ser His Phe Leu Arg Gly Gln Glu Cys Val Glu Glu
    530                 535                 540

Cys Arg Val Trp Lys Gly Leu Pro Arg Glu Tyr Val Ser Asp Lys Arg
545                 550                 555                 560
```

-continued

```
Cys Leu Pro Cys His Pro Glu Cys Gln Pro Gln Asn Ser Ser Glu Thr
            565                 570                 575
Cys Phe Gly Ser Glu Ala Asp Gln Cys Ala Ala Cys Ala His Tyr Lys
            580                 585                 590
Asp Ser Ser Cys Val Ala Arg Cys Pro Ser Gly Val Lys Pro Asp
            595                 600                 605
Leu Ser Tyr Met Pro Ile Trp Lys Tyr Pro Asp Glu Glu Gly Ile Cys
            610                 615                 620
Gln Pro Cys Pro Ile Asn Cys Thr His Ser Cys Val Asp Leu Asp Glu
625                 630                 635                 640
Arg Gly Cys Pro Ala Glu Gln Arg Ala Ser Pro Val Thr Phe Ile Ile
                645                 650                 655
Ala Thr Val Glu Gly Val Leu Leu Phe Leu Ile Leu Val Val Val Val
                660                 665                 670
Gly Ile Leu Ile Lys Arg Arg Arg Gln Lys Ile Arg Lys Tyr Thr Met
            675                 680                 685
Arg Arg Leu Leu Gln Glu Thr Glu Leu Val Glu Pro Leu Thr Pro Ser
            690                 695                 700
Gly Ala Met Pro Asn Gln Ala Gln Met Arg Ile Leu Lys Glu Thr Glu
705                 710                 715                 720
Leu Arg Lys Val Lys Val Leu Gly Ser Gly Ala Phe Gly Thr Val Tyr
                725                 730                 735
Lys Gly Ile Trp Ile Pro Asp Gly Glu Asn Val Lys Ile Pro Val Ala
                740                 745                 750
Ile Lys Val Leu Arg Glu Asn Thr Ser Pro Lys Ala Asn Lys Glu Ile
            755                 760                 765
Leu Asp Glu Ala Tyr Val Met Ala Gly Val Gly Ser Pro Tyr Val Ser
            770                 775                 780
Arg Leu Leu Gly Ile Cys Leu Thr Ser Thr Val Gln Leu Val Thr Gln
785                 790                 795                 800
Leu Met Pro Tyr Gly Cys Leu Leu Asp His Val Arg Glu His Arg Gly
                805                 810                 815
Arg Leu Gly Ser Gln Asp Leu Leu Asn Trp Cys Val Gln Ile Ala Lys
            820                 825                 830
Gly Met Ser Tyr Leu Glu Asp Val Arg Leu Val His Arg Asp Leu Ala
            835                 840                 845
Ala Arg Asn Val Leu Val Lys Ser Pro Asn His Val Lys Ile Thr Asp
850                 855                 860
Phe Gly Leu Ala Arg Leu Leu Asp Ile Asp Glu Thr Glu Tyr His Ala
865                 870                 875                 880
Asp Gly Gly Lys Val Pro Ile Lys Trp Met Ala Leu Glu Ser Ile Leu
                885                 890                 895
Arg Arg Arg Phe Thr His Gln Ser Asp Val Trp Ser Tyr Gly Val Thr
            900                 905                 910
Val Trp Glu Leu Met Thr Phe Gly Ala Lys Pro Tyr Asp Gly Ile Pro
            915                 920                 925
Ala Arg Glu Ile Pro Asp Leu Leu Glu Lys Gly Glu Arg Leu Pro Gln
            930                 935                 940
Pro Pro Ile Cys Thr Ile Asp Val Tyr Met Ile Met Val Lys Cys Trp
945                 950                 955                 960
Met Ile Asp Ser Glu Cys Arg Pro Arg Phe Arg Glu Leu Val Ser Glu
                965                 970                 975
Phe Ser Arg Met Ala Arg Asp Pro Gln Arg Phe Val Val Ile Gln Asn
```

-continued

```
                980             985             990
Glu Asp Leu Gly Pro Ser Ser Pro Met Asp Ser Thr Phe Tyr Arg Ser
        995                 1000                1005
Leu Leu Glu Asp Asp Asp Met Gly Asp Leu Val Asp Ala Glu Glu Tyr
    1010                1015                1020
Leu Val Pro Gln Gln Gly Phe Phe Ser Pro Asp Pro Thr Pro Gly Thr
1025                1030                1035                1040
Gly Ser Thr Ala His Arg Arg His Arg Ser Ser Ser Thr Arg Ser Gly
            1045                1050                1055
Gly Gly Glu Leu Thr Leu Gly Leu Glu Pro Ser Glu Glu Gly Pro Pro
        1060                1065                1070
Arg Ser Pro Leu Ala Pro Ser Glu Gly Ala Gly Ser Asp Val Phe Asp
    1075                1080                1085
Gly Asp Leu Ala Met Gly Val Thr Lys Gly Leu Gln Ser Leu Ser Pro
1090                1095                1100
His Asp Leu Ser Pro Leu Gln Arg Tyr Ser Glu Asp Pro Thr Leu Pro
1105                1110                1115                1120
Leu Pro Pro Glu Thr Asp Gly Tyr Val Ala Pro Leu Ala Cys Ser Pro
            1125                1130                1135
Gln Pro Glu Tyr Val Asn Gln Ser Glu Val Gln Pro Gln Pro Pro Leu
        1140                1145                1150
Thr Pro Glu Gly Pro Leu Pro Pro Val Arg Pro Ala Gly Ala Thr Leu
    1155                1160                1165
Glu Arg Pro Lys Thr Leu Ser Pro Gly Lys Asn Gly Val Val Lys Asp
1170                1175                1180
Val Phe Ala Phe Gly Gly Ala Val Glu Asn Pro Glu Tyr Leu Val Pro
1185                1190                1195                1200
Arg Glu Gly Thr Ala Ser Pro Pro His Pro Ser Pro Ala Phe Ser Pro
            1205                1210                1215
Ala Phe Asp Asn Leu Tyr Tyr Trp Asp Gln Asn Ser Ser Glu Gln Gly
        1220                1225                1230
Pro Pro Pro Ser Asn Phe Glu Gly Thr Pro Thr Ala Glu Asn Pro Glu
    1235                1240                1245
Tyr Leu Gly Leu Asp Val Pro Val
    1250                1255

<210> SEQ ID NO 3
<211> LENGTH: 653
<212> TYPE: PRT
<213> ORGANISM: Homo sapiens
<220> FEATURE:
<223> OTHER INFORMATION: extracellular domain (ECD) of human Her-2/neu

<400> SEQUENCE: 3

Met Glu Leu Ala Ala Leu Cys Arg Trp Gly Leu Leu Leu Ala Leu Leu
  1               5                  10                  15
Pro Pro Gly Ala Ala Ser Thr Gln Val Cys Thr Gly Thr Asp Met Lys
                20                  25                  30
Leu Arg Leu Pro Ala Ser Pro Glu Thr His Leu Asp Met Leu Arg His
            35                  40                  45
Leu Tyr Gln Gly Cys Gln Val Val Gln Gly Asn Leu Glu Leu Thr Tyr
        50                  55                  60
Leu Pro Thr Asn Ala Ser Leu Ser Phe Leu Gln Asp Ile Gln Glu Val
 65                  70                  75                  80
Gln Gly Tyr Val Leu Ile Ala His Asn Gln Val Arg Gln Val Pro Leu
```

-continued

```
                     85                  90                  95
Gln Arg Leu Arg Ile Val Arg Gly Thr Gln Leu Phe Glu Asp Asn Tyr
                100                 105                 110
Ala Leu Ala Val Leu Asp Asn Gly Asp Pro Leu Asn Asn Thr Thr Pro
                115                 120                 125
Val Thr Gly Ala Ser Pro Gly Gly Leu Arg Glu Leu Gln Leu Arg Ser
            130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
His Pro Cys Ser Pro Met Cys Lys Gly Ser Arg Cys Trp Gly Glu Ser
        195                 200                 205
Ser Glu Asp Cys Gln Ser Leu Thr Arg Thr Val Cys Ala Gly Gly Cys
    210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
            275                 280                 285
Tyr Thr Phe Gly Ala Ser Cys Val Thr Ala Cys Pro Tyr Asn Tyr Leu
        290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
            435                 440                 445
Gly Ile Ser Trp Leu Gly Leu Arg Ser Leu Arg Glu Leu Gly Ser Gly
        450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
```

-continued

```
Gln Leu Cys Ala Arg Gly His Cys Trp Gly Pro Gly Pro Thr Gln Cys
            515                 520                 525
Val Asn Cys Ser Gln Phe Leu Arg Gly Gln Glu Cys Val Glu Glu Cys
        530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
        610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser
                645                 650

<210> SEQ ID NO 4
<211> LENGTH: 266
<212> TYPE: PRT
<213> ORGANISM: Homo sapiens
<220> FEATURE:
<223> OTHER INFORMATION: phosphorylation domain (PD) of human Her-2/neu

<400> SEQUENCE: 4

Gln Asn Glu Asp Leu Gly Pro Ala Ser Pro Leu Asp Ser Thr Phe Tyr
1               5                   10                  15
Arg Ser Leu Leu Glu Asp Asp Asp Met Gly Asp Leu Val Asp Ala Glu
            20                  25                  30
Glu Tyr Leu Val Pro Gln Gln Gly Phe Phe Cys Pro Asp Pro Ala Pro
        35                  40                  45
Gly Ala Gly Gly Met Val His His Arg His Arg Ser Ser Ser Thr Arg
    50                  55                  60
Ser Gly Gly Gly Asp Leu Thr Leu Gly Leu Glu Pro Ser Glu Glu Glu
65                  70                  75                  80
Ala Pro Arg Ser Pro Leu Ala Pro Ser Glu Gly Ala Gly Ser Asp Val
                85                  90                  95
Phe Asp Gly Asp Leu Gly Met Gly Ala Ala Lys Gly Leu Gln Ser Leu
            100                 105                 110
Pro Thr His Asp Pro Ser Pro Leu Gln Arg Tyr Ser Glu Asp Pro Thr
        115                 120                 125
Val Pro Leu Pro Ser Glu Thr Asp Gly Tyr Val Ala Pro Leu Thr Cys
    130                 135                 140
Ser Pro Gln Pro Glu Tyr Val Asn Gln Pro Asp Val Arg Pro Gln Pro
145                 150                 155                 160
Pro Ser Pro Arg Glu Gly Pro Leu Pro Ala Ala Arg Pro Ala Gly Ala
                165                 170                 175
Thr Leu Glu Arg Pro Lys Thr Leu Ser Pro Gly Lys Asn Gly Val Val
            180                 185                 190
Lys Asp Val Phe Ala Phe Gly Gly Ala Val Glu Asn Pro Glu Tyr Leu
        195                 200                 205
Thr Pro Gln Gly Gly Ala Ala Pro Gln Pro His Pro Pro Pro Ala Phe
    210                 215                 220
```

-continued

Ser Pro Ala Phe Asp Asn Leu Tyr Tyr Trp Asp Gln Asp Pro Pro Glu
225                 230                 235                 240

Arg Gly Ala Pro Pro Ser Thr Phe Lys Gly Thr Pro Thr Ala Glu Asn
                245                 250                 255

Pro Glu Tyr Leu Gly Leu Asp Val Pro Val
            260                 265

<210> SEQ ID NO 5
<211> LENGTH: 59
<212> TYPE: PRT
<213> ORGANISM: Homo sapiens
<220> FEATURE:
<223> OTHER INFORMATION: fragment of the phosphorylation domain,
      preferred portion (delta PD) of human Her-2/neu

<400> SEQUENCE: 5

Gln Asn Glu Asp Leu Gly Pro Ala Ser Pro Leu Asp Ser Thr Phe Tyr
  1               5                  10                  15

Arg Ser Leu Leu Glu Asp Asp Met Gly Asp Leu Val Asp Ala Glu
             20                  25                  30

Glu Tyr Leu Val Pro Gln Gln Gly Phe Phe Cys Pro Asp Pro Ala Pro
            35                  40                  45

Gly Ala Gly Gly Met Val His His Arg His Arg
         50                  55

<210> SEQ ID NO 6
<211> LENGTH: 919
<212> TYPE: PRT
<213> ORGANISM: Artificial Sequence
<220> FEATURE:
<223> OTHER INFORMATION: Description of Artificial Sequence:fusion
      protein of ECD and PD of human Her-2/neu

<400> SEQUENCE: 6

Met Glu Leu Ala Ala Leu Cys Arg Trp Gly Leu Leu Leu Ala Leu Leu
  1               5                  10                  15

Pro Pro Gly Ala Ala Ser Thr Gln Val Cys Thr Gly Thr Asp Met Lys
             20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

-continued

```
His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
            210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605
```

```
Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Gln Asn Glu
                645                 650                 655

Asp Leu Gly Pro Ala Ser Pro Leu Asp Ser Thr Phe Tyr Arg Ser Leu
            660                 665                 670

Leu Glu Asp Asp Asp Met Gly Asp Leu Val Asp Ala Glu Glu Tyr Leu
        675                 680                 685

Val Pro Gln Gln Gly Phe Phe Cys Pro Asp Pro Ala Pro Gly Ala Gly
    690                 695                 700

Gly Met Val His His Arg His Arg Ser Ser Ser Thr Arg Ser Gly Gly
705                 710                 715                 720

Gly Asp Leu Thr Leu Gly Leu Glu Pro Ser Glu Glu Glu Ala Pro Arg
                725                 730                 735

Ser Pro Leu Ala Pro Ser Glu Gly Ala Gly Ser Asp Val Phe Asp Gly
            740                 745                 750

Asp Leu Gly Met Gly Ala Ala Lys Gly Leu Gln Ser Leu Pro Thr His
        755                 760                 765

Asp Pro Ser Pro Leu Gln Arg Tyr Ser Glu Asp Pro Thr Val Pro Leu
770                 775                 780

Pro Ser Glu Thr Asp Gly Tyr Val Ala Pro Leu Thr Cys Ser Pro Gln
785                 790                 795                 800

Pro Glu Tyr Val Asn Gln Pro Asp Val Arg Pro Gln Pro Pro Ser Pro
                805                 810                 815

Arg Glu Gly Pro Leu Pro Ala Ala Arg Pro Ala Gly Ala Thr Leu Glu
            820                 825                 830

Arg Pro Lys Thr Leu Ser Pro Gly Lys Asn Gly Val Val Lys Asp Val
        835                 840                 845

Phe Ala Phe Gly Gly Ala Val Glu Asn Pro Glu Tyr Leu Thr Pro Gln
    850                 855                 860

Gly Gly Ala Ala Pro Gln Pro His Pro Pro Pro Ala Phe Ser Pro Ala
865                 870                 875                 880

Phe Asp Asn Leu Tyr Tyr Trp Asp Gln Asp Pro Pro Glu Arg Gly Ala
                885                 890                 895

Pro Pro Ser Thr Phe Lys Gly Thr Pro Thr Ala Glu Asn Pro Glu Tyr
            900                 905                 910

Leu Gly Leu Asp Val Pro Val
        915

<210> SEQ ID NO 7
<211> LENGTH: 712
<212> TYPE: PRT
<213> ORGANISM: Artificial Sequence
<220> FEATURE:
<223> OTHER INFORMATION: Description of Artificial Sequence:fusion
      protein of ECD and delta PD of human Her-2/neu

<400> SEQUENCE: 7

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45
```

-continued

```
Leu Tyr Gln Gly Cys Gln Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
450                 455                 460
```

-continued

```
Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
        500                 505                 510

Gln Leu Cys Ala Arg Gly His Cys Trp Gly Pro Gly Pro Thr Gln Cys
    515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Gln Asn Glu
                645                 650                 655

Asp Leu Gly Pro Ala Ser Pro Leu Asp Ser Thr Phe Tyr Arg Ser Leu
            660                 665                 670

Leu Glu Asp Asp Asp Met Gly Asp Leu Val Asp Ala Glu Glu Tyr Leu
        675                 680                 685

Val Pro Gln Gln Gly Phe Phe Cys Pro Asp Pro Ala Pro Gly Ala Gly
    690                 695                 700

Gly Met Val His His Arg His Arg
705                 710
```

<210> SEQ ID NO 8
<211> LENGTH: 654
<212> TYPE: PRT
<213> ORGANISM: Rattus sp.
<220> FEATURE:
<223> OTHER INFORMATION: extracellular domain (ECD) of rat Her-2/neu

<400> SEQUENCE: 8

```
Met Glu Leu Ala Ala Trp Cys Arg Trp Gly Phe Leu Leu Ala Leu Leu
1               5                   10                  15

Pro Pro Gly Ile Ala Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Val Pro Ala Asn Ala Ser Leu Ser Phe Leu Gln Asp Ile Gln Glu Val
65                  70                  75                  80

Gln Gly Tyr Met Leu Ile Ala His Asn Gln Val Lys Arg Val Pro Leu
                85                  90                  95

Gln Arg Leu Arg Ile Val Arg Gly Thr Gln Leu Phe Glu Asp Lys Tyr
            100                 105                 110
```

-continued

```
Ala Leu Ala Val Leu Asp Asn Arg Asp Pro Gln Asp Asn Val Ala Ala
            115                 120                 125

Ser Thr Pro Gly Arg Thr Pro Glu Gly Leu Arg Glu Leu Gln Leu Arg
    130                 135                 140

Ser Leu Thr Glu Ile Leu Lys Gly Gly Val Leu Ile Arg Gly Asn Pro
145                 150                 155                 160

Gln Leu Cys Tyr Gln Asp Met Val Leu Trp Lys Asp Val Phe Arg Lys
                165                 170                 175

Asn Asn Gln Leu Ala Pro Val Asp Ile Asp Thr Asn Arg Ser Arg Ala
            180                 185                 190

Cys Pro Pro Cys Ala Pro Ala Cys Lys Asp Asn His Cys Trp Gly Glu
        195                 200                 205

Ser Pro Glu Asp Cys Gln Ile Leu Thr Gly Thr Ile Cys Thr Ser Gly
    210                 215                 220

Cys Ala Arg Cys Lys Gly Arg Leu Pro Thr Asp Cys Cys His Glu Gln
225                 230                 235                 240

Cys Ala Ala Gly Cys Thr Gly Pro Lys His Ser Asp Cys Leu Ala Cys
                245                 250                 255

Leu His Phe Asn His Ser Gly Ile Cys Glu Leu His Cys Pro Ala Leu
            260                 265                 270

Val Thr Tyr Asn Thr Asp Thr Phe Glu Ser Met His Asn Pro Glu Gly
        275                 280                 285

Arg Tyr Thr Phe Gly Ala Ser Cys Val Thr Cys Pro Tyr Asn Tyr
    290                 295                 300

Leu Ser Thr Glu Val Gly Ser Cys Thr Leu Val Cys Pro Pro Asn Asn
305                 310                 315                 320

Gln Glu Val Thr Ala Glu Asp Gly Thr Gln Arg Cys Glu Lys Cys Ser
                325                 330                 335

Lys Pro Cys Ala Arg Val Cys Tyr Gly Leu Gly Met Glu His Leu Arg
            340                 345                 350

Gly Ala Arg Ala Ile Thr Ser Asp Asn Val Gln Glu Phe Asp Gly Cys
        355                 360                 365

Lys Lys Ile Phe Gly Ser Leu Ala Phe Leu Pro Glu Ser Phe Asp Gly
    370                 375                 380

Asp Pro Ser Ser Gly Ile Ala Pro Leu Arg Pro Glu Gln Leu Gln Val
385                 390                 395                 400

Phe Glu Thr Leu Glu Glu Ile Thr Gly Tyr Leu Tyr Ile Ser Ala Trp
                405                 410                 415

Pro Asp Ser Leu Arg Asp Leu Ser Val Phe Gln Asn Leu Arg Ile Ile
            420                 425                 430

Arg Gly Arg Ile Leu His Asp Gly Ala Tyr Ser Leu Thr Leu Gln Gly
        435                 440                 445

Leu Gly Ile His Ser Leu Gly Leu Arg Ser Leu Arg Glu Leu Gly Ser
    450                 455                 460

Gly Leu Ala Leu Ile His Arg Asn Ala His Leu Cys Phe Val His Thr
465                 470                 475                 480

Val Pro Trp Asp Gln Leu Phe Arg Asn Pro His Gln Ala Leu Leu His
                485                 490                 495

Ser Gly Asn Arg Pro Glu Glu Asp Cys Gly Leu Glu Gly Leu Val Cys
            500                 505                 510

Asn Ser Leu Cys Ala His Gly His Cys Trp Gly Pro Gly Pro Thr Gln
        515                 520                 525

Cys Val Asn Cys Ser His Phe Leu Arg Gly Gln Glu Cys Val Glu Glu
```

```
                 530             535             540
Cys Arg Val Trp Lys Gly Leu Pro Arg Glu Tyr Val Ser Asp Lys Arg
545                 550                 555                 560

Cys Leu Pro Cys His Pro Glu Cys Gln Pro Gln Asn Ser Ser Glu Thr
                565                 570                 575

Cys Phe Gly Ser Glu Ala Asp Gln Cys Ala Ala Cys Ala His Tyr Lys
                580                 585                 590

Asp Ser Ser Cys Val Ala Arg Cys Pro Ser Gly Val Lys Pro Asp
            595                 600                 605

Leu Ser Tyr Met Pro Ile Trp Lys Tyr Pro Asp Glu Glu Gly Ile Cys
610                 615                 620

Gln Pro Cys Pro Ile Asn Cys Thr His Ser Cys Val Asp Leu Asp Glu
625                 630                 635                 640

Arg Gly Cys Pro Ala Glu Gln Arg Ala Ser Pro Val Thr Phe
                645                 650

<210> SEQ ID NO 9
<211> LENGTH: 3768
<212> TYPE: DNA
<213> ORGANISM: Homo sapiens
<220> FEATURE:
<221> NAME/KEY: CDS
<222> LOCATION: (1)..(3768)
<223> OTHER INFORMATION: human Her-2/neu protein
<221> NAME/KEY: misc_feature
<222> LOCATION: (1)..(1959)
<223> OTHER INFORMATION: extracellular domain (ECD) of human Her-2/neu
<221> NAME/KEY: misc_feature
<222> LOCATION: (2026)..(3765)
<223> OTHER INFORMATION: intracellular domain (ICD) of human Her-2/neu
<221> NAME/KEY: misc_feature
<222> LOCATION: (2968)..(3765)
<223> OTHER INFORMATION: phosphorylation domain (PD) of human Her-2/neu
<221> NAME/KEY: misc_feature
<222> LOCATION: (2968)..(3144)
<223> OTHER INFORMATION: preferred portion of the phosphorylation domain
      (delta PD) of human Her-2/neu

<400> SEQUENCE: 9
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag     120
acccacctgg acatgctccg ccacctctac caggggctgcc aggtggtgca gggaaacctg     180
gaactcacct acctgcccac caatgccagc ctgtccttcc tgcaggatat ccaggaggtg     240
cagggctacg tgctcatcgc tcacaaccaa gtgaggcagg tcccactgca gaggctgcgg     300
attgtgcgag gcacccagct ctttgaggac aactatgccc tggccgtgct agacaatgga     360
gacccgctga acataccac ccctgtcaca ggggcctccc aggaggcct gcgggagctg     420 cagcttcgaa gcctcacaga gatcttgaaa ggagggggtct tgatccagcg gaaccccag     480 ctctgctacc aggacacgat tttgtggaag gacatcttcc acaagaacaa ccagctggct     540
ctcacactga tagacaccaa ccgctctcgg gcctgccacc cctgttctcc gatgtgtaag     600
ggctcccgct gctggggaga gagttctgag gattgtcaga gcctgacgcg cactgtctgt     660
gccggtggct gtgcccgctg caaggggcca ctgcccactg actgctgcca tgagcagtgt     720
gctgccggct gcacgggccc caagcactct gactgcctgg cctgcctcca cttcaaccac     780
agtggcatct gtgagctgca ctgcccagcc ctggtcacct acaacacaga cacgtttgag     840
tccatgccca atccccgaggg ccggtataca ttcggcgcca gctgtgtgac tgcctgtccc     900
tacaactacc tttctacgga cgtgggatcc tgcacccctcg tctgccccct gcacaaccaa     960
```

-continued

```
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt tgctggctg caagaagatc tttgggagcc tggcatttct gccggagagc    1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccagggagt atgtgaatgc caggcactgt   1680
ttgccgtgcc accctgagtg tcagcccag aatggctcag tgacctgttt tggaccggag    1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcatctctgc ggtggttggc   1980
attctgctgg tcgtggtctt gggggtggtc tttgggatcc tcatcaagcg acggcagcag   2040
aagatccgga gtacacgat gcggagactg ctgcaggaaa cggagctggt ggagccgctg    2100
acacctagcg gagcgatgcc caaccaggcg cagatgcgga tcctgaaaga gacggagctg   2160
aggaaggtga aggtgcttgg atctggcgct tttggcacag tctacaaggg catctggatc   2220
cctgatgggg agaatgtgaa aattccagtg gccatcaaag tgttgaggga aaacacatcc   2280
cccaaagcca acaaagaaat cttagacgaa gcatacgtga tggctggtgt gggctcccca   2340
tatgtctccc gccttctggg catctgcctg acatccacgg tgcagctggt gacacagctt   2400
atgccctatg gctgcctctt agaccatgtc cgggaaaacc gcggacgcct gggctcccag   2460
gacctgctga actggtgtat gcagattgcc aaggggatga gctacctgga ggatgtgcgg   2520
ctcgtacaca gggacttggc cgctcggaac gtgctggtca agatcccaa ccatgtcaaa    2580
attacagact cgggctggc tcggctgctg acattgacg agacagagta ccatgcagat    2640
ggggcaagg tgcccatcaa gtggatggcg ctggagtcca ttctccgccg gcggttcacc    2700
caccagagtg atgtgtggag ttatggtgtg actgtgtggg agctgatgac ttttggggcc   2760
aaaccttacg atgggatccc agcccgggag atccctgacc tgctggaaaa gggggagcgg   2820
ctgccccagc cccccatctg caccattgat gtctacatga tcatggtcaa atgttggatg   2880
attgactctg aatgtcggcc aagattccgg gagttggtgt ctgaattctc ccgcatggcc   2940
agggacccc agcgctttgt ggtcatccag aatgaggact tgggcccagc cagtcccttg   3000
gacagcacct tctaccgctc actgctggag gacgatgaca tgggggacct ggtggatgct   3060
gaggagtatc tggtacccca gcagggcttc ttctgtccag accctgcccc gggcgctggg   3120
ggcatggtcc accacaggca ccgcagctca tctaccagga gtggcggtgg ggacctgaca   3180
ctagggctgg agccctctga agaggaggcc cccaggtctc cactggcacc ctccgaaggg   3240
gctggctccg atgtatttga tggtgacctg ggaatggggg cagccaaggg gctgcaaagc   3300
```

-continued

```
ctccccacac atgaccccag ccctctacag cggtacagtg aggacccac  agtacccctg    3360 ccctctgaga ctgatggcta cgttgccccc ctgacctgca gccccagcc  tgaatatgtg    3420 aaccagccag atgttcggcc ccagcccct  tcgccccgag agggccctct gcctgctgcc    3480
cgacctgctg gtgccactct ggaaaggccc aagactctct ccccagggaa gaatgggtc    3540 gtcaaagacg tttttgcctt tgggggtgcc gtggagaacc ccgagtactt gacaccccag    3600
ggaggagctg cccctcagcc ccaccctcct cctgccttca gcccagcctt cgacaacctc    3660
tattactggg accaggaccc accagagcgg ggggctccac ccagcacctt caaagggaca    3720
cctacggcag agaacccaga gtacctgggt ctggacgtgc cagtgtga                3768
```

<210> SEQ ID NO 10
<211> LENGTH: 3955
<212> TYPE: DNA
<213> ORGANISM: Rattus norvegicus
<220> FEATURE:
<223> OTHER INFORMATION: rat Her-2/neu cDNA
<221> NAME/KEY: CDS
<222> LOCATION: (26)..(3799)
<223> OTHER INFORMATION: rat Her-2/neu protein
<221> NAME/KEY: misc_feature
<222> LOCATION: (26)..(1990)
<223> OTHER INFORMATION: extracellular domain (ECD) of rat Her-2/neu
<221> NAME/KEY: misc_feature
<222> LOCATION: (2057)..(3796)
<223> OTHER INFORMATION: intracellular domain (ICD) of rat Her-2/neu
<221> NAME/KEY: misc_feature
<222> LOCATION: (2188)..(3022)
<223> OTHER INFORMATION: kinase domain (KD) of rat Her-2/neu
<221> NAME/KEY: misc_feature
<222> LOCATION: (2999)..(3796)
<223> OTHER INFORMATION: phosphorylation domain (PD) of rat Her-2/neu
<221> NAME/KEY: misc_feature
<222> LOCATION: (2999)..(3173)
<223> OTHER INFORMATION: preferred portion of the phosphorylation domain
      (delta PD) of rat Her-2/neu

<400> SEQUENCE: 10

```
ccgggccgga gccgcaatga tcatcatgga gctggcggcc tggtgccgct gggggttcct      60
cctcgccctc ctgccccccg gaatcgcggg cacccaagtg tgtaccggca cagacatgaa    120
gttgcggctc cctgccagtc ctgagaccca cctggacatg ctccgccacc tgtaccaggg    180
ctgtcaggta gtgcagggca acttggagct tacctacgtg cctgccaatg ccagcctctc    240
attcctgcag gacatccagg aagttcaggg ttacatgctc atcgctcaca accaggtgaa    300
gcgcgtccca ctgcaaaggc tgcgcatcgt gagagggacc cagctctttg aggacaagta    360
tgccctggct gtgctagaca accgagatcc tcaggacaat gtcgccgcct ccaccccagg    420
cagaacccca gaggggctgc gggagctgca gcttcgaagt ctcacagaga tcctgaaggg    480
aggagttttg atccgtggga accctcagct ctgctaccag gacatggttt tgtggaagga    540
cgtcttccgc aagaataacc aactggctcc tgtcgatata gaccaatc   gttcccgggc    600 ctgtccacct tgtgcccccg cctgcaaaga caatcactgt tggggtgaga gtccggaaga    660
ctgtcagatc ttgactggca ccatctgtac cagtggttgt gcccgttgca agggccggct    720
gcccactgac tgctgccatg agcagtgtgc cgcaggctgc acgggcccca agcattctga    780
ctgcctggcc tgcctccact tcaatcatag tggtatctgt gagctgcact gcccagccct    840
cgtcacctac aacacagaca cctttgagtc catgcacaac cctgagggtc gctacacctt    900
tggtgccagc tgcgtgacca cctgccccta caactacctg tctacggaag tgggatcctg    960
cactctggtg tgtcccccga ataaccaaga ggtcacagct gaggacggaa cacagcgttg   1020
```

```
tgagaaatgc agcaagccct gtgctcgagt gtgctatggt ctgggcatgg agcaccttcg   1080
aggggcgagg gccatcacca gtgacaatgt ccaggagttt gatggctgca agaagatctt   1140
tgggagcctg gcattttttgc cggagagctt gatggggac ccctcctccg gcattgctcc   1200
gctgaggcct gagcagctcc aagtgttcga aaccctggag gagatcacag gttacctgta   1260
catctcagca tggccagaca gtctccgtga cctcagtgtc ttccagaacc ttcgaatcat   1320
tcggggacgg attctccacg atggcgcgta ctcattgaca ctgcaaggcc tggggatcca   1380
ctcgctgggg ctgcgctcac tgcgggagct gggcagtgga ttggctctga ttcaccgcaa   1440
cgcccatctc tgctttgtac acactgtacc ttgggaccag ctcttccgga acccacatca   1500
ggccctgctc cacagtggga accggccgga agaggacttg tgcgtctcga gcggcttggt   1560
ctgtaactca ctgtgtgccc acgggcactg ctggggccca gggcccaccc agtgtgtcaa   1620
ctgcagtcat ttccttcggg gccaggagtg tgtggaggag tgccgagtat ggaaggggct   1680
cccccgggag tatgtgagtg acaagcgctg tctgccgtgt caccccgagt gtcagcctca   1740
aaacagctca gagacctgct ttggatcgga ggctgatcag tgtgcagcct gcgcccacta   1800
caaggactcg tcctcctgtg tggctcgctg ccccagtggt gtgaaaccgg acctctccta   1860
catgcccatc tggaagtacc cggatgagga gggcatatgc cagccgtgcc ccatcaactg   1920
cacccactcc tgtgtggatc tggatgaacg aggctgccca gcagagcaga gagccagccc   1980
ggtgacattc atcattgcaa ctgtagaggg cgtcctgctg ttcctgatct tagtggtggt   2040
cgttggaatc ctaatcaaac gaaggagaca aagatccgg aagtatacga tgcgtaggct   2100
gctgcaggaa actgagttag tggagccgct gacgcccagc ggagcaatgc ccaaccaggc   2160
tcagatgcgg atcctaaaag agacggagct aaggaaggtg aaggtgcttg gatcaggagc   2220
ttttggcact gtctacaagg gcatctggat cccagatggg gagaatgtga aaatccccgt   2280
ggctatcaag gtgttgagag aaaacacatc tcctaaagcc aacaaagaaa ttctagatga   2340
agcgtatgtg atggctggtg tgggttctcc gtatgtgtcc cgcctcctgg gcatctgcct   2400
gacatccaca gtacagctgg tgacacagct tatgcccta ggctgccttc tggaccatgt   2460
ccgagaacac cgaggtcgcc taggctccca ggacctgctc aactggtgtg ttcagattgc   2520
caaggggatg agctacctgg aggacgtgcg gcttgtacac agggacctgg ctgcccggaa   2580
tgtgctagtc aagagtccca accacgtcaa gattacagat ttcgggctgg ctcggctgct   2640
ggacattgat gagacagagt accatgcaga tgggggcaag gtgcccatca aatggatggc   2700
attggaatct attctcagac gccggttcac ccatcagagt gatgtgtgga gctatggagt   2760
gactgtgtgg gagctgatga cttttggggc caaaccttac gatggaatcc cagcccggga   2820
gatccctgat ttgctggaga agggagaacg cctacctcag cctccaatct gcaccattga   2880
tgtctacatg attatggtca aatgttggat gattgactct gaatgtcgcc cgagattccg   2940
ggagttggtg tcagaatttt cacgtatggc gagggacccc cagcgttttg tggtcatcca   3000
gaacgaggac ttgggcccat ccagccccat ggacagtacc ttctaccgtt cactgctgga   3060
agatgatgac atggggtgacc tggtagacgc tgaagagtat ctggtgcccc agcagggatt   3120
cttctccccg gaccctaccc caggcactgg gagcacagcc catagaaggc accgcagctc   3180
gtccaccagg agtggaggtg gtgagctgac actgggcctg gagccctcgg aagaagggcc   3240
ccccagatct ccactggctc cctcggaagg ggctggctcc gatgtgtttg atggtgacct   3300
ggcaatgggg gtaaccaaag ggctgcagag cctctctcca catgacctca gccctctaca   3360
gcggtacagc gaggaccccca cattacctct gcccccgag actgatggct atgttgctcc   3420
```

| | |
|---|---|
| cctggcctgc agcccccagc ccgagtatgt gaaccaatca gaggttcagc ctcagcctcc | 3480 |
| tttaacccca gagggtcctc tgcctcctgt ccggcctgct ggtgctactc tagaaagacc | 3540 |
| caagactctc tctcctggga agaatggggt tgtcaaagac gttttttgcct tcggggggtgc | 3600 |
| tgtggagaac cctgaatact tagtaccgag agaaggcact gcctctccgc cccacccttc | 3660 |
| tcctgccttc agcccagcct tgacaacct ctattactgg gaccagaact catcggagca | 3720 |
| ggggcctcca ccaagtaact tgaagggac ccccactgca gagaaccctg agtacctagg | 3780 |
| cctggatgta cctgtatgag acgtgtgcag acgtcctgtg ctttcagagt ggggaaggcc | 3840 |
| tgacttgtgg tctccatcgc cacaaagcag ggagagggtc ctctggccac attacatcca | 3900 |
| gggcagacgg ctctaccagg aacctgcccc gaggaacctt tccttgctgc ttgaa | 3955 |

<210> SEQ ID NO 11
<211> LENGTH: 3771
<212> TYPE: DNA
<213> ORGANISM: Mus sp.
<220> FEATURE:
<223> OTHER INFORMATION: mouse Her-2/neu

<400> SEQUENCE: 11

| | |
|---|---|
| atggagctgg cggcctggtg ccgttggggg ttcctcctcg ccctcctgtc ccccggagcc | 60 |
| gcgggtaccc aagtgtgtac cggtaccgac atgaagttgc gactccctgc cagtcctgag | 120 |
| acccacctgg acatgcttcg ccacctctac cagggctgtc aggtggtgca gggcaatttg | 180 |
| gagcttacct acctgcccgc caatgccagc ctctcattcc tgcaggacat ccaggaagtc | 240 |
| cagggataca tgctcatcgc tcacaaccga gtgaaacacg tcccactgca gaggttgcgc | 300 |
| atcgtgagag ggactcagct cttttgaggac aagtatgccc tggctgtgct agacaaccga | 360 |
| gacccctttgg acaacgtcac caccgccgcc ccaggcagaa ccccagaagg gctgcgggag | 420 |
| ctgcagcttc gaagtctcac agagatcttg aagggaggag ttttgatccg tgggaaccct | 480 |
| cagctctgct accaggacat ggttttgtgg aaggatgtcc tccgtaagaa taaccagctg | 540 |
| gctcctgtcg acatggacac caatcgttcc cgggcctgtc caccttgtgc cccaacctgc | 600 |
| aaagacaatc actgttgggg tgagagtcct gaagactgtc agatcttgac tggcaccatc | 660 |
| tgtactagtg gctgtgcccg gtgcaagggc cggctgccca ctgactgttg ccatgagcag | 720 |
| tgtgctgcag gctgcacggg tcccaagcat tctgactgcc tggcctgcct ccacttcaat | 780 |
| catagtggta tctgtgagct gcactgcccg gccctcatca cctacaacac agacaccttc | 840 |
| gagtccatgc tcaaccctga gggtcgctac accttggtg ccagctgtgt gaccacctgc | 900 |
| ccctacaact acctctccac ggaagtggga tcctgcactc tggtctgtcc ccgaacaac | 960 |
| caagaggtca cagctgagga cggaacacag cggtgtgaga aatgcagcaa gccctgtgct | 1020 |
| ggagtatgct atggtctggg catggagcac ctccgagggg cgagggccat caccagtgac | 1080 |
| aatatccagg agtttgctgg ctgcaagaag atctttggga gcctggcatt tttgccggag | 1140 |
| agctttgatg gaaccccctc ctccggcgtt gcccccactga agccagagca tctccaagtg | 1200 |
| ttcgaaaccc tggaggagat cacaggttac ctatacattt cagcatggcc agagagcttc | 1260 |
| caagacctca gtgtcttcca gaaccttcgg gtcattcggg gacggattct ccatgatggt | 1320 |
| gcttactcat tgacgttgca aggcctgggg attcactcac tggggctacg ctcactgcgg | 1380 |
| gagctgggca gtggattggc tctcattcac cgcaacaccc atctctgctt tgtaaacact | 1440 |
| gtaccttggg accagctctt ccggaacccg caccaggccc tactccacag tgggaaccgg | 1500 |

```
ccagaagagg catgtggtct tgagggcttg gtctgtaact cactgtgtgc ccgtgggcac    1560 tgctggggc  cagggcccac  ccagtgtgtc  aactgcagtc  agttcctccg  ggccaggag    1620 tgtgtggagg  agtgccgagt  atggaagggg  ctccccaggg  agtatgtgag  gggcaagcac  1680
tgtctgccat  gccaccccga  gtgtcagcct  caaaacagct  cggagacctg  ctatggatcg  1740
gaggctgacc  agtgtgaggc  ttgtgcccac  tacaaggact  catcttcctg  tgtggctcgc  1800
tgccccagtg  gtgtgaagcc  agacctctcc  tacatgccta  tctggaagta  cccggatgag  1860
gagggcatat  gtcagccatg  ccccatcaac  tgcacccact  catgtgtgga  cctggacgaa  1920
cgaggctgcc  cagcagagca  gagagccagc  ccagtgacat  tcatcattgc  aactgtggtg  1980
ggcgtcctgt  tgttcctgat  catagtggtg  gtcattggaa  tcctaatcaa  acgaaggcga  2040
cagaagatcc  ggaagtatac  catgcgtagg  ctgctgcagg  agaccgagct  ggtggagccg  2100
ctgacgccca  gtggagctgt  gcccaaccag  gctcagatgc  ggatcctaaa  ggagacagag  2160
ctaaggaagc  tgaaggtgct  tgggtcagga  gccttcggca  ctgtctacaa  gggcatctgg  2220
atcccagatg  gggagaacgt  gaaaatcccc  gtggccatca  aggtgttgag  ggaaaacaca  2280
tctcctaaag  ctaacaaaga  aatcctagat  gaagcgtacg  tcatggctgg  tgtgggttct  2340
ccatatgtgt  cccgcctcct  gggcatctgc  ctgacatcca  cagtgcagct  ggtgacacag  2400
cttatgccct  atgctgcct   tctgaccat   gtccgagaac  accgaggtcg  cttaggctcc  2460
caggacctgc  tcaactggtg  tgttcagatt  gccaagggga  tgagctacct  ggaggaagtt  2520
cggcttgttc  acagggacct  agctgcccga  aacgtgctag  tcaagagtcc  caaccacgtc  2580
aagattaccg  acttcgggct  ggcacggctg  ctggacattg  atgagactga  ataccatgca  2640
gatgggggca  aggtgcccat  caagtggatg  gcattggaat  ctattctcag  acgccggttc  2700
actcatcaga  gtgatgtgtg  gagctatggt  gtgactgtgt  gggagctgat  gacctttggg  2760
gccaaacctt  acgatgggat  cccagctcgg  gagatccctg  atttgctgga  aagggagaa   2820 cgcctacctc  agcctccaat  ctgcaccatc  gacgtctaca  tgatcatggt  caaatgttgg  2880
atgattgact  ccgaatgtcg  cccgagattc  cgggagttgg  tatcagaatt  ctcccgtatg  2940
gcaagggacc  cccagcgctt  tgtggtcatc  cagaacgagg  acttaggccc  ctccagcccc  3000
atggacagca  ccttctaccg  ttcactgctg  gaggatgatg  acatggggga  gctggtcgat  3060
gctgaagagt  acctggtacc  ccagcaggga  ttcttctccc  cagaccctgc  cctaggtact  3120
gggagcacag  cccaccgcag  acaccgcagc  tcgtcggcca  ggagtggcgg  tggtgagctg  3180
acactgggcc  tggagccctc  ggaagaagag  ccccccagat  ctccactggc  tccctccgaa  3240
ggggctggct  ccgatgtgtt  tgatggtgac  ctggcagtgg  gggtaaccaa  aggactgcag  3300
agcctctctc  cacatgacct  cagccctcta  cagcggtaca  gtgaggatcc  cacattacct  3360 ctgcccccg   agactgatgg  ctacgttgct  cccctggcct  gcagccccca  gcccgagtat  3420
gtgaaccagc  cagaggttcg  gcctcagtct  cccttgaccc  cagagggtcc  tccgcctccc  3480
atccgacctg  ctggtgctac  tctagaaaga  cccaagactc  tctctcctgg  gaaaaatggg  3540
gttgtcaaag  acgtttttgc  ctttgggggt  gctgtggaga  accctgaata  cctagcaccc  3600
agagcaggca  ctgcctctca  gccccaccct  tctcctgcct  tcagcccagc  ctttgacaac  3660
ctctattact  gggaccagaa  ctcatcggag  caggtcctc   caccaagtac  ctttgaaggg  3720 accccactg   cagagaaccc  tgagtaccta  ggcctggatg  tgccagtatg  a           3771
```

`<210>` SEQ ID NO 12
`<211>` LENGTH: 28

```
<212> TYPE: DNA
<213> ORGANISM: Artificial Sequence
<220> FEATURE:
<223> OTHER INFORMATION: Description of Artificial Sequence:5' primer
      for mouse Her-2/neu amplification

<400> SEQUENCE: 12
ccatggagct ggcggcctgg tgccgttg                                        28

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:3' primer
      for mouse Her-2/neu amplification

<400> SEQUENCE: 13
ggccttctgg ttcatactgg cacatccagg c                                    31

<210> SEQ ID NO 14
<211> LENGTH: 1256
<212> TYPE: PRT
<213> ORGANISM: Mus sp.
<220> FEATURE:
<223> OTHER INFORMATION: mouse Her-2/neu protein

<400> SEQUENCE: 14
```

Met Glu Leu Ala Ala Trp Cys Arg Trp Gly Phe Leu Leu Ala Leu Leu
 1               5                  10                  15

Ser Pro Gly Ala Ala Gly Thr Gln Val Cys Thr Gly Thr Asp Met Lys
             20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
     50                  55                  60

Leu Pro Ala Asn Ala Ser Leu Ser Phe Leu Gln Asp Ile Gln Glu Val
 65                  70                  75                  80

Gln Gly Tyr Met Leu Ile Ala His Asn Arg Val Lys His Val Pro Leu
                 85                  90                  95

Gln Arg Leu Arg Ile Val Arg Gly Thr Gln Leu Phe Glu Asp Lys Tyr
            100                 105                 110

Ala Leu Ala Val Leu Asp Asn Arg Asp Pro Leu Asp Asn Val Thr Thr
        115                 120                 125

Ala Ala Pro Gly Arg Thr Pro Glu Gly Leu Arg Glu Leu Gln Leu Arg
    130                 135                 140

Ser Leu Thr Glu Ile Leu Lys Gly Gly Val Leu Ile Arg Gly Asn Pro
145                 150                 155                 160

Gln Leu Cys Tyr Gln Asp Met Val Leu Trp Lys Asp Val Leu Arg Lys
                165                 170                 175

Asn Asn Gln Leu Ala Pro Val Asp Met Asp Thr Asn Arg Ser Arg Ala
            180                 185                 190

Cys Pro Pro Cys Ala Pro Thr Cys Lys Asp Asn His Cys Trp Gly Glu
        195                 200                 205

Ser Pro Glu Asp Cys Gln Ile Leu Thr Gly Thr Ile Cys Thr Ser Gly
    210                 215                 220

Cys Ala Arg Cys Lys Gly Arg Leu Pro Thr Asp Cys Cys His Glu Gln
225                 230                 235                 240

Cys Ala Ala Gly Cys Thr Gly Pro Lys His Ser Asp Cys Leu Ala Cys

-continued

```
                245                 250                 255
Leu His Phe Asn His Ser Gly Ile Cys Glu Leu His Cys Pro Ala Leu
                260                 265                 270

Ile Thr Tyr Asn Thr Asp Thr Phe Glu Ser Met Leu Asn Pro Glu Gly
                275                 280                 285

Arg Tyr Thr Phe Gly Ala Ser Cys Val Thr Cys Pro Tyr Asn Tyr
                290                 295                 300

Leu Ser Thr Glu Val Gly Ser Cys Thr Leu Val Cys Pro Pro Asn Asn
305                 310                 315                 320

Gln Glu Val Thr Ala Glu Asp Gly Thr Gln Arg Cys Glu Lys Cys Ser
                325                 330                 335

Lys Pro Cys Ala Gly Val Cys Tyr Gly Leu Gly Met Glu His Leu Arg
                340                 345                 350

Gly Ala Arg Ala Ile Thr Ser Asp Asn Ile Gln Glu Phe Ala Gly Cys
                355                 360                 365

Lys Lys Ile Phe Gly Ser Leu Ala Phe Leu Pro Glu Ser Phe Asp Gly
                370                 375                 380

Asn Pro Ser Ser Gly Val Ala Pro Leu Lys Pro Glu His Leu Gln Val
385                 390                 395                 400

Phe Glu Thr Leu Glu Glu Ile Thr Gly Tyr Leu Tyr Ile Ser Ala Trp
                405                 410                 415

Pro Glu Ser Phe Gln Asp Leu Ser Val Phe Gln Asn Leu Arg Val Ile
                420                 425                 430

Arg Gly Arg Ile Leu His Asp Gly Ala Tyr Ser Leu Thr Leu Gln Gly
                435                 440                 445

Leu Gly Ile His Ser Leu Gly Leu Arg Ser Leu Arg Glu Leu Gly Ser
                450                 455                 460

Gly Leu Ala Leu Ile His Arg Asn Thr His Leu Cys Phe Val Asn Thr
465                 470                 475                 480

Val Pro Trp Asp Gln Leu Phe Arg Asn Pro His Gln Ala Leu Leu His
                485                 490                 495

Ser Gly Asn Arg Pro Glu Glu Ala Cys Gly Leu Glu Gly Leu Val Cys
                500                 505                 510

Asn Ser Leu Cys Ala Arg Gly His Cys Trp Gly Pro Gly Pro Thr Gln
                515                 520                 525

Cys Val Asn Cys Ser Gln Phe Leu Arg Gly Gln Glu Cys Val Glu Glu
                530                 535                 540

Cys Arg Val Trp Lys Gly Leu Pro Arg Glu Tyr Val Arg Gly Lys His
545                 550                 555                 560

Cys Leu Pro Cys His Pro Glu Cys Gln Pro Gln Asn Ser Ser Glu Thr
                565                 570                 575

Cys Tyr Gly Ser Glu Ala Asp Gln Cys Glu Ala Cys Ala His Tyr Lys
                580                 585                 590

Asp Ser Ser Ser Cys Val Ala Arg Cys Pro Ser Gly Val Lys Pro Asp
                595                 600                 605

Leu Ser Tyr Met Pro Ile Trp Lys Tyr Pro Asp Glu Glu Gly Ile Cys
                610                 615                 620

Gln Pro Cys Pro Ile Asn Cys Thr His Ser Cys Val Asp Leu Asp Glu
625                 630                 635                 640

Arg Gly Cys Pro Ala Glu Gln Arg Ala Ser Pro Val Thr Phe Ile Ile
                645                 650                 655

Ala Thr Val Val Gly Val Leu Leu Phe Leu Ile Ile Val Val Val Ile
                660                 665                 670
```

-continued

```
Gly Ile Leu Ile Lys Arg Arg Gln Lys Ile Arg Lys Tyr Thr Met
            675                 680                 685
Arg Arg Leu Leu Gln Glu Thr Glu Leu Val Glu Pro Leu Thr Pro Ser
    690                 695                 700
Gly Ala Val Pro Asn Gln Ala Gln Met Arg Ile Leu Lys Glu Thr Glu
705                 710                 715                 720
Leu Arg Lys Leu Lys Val Leu Gly Ser Gly Ala Phe Gly Thr Val Tyr
                725                 730                 735
Lys Gly Ile Trp Ile Pro Asp Gly Glu Asn Val Lys Ile Pro Val Ala
            740                 745                 750
Ile Lys Val Leu Arg Glu Asn Thr Ser Pro Lys Ala Asn Lys Glu Ile
        755                 760                 765
Leu Asp Glu Ala Tyr Val Met Ala Gly Val Gly Ser Pro Tyr Val Ser
    770                 775                 780
Arg Leu Leu Gly Ile Cys Leu Thr Ser Thr Val Gln Leu Val Thr Gln
785                 790                 795                 800
Leu Met Pro Tyr Gly Cys Leu Leu Asp His Val Arg Glu His Arg Gly
                805                 810                 815
Arg Leu Gly Ser Gln Asp Leu Leu Asn Trp Cys Val Gln Ile Ala Lys
            820                 825                 830
Gly Met Ser Tyr Leu Glu Glu Val Arg Leu Val His Arg Asp Leu Ala
        835                 840                 845
Ala Arg Asn Val Leu Val Lys Ser Pro Asn His Val Lys Ile Thr Asp
    850                 855                 860
Phe Gly Leu Ala Arg Leu Leu Asp Ile Asp Glu Thr Glu Tyr His Ala
865                 870                 875                 880
Asp Gly Gly Lys Val Pro Ile Lys Trp Met Ala Leu Glu Ser Ile Leu
                885                 890                 895
Arg Arg Arg Phe Thr His Gln Ser Asp Val Trp Ser Tyr Gly Val Thr
            900                 905                 910
Val Trp Glu Leu Met Thr Phe Gly Ala Lys Pro Tyr Asp Gly Ile Pro
        915                 920                 925
Ala Arg Glu Ile Pro Asp Leu Leu Glu Lys Gly Glu Arg Leu Pro Gln
    930                 935                 940
Pro Pro Ile Cys Thr Ile Asp Val Tyr Met Ile Met Val Lys Cys Trp
945                 950                 955                 960
Met Ile Asp Ser Glu Cys Arg Pro Arg Phe Arg Glu Leu Val Ser Glu
                965                 970                 975
Phe Ser Arg Met Ala Arg Asp Pro Gln Arg Phe Val Val Ile Gln Asn
            980                 985                 990
Glu Asp Leu Gly Pro Ser Ser Pro Met Asp Ser Thr Phe Tyr Arg Ser
        995                 1000                1005
Leu Leu Glu Asp Asp Met Gly Glu Leu Val Asp Ala Glu Glu Tyr
    1010                1015                1020
Leu Val Pro Gln Gln Gly Phe Phe Ser Pro Asp Pro Ala Leu Gly Thr
1025                1030                1035                1040
Gly Ser Thr Ala His Arg Arg His Arg Ser Ser Ala Arg Ser Gly
                1045                1050                1055
Gly Gly Glu Leu Thr Leu Gly Leu Glu Pro Ser Glu Glu Pro Pro
            1060                1065                1070
Arg Ser Pro Leu Ala Pro Ser Glu Gly Ala Gly Ser Asp Val Phe Asp
    1075                1080                1085
```

-continued

```
Gly Asp Leu Ala Val Gly Val Thr Lys Gly Leu Gln Ser Leu Ser Pro
    1090                1095                1100
His Asp Leu Ser Pro Leu Gln Arg Tyr Ser Glu Asp Pro Thr Leu Pro
1105                1110                1115                1120
Leu Pro Pro Glu Thr Asp Gly Tyr Val Ala Pro Leu Ala Cys Ser Pro
            1125                1130                1135
Gln Pro Glu Tyr Val Asn Gln Pro Glu Val Arg Pro Gln Ser Pro Leu
        1140                1145                1150
Thr Pro Glu Gly Pro Pro Pro Ile Arg Pro Ala Gly Ala Thr Leu
    1155                1160                1165
Glu Arg Pro Lys Thr Leu Ser Pro Gly Lys Asn Gly Val Val Lys Asp
1170                1175                1180
Val Phe Ala Phe Gly Gly Ala Val Glu Asn Pro Glu Tyr Leu Ala Pro
1185                1190                1195                1200
Arg Ala Gly Thr Ala Ser Gln Pro His Pro Ser Pro Ala Phe Ser Pro
            1205                1210                1215
Ala Phe Asp Asn Leu Tyr Tyr Trp Asp Gln Asn Ser Ser Glu Gln Gly
        1220                1225                1230
Pro Pro Pro Ser Thr Phe Glu Gly Thr Pro Thr Ala Glu Asn Pro Glu
        1235                1240                1245
Tyr Leu Gly Leu Asp Val Pro Val
    1250                1255

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:PCR primer
      PDM-251

<400> SEQUENCE: 15
cctgaatcgc gaacccaagt gtgcaccggc ac                                    32

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:PCR primer
      PDM-279

<400> SEQUENCE: 16
ctggactcga gtcattagcg gtgcctgtgg tgg                                   33

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence:AW028
      hECD-PD sense primer with NcoI site

<400> SEQUENCE: 17
gggccatggg gagcacccaa gtgtgcaccg gc                                    32

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:AW029
``` hECD-PD antisense primer with XhoI site without stop

<400> SEQUENCE: 18
gggctcgagc actggcacgt ccagacccag g           31

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence:AW038 primer
      for site-directed mutagenesis

<400> SEQUENCE: 19 ggccctcca gcccgatgga cagcaccttc taccg        35

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence:AW039 primer
      for site-directed mutagenesis

<400> SEQUENCE: 20
cggtagaagg tgctgtccat cgggctggag gggcc       35

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence:AW036 sense
      primer with NcoI site

<400> SEQUENCE: 21
gggccatggg tacccaagtg tgtaccgg               28

<210> SEQ ID NO 22
<211> LENGTH: 61
<212> TYPE: DNA
<213> ORGANISM: Artificial Sequence
<220> FEATURE:
<223> OTHER INFORMATION: Description of Artificial Sequence:AW037
      antisense primer with XhoI site

<400> SEQUENCE: 22
gggctcgagt caatggtgat ggtgatggtg tcatggcaca tccaggccta ggtactcagg   60
g                                                                  61

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence:Ra12.JC05
      PCR fragment

<400> SEQUENCE: 23
ccgccatggg cacggccgcg tccgataact tcc         33

<210> SEQ ID NO 24
<211> LENGTH: 29
<212> TYPE: DNA
<213> ORGANISM: Artificial Sequence
<220> FEATURE:

-continued

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:Ra12.JC06
      PCR fragment

<400> SEQUENCE: 24
gcgccatggc ggccgggggt ccctcggcc                                    29

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:LeIF.JC03
      PCR fragment

<400> SEQUENCE: 25
cgcccatggc gcagaatgat aagatcgccc                                   30

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence:LeIF.JC04
      PCR fragment

<400> SEQUENCE: 26
gccccatggc gtcgcgcatg aacttcttcg tc                                32

<210> SEQ ID NO 27
<211> LENGTH: 2529
<212> TYPE: PRT
<213> ORGANISM: Artificial Sequence
<220> FEATURE:
<223> OTHER INFORMATION: Description of Artificial Sequence:mouse
      ECD-PD fusion protein

<400> SEQUENCE: 27

Met Glu Thr Gly Leu Leu Glu Ala Leu Ala Leu Ala Thr Arg Pro
  1               5                  10                  15

Cys Tyr Ser Ala Arg Gly Thr Arg Pro Gly Leu Tyr Pro His Glu Leu
             20                  25                  30

Glu Leu Glu Ala Leu Ala Leu Glu Leu Glu Ser Glu Arg Pro Arg Gly
         35                  40                  45

Leu Tyr Ala Leu Ala Ala Leu Ala Gly Leu Tyr Thr His Arg Gly Leu
     50                  55                  60

Asn Val Ala Leu Cys Tyr Ser Thr His Arg Gly Leu Tyr Thr His Arg
 65                  70                  75                  80

Ala Ser Pro Met Glu Thr Leu Tyr Ser Leu Glu Ala Arg Gly Leu Glu
                 85                  90                  95

Pro Arg Ala Leu Ala Ser Glu Arg Pro Arg Gly Leu Thr His Arg His
            100                 105                 110

Ile Ser Leu Glu Ala Ser Pro Met Glu Thr Leu Glu Ala Arg Gly His
        115                 120                 125

Ile Ser Leu Glu Thr Tyr Arg Gly Leu Asn Gly Leu Tyr Cys Tyr Ser
    130                 135                 140

Gly Leu Asn Val Ala Leu Val Ala Leu Gly Leu Asn Gly Leu Tyr Ala
145                 150                 155                 160

Ser Asn Leu Glu Gly Leu Leu Glu Thr His Arg Thr Tyr Arg Leu Glu
                165                 170                 175

Pro Arg Ala Leu Ala Ala Ser Asn Ala Leu Ala Ser Glu Arg Leu Glu
            180                 185                 190

-continued

```
Ser Glu Arg Pro His Glu Leu Glu Gly Leu Asn Ala Ser Pro Ile Leu
    195                 200                 205

Glu Gly Leu Asn Gly Leu Val Ala Leu Gly Leu Asn Gly Leu Tyr Thr
    210                 215                 220

Tyr Arg Met Glu Thr Leu Glu Ile Leu Glu Ala Leu Ala His Ile Ser
225                 230                 235                 240

Ala Ser Asn Ala Arg Gly Val Ala Leu Leu Tyr Ser His Ile Ser Val
                245                 250                 255

Ala Leu Pro Arg Leu Glu Gly Leu Asn Ala Arg Gly Leu Glu Ala Arg
                260                 265                 270

Gly Ile Leu Glu Val Ala Leu Ala Arg Gly Gly Leu Tyr Thr His Arg
            275                 280                 285

Gly Leu Asn Leu Glu Pro His Glu Gly Leu Ala Ser Pro Leu Tyr Ser
        290                 295                 300

Thr Tyr Arg Ala Leu Ala Leu Glu Ala Leu Ala Val Ala Leu Leu Glu
305                 310                 315                 320

Ala Ser Pro Ala Ser Asn Ala Arg Gly Ala Ser Pro Arg Leu Glu
                325                 330                 335

Ala Ser Pro Ala Ser Asn Val Ala Leu Thr His Arg Thr His Arg Ala
                340                 345                 350

Leu Ala Ala Leu Ala Pro Arg Gly Leu Tyr Ala Arg Gly Thr His Arg
                355                 360                 365

Pro Arg Gly Leu Gly Leu Tyr Leu Glu Ala Arg Gly Gly Leu Leu Glu
    370                 375                 380

Gly Leu Asn Leu Glu Ala Arg Gly Ser Glu Arg Leu Glu Thr His Arg
385                 390                 395                 400

Gly Leu Ile Leu Glu Leu Glu Leu Tyr Ser Gly Leu Tyr Gly Leu Tyr
                405                 410                 415

Val Ala Leu Leu Glu Ile Leu Glu Ala Arg Gly Gly Leu Tyr Ala Ser
            420                 425                 430

Asn Pro Arg Gly Leu Asn Leu Glu Cys Tyr Ser Thr Tyr Arg Gly Leu
    435                 440                 445

Asn Ala Ser Pro Met Glu Thr Val Ala Leu Leu Glu Thr Arg Pro Leu
450                 455                 460

Tyr Ser Ala Ser Pro Val Ala Leu Leu Glu Ala Arg Gly Leu Tyr Ser
465                 470                 475                 480

Ala Ser Asn Ala Ser Asn Gly Leu Asn Leu Glu Ala Leu Ala Pro Arg
                485                 490                 495

Val Ala Leu Ala Ser Pro Met Glu Thr Ala Ser Pro Thr His Arg Ala
            500                 505                 510

Ser Asn Ala Arg Gly Ser Glu Arg Ala Arg Gly Ala Leu Ala Cys Tyr
        515                 520                 525

Ser Pro Arg Pro Arg Cys Tyr Ser Ala Leu Ala Pro Arg Thr His Arg
    530                 535                 540

Cys Tyr Ser Leu Tyr Ser Ala Ser Pro Ala Ser Asn His Ile Ser Cys
545                 550                 555                 560

Tyr Ser Thr Arg Pro Gly Leu Tyr Gly Leu Ser Glu Arg Pro Arg Gly
                565                 570                 575

Leu Ala Ser Pro Cys Tyr Ser Gly Leu Asn Ile Leu Glu Leu Glu Thr
                580                 585                 590

His Arg Gly Leu Tyr Thr His Arg Ile Leu Glu Cys Tyr Ser Thr His
        595                 600                 605
```

-continued

```
Arg Ser Glu Arg Gly Leu Tyr Cys Tyr Ser Ala Leu Ala Ala Arg Gly
    610                 615                 620

Cys Tyr Ser Leu Tyr Ser Gly Leu Tyr Ala Arg Gly Leu Glu Pro Arg
625                 630                 635                 640

Thr His Arg Ala Ser Pro Cys Tyr Ser Cys Tyr Ser His Ile Ser Gly
                645                 650                 655

Leu Gly Leu Asn Cys Tyr Ser Ala Leu Ala Ala Leu Ala Gly Leu Tyr
                660                 665                 670

Cys Tyr Ser Thr His Arg Gly Leu Tyr Pro Arg Leu Tyr Ser His Ile
            675                 680                 685

Ser Ser Glu Arg Ala Ser Pro Cys Tyr Ser Leu Glu Ala Leu Ala Cys
    690                 695                 700

Tyr Ser Leu Glu His Ile Ser Pro His Glu Ala Ser Asn His Ile Ser
705                 710                 715                 720

Ser Glu Arg Gly Leu Tyr Ile Leu Glu Cys Tyr Ser Gly Leu Leu Glu
                725                 730                 735

His Ile Ser Cys Tyr Ser Pro Arg Ala Leu Ala Leu Glu Ile Leu Glu
                740                 745                 750

Thr His Arg Thr Tyr Arg Ala Ser Asn Thr His Arg Ala Ser Pro Thr
            755                 760                 765

His Arg Pro His Glu Gly Leu Ser Glu Arg Met Glu Thr Leu Glu Ala
    770                 775                 780

Ser Asn Pro Arg Gly Leu Gly Leu Tyr Ala Arg Gly Thr Tyr Arg Thr
785                 790                 795                 800

His Arg Pro His Glu Gly Leu Tyr Ala Leu Ala Ser Glu Arg Cys Tyr
                805                 810                 815

Ser Val Ala Leu Thr His Arg Thr His Arg Cys Tyr Ser Pro Arg Thr
            820                 825                 830

Tyr Arg Ala Ser Asn Thr Tyr Arg Phe Ile Gly Ser Glu Gln Ile Asp
            835                 840                 845

Asn Leu Glu Ser Glu Arg Thr His Arg Gly Leu Val Ala Leu Gly Leu
    850                 855                 860

Tyr Ser Glu Arg Cys Tyr Ser Thr His Arg Leu Glu Val Ala Leu Cys
865                 870                 875                 880

Tyr Ser Pro Arg Pro Arg Ala Ser Asn Ala Ser Asn Gly Leu Asn Gly
                885                 890                 895

Leu Val Ala Leu Thr His Arg Ala Leu Ala Gly Leu Ala Ser Pro Gly
                900                 905                 910

Leu Tyr Thr His Arg Gly Leu Asn Ala Arg Gly Cys Tyr Ser Gly Leu
            915                 920                 925

Leu Tyr Ser Cys Tyr Ser Ser Glu Arg Leu Tyr Ser Pro Arg Cys Tyr
    930                 935                 940

Ser Ala Leu Ala Gly Leu Tyr Val Ala Leu Cys Tyr Ser Thr Tyr Arg
945                 950                 955                 960

Gly Leu Tyr Leu Glu Gly Leu Tyr Met Glu Thr Gly Leu His Ile Ser
                965                 970                 975

Leu Glu Ala Arg Gly Gly Leu Tyr Ala Leu Ala Arg Gly Ala Leu
            980                 985                 990

Ala Ile Leu Glu Thr His Arg Ser Glu Arg Ala Ser Pro Ala Ser Asn
        995                 1000                1005

Ile Leu Glu Gly Leu Asn Gly Leu Pro His Glu Ala Leu Ala Gly Leu
    1010                1015                1020

Tyr Cys Tyr Ser Leu Tyr Ser Leu Tyr Ser Ile Leu Glu Pro His Glu
```

-continued

```
           1025                1030                1035                1040
Gly Leu Tyr Ser Glu Arg Leu Glu Ala Leu Ala Pro His Glu Leu Glu
                1045                1050                1055
Pro Arg Gly Leu Ser Glu Arg Pro His Glu Ala Ser Pro Gly Leu Tyr
                1060                1065                1070
Ala Ser Asn Pro Arg Ser Glu Arg Ser Glu Arg Gly Leu Tyr Val Ala
            1075                1080                1085
Leu Ala Leu Ala Pro Arg Leu Glu Leu Tyr Ser Pro Arg Gly Leu His
        1090                1095                1100
Ile Ser Leu Glu Gly Leu Asn Val Ala Leu Pro His Glu Gly Leu Thr
1105                1110                1115                1120
His Arg Leu Glu Gly Leu Gly Leu Ile Leu Glu Thr His Arg Gly Leu
                1125                1130                1135
Tyr Thr Tyr Arg Leu Glu Thr Tyr Arg Ile Leu Glu Ser Glu Arg Ala
                1140                1145                1150
Leu Ala Thr Arg Pro Pro Arg Gly Leu Ser Glu Arg Pro His Glu Gly
            1155                1160                1165
Leu Asn Ala Ser Pro Leu Glu Ser Glu Arg Val Ala Leu Pro His Glu
        1170                1175                1180
Gly Leu Asn Ala Ser Asn Leu Glu Ala Arg Gly Val Ala Leu Ile Leu
1185                1190                1195                1200
Glu Ala Arg Gly Gly Leu Tyr Ala Arg Gly Ile Leu Glu Leu Glu His
                1205                1210                1215
Ile Ser Ala Ser Pro Gly Leu Tyr Ala Leu Ala Thr Tyr Arg Ser Glu
            1220                1225                1230
Arg Leu Glu Thr His Arg Leu Glu Gly Leu Asn Gly Leu Tyr Leu Glu
            1235                1240                1245
Gly Leu Tyr Ile Leu Glu His Ile Ser Ser Glu Arg Leu Glu Gly Leu
            1250                1255                1260
Tyr Leu Glu Ala Arg Gly Ser Glu Arg Leu Glu Ala Arg Gly Gly Leu
1265                1270                1275                1280
Leu Glu Gly Leu Tyr Ser Glu Arg Gly Leu Tyr Leu Glu Ala Leu Ala
                1285                1290                1295
Leu Glu Ile Leu Glu His Ile Ser Ala Arg Gly Ala Ser Asn Thr His
            1300                1305                1310
Arg His Ile Ser Leu Glu Cys Tyr Ser Pro His Glu Val Ala Leu Ala
            1315                1320                1325
Ser Asn Thr His Arg Val Ala Leu Pro Arg Thr Arg Pro Ala Ser Pro
        1330                1335                1340
Gly Leu Asn Leu Glu Pro His Glu Ala Arg Gly Ala Ser Asn Pro Arg
1345                1350                1355                1360
His Ile Ser Gly Leu Asn Ala Leu Ala Leu Glu Leu Glu His Ile Ser
                1365                1370                1375
Ser Glu Arg Gly Leu Tyr Ala Ser Asn Ala Arg Gly Pro Arg Gly Leu
                1380                1385                1390
Gly Leu Ala Leu Ala Cys Tyr Ser Gly Leu Tyr Leu Glu Gly Leu Gly
            1395                1400                1405
Leu Tyr Leu Glu Val Ala Leu Cys Tyr Ser Ala Ser Asn Ser Glu Arg
        1410                1415                1420
Leu Glu Cys Tyr Ser Ala Leu Ala Ala Arg Gly Gly Leu Tyr His Ile
1425                1430                1435                1440
Ser Cys Tyr Ser Thr Arg Pro Gly Leu Tyr Pro Arg Gly Leu Tyr Pro
                1445                1450                1455
```

-continued

```
Arg Thr His Arg Gly Leu Asn Cys Tyr Ser Val Ala Leu Ala Ser Asn
          1460                1465                1470

Cys Tyr Ser Ser Glu Arg Gly Leu Asn Pro His Glu Leu Glu Ala Arg
      1475                1480                1485

Gly Gly Leu Tyr Gly Leu Asn Gly Leu Cys Tyr Ser Val Ala Leu Gly
   1490                1495                1500

Leu Gly Leu Cys Tyr Ser Ala Arg Gly Val Ala Leu Thr Arg Pro Leu
1505                1510                1515                1520

Tyr Ser Gly Leu Tyr Leu Glu Pro Arg Ala Arg Gly Gly Leu Thr Tyr
              1525                1530                1535

Arg Val Ala Leu Ala Arg Gly Gly Leu Tyr Leu Tyr Ser His Ile Ser
          1540                1545                1550

Cys Tyr Ser Leu Glu Pro Arg Cys Tyr Ser His Ile Ser Pro Arg Gly
      1555                1560                1565

Leu Cys Tyr Ser Gly Leu Asn Pro Arg Gly Leu Asn Ala Ser Asn Ser
   1570                1575                1580

Glu Arg Ser Glu Arg Gly Leu Thr His Arg Cys Tyr Ser Thr Tyr Arg
1585                1590                1595                1600

Gly Leu Tyr Ser Glu Arg Gly Leu Ala Leu Ala Ala Ser Pro Gly Leu
              1605                1610                1615

Asn Cys Tyr Ser Gly Leu Ala Leu Ala Cys Tyr Ser Ala Leu Ala His
          1620                1625                1630

Ile Ser Thr Tyr Arg Leu Tyr Ser Ala Ser Pro Ser Glu Arg Ser Glu
      1635                1640                1645

Arg Ser Glu Arg Cys Tyr Ser Val Ala Leu Ala Leu Ala Ala Arg Gly
   1650                1655                1660

Cys Tyr Ser Pro Arg Ser Glu Arg Gly Leu Tyr Val Ala Leu Leu Tyr
1665                1670                1675                1680

Ser Pro Arg Ala Ser Pro Phe Ile Gly Ser Glu Gln Ile Asp Asn Leu
              1685                1690                1695

Glu Ser Glu Arg Thr Tyr Arg Met Glu Thr Pro Arg Ile Leu Glu Thr
          1700                1705                1710

Arg Pro Leu Tyr Ser Thr Tyr Arg Pro Arg Ala Ser Pro Gly Leu Gly
      1715                1720                1725

Leu Gly Leu Tyr Ile Leu Glu Cys Tyr Ser Gly Leu Asn Pro Arg Cys
   1730                1735                1740

Tyr Ser Pro Arg Ile Leu Glu Ala Ser Asn Cys Tyr Ser Thr His Arg
1745                1750                1755                1760

His Ile Ser Ser Glu Arg Cys Tyr Ser Val Ala Leu Ala Ser Pro Leu
              1765                1770                1775

Glu Ala Ser Pro Gly Leu Ala Arg Gly Gly Leu Tyr Cys Tyr Ser Pro
          1780                1785                1790

Arg Ala Leu Ala Gly Leu Gly Leu Asn Ala Arg Gly Ala Leu Ala Ser
      1795                1800                1805

Glu Arg Pro Arg Val Ala Leu Thr His Arg Ser Glu Arg Gly Leu Asn
   1810                1815                1820

Ala Ser Asn Gly Leu Ala Ser Pro Leu Glu Gly Leu Tyr Pro Arg Ser
1825                1830                1835                1840

Glu Arg Ser Glu Arg Pro Arg Met Glu Thr Ala Ser Pro Ser Glu Arg
              1845                1850                1855

Thr His Arg Pro His Glu Thr Tyr Arg Ala Arg Gly Ser Glu Arg Leu
          1860                1865                1870
```

```
Glu Leu Glu Gly Leu Ala Ser Pro Ala Ser Pro Ala Ser Pro Met Glu
    1875                1880                1885

Thr Gly Leu Tyr Gly Leu Leu Glu Val Ala Leu Ala Ser Pro Ala Leu
    1890                1895                1900

Ala Gly Leu Gly Leu Thr Tyr Arg Leu Glu Val Ala Leu Pro Arg Gly
1905                1910                1915                1920

Leu Asn Gly Leu Asn Gly Leu Tyr Pro His Glu Pro His Glu Ser Glu
                1925                1930                1935

Arg Pro Arg Ala Ser Pro Pro Arg Ala Leu Ala Leu Glu Gly Leu Tyr
        1940                1945                1950

Thr His Arg Gly Leu Tyr Ser Glu Arg Thr His Arg Ala Leu Ala His
    1955                1960                1965

Ile Ser Ala Arg Gly Ala Arg Gly His Ile Ser Ala Arg Gly Ser Glu
    1970                1975                1980

Arg Ser Glu Arg Ser Glu Arg Ala Leu Ala Ala Arg Gly Ser Glu Arg
1985                1990                1995                2000

Gly Leu Tyr Gly Leu Tyr Gly Leu Tyr Gly Leu Leu Glu Thr His Arg
                2005                2010                2015

Leu Glu Gly Leu Tyr Leu Glu Gly Leu Pro Arg Ser Glu Arg Gly Leu
        2020                2025                2030

Gly Leu Gly Leu Pro Arg Pro Arg Ala Arg Gly Ser Glu Arg Pro Arg
        2035                2040                2045

Leu Glu Ala Leu Ala Pro Arg Ser Glu Arg Gly Leu Gly Leu Tyr Ala
        2050                2055                2060

Leu Ala Gly Leu Tyr Ser Glu Arg Ala Ser Pro Val Ala Leu Pro His
2065                2070                2075                2080

Glu Ala Ser Pro Gly Leu Tyr Ala Ser Pro Leu Glu Ala Leu Ala Val
            2085                2090                2095

Ala Leu Gly Leu Tyr Val Ala Leu Thr His Arg Leu Tyr Ser Gly Leu
                2100                2105                2110

Tyr Leu Glu Gly Leu Asn Ser Glu Arg Leu Glu Ser Glu Arg Pro Arg
        2115                2120                2125

His Ile Ser Ala Ser Pro Leu Glu Ser Glu Arg Pro Arg Leu Glu Gly
    2130                2135                2140

Leu Asn Ala Arg Gly Thr Tyr Arg Ser Glu Arg Gly Leu Ala Ser Pro
2145                2150                2155                2160

Pro Arg Thr His Arg Leu Glu Pro Arg Leu Glu Pro Arg Pro Arg Gly
            2165                2170                2175

Leu Thr His Arg Ala Ser Pro Gly Leu Tyr Thr Tyr Arg Val Ala Leu
            2180                2185                2190

Ala Leu Ala Pro Arg Leu Glu Ala Leu Ala Cys Tyr Ser Ser Glu Arg
        2195                2200                2205

Pro Arg Gly Leu Asn Pro Arg Gly Leu Thr Tyr Arg Val Ala Leu Ala
    2210                2215                2220

Ser Asn Gly Leu Asn Pro Arg Gly Leu Val Ala Leu Ala Arg Gly Pro
2225                2230                2235                2240

Arg Gly Leu Asn Ser Glu Arg Pro Arg Leu Glu Thr His Arg Pro Arg
                2245                2250                2255

Gly Leu Gly Leu Tyr Pro Arg Pro Arg Pro Arg Pro Arg Ile Leu Glu
            2260                2265                2270

Ala Arg Gly Pro Arg Ala Leu Ala Gly Leu Tyr Ala Leu Ala Thr His
        2275                2280                2285

Arg Leu Glu Gly Leu Ala Arg Gly Pro Arg Leu Tyr Ser Thr His Arg
```

```
              2290           2295            2300
Leu Glu Ser Glu Arg Pro Arg Gly Leu Tyr Leu Tyr Ser Ala Ser Asn
2305                2310                2315                2320
Gly Leu Tyr Val Ala Leu Val Ala Leu Leu Tyr Ser Ala Ser Pro Val
            2325                2330                2335
Ala Leu Pro His Glu Ala Leu Ala Pro His Glu Gly Leu Tyr Gly Leu
        2340                2345                2350
Tyr Ala Leu Ala Val Ala Leu Gly Leu Ala Ser Asn Pro Arg Gly Leu
    2355                2360                2365
Thr Tyr Arg Leu Glu Ala Leu Ala Pro Arg Ala Arg Gly Ala Leu Ala
2370                2375                2380
Gly Leu Tyr Thr His Arg Ala Leu Ala Ser Glu Arg Gly Leu Asn Pro
2385                2390                2395                2400
Arg His Ile Ser Pro Arg Ser Glu Arg Pro Arg Ala Leu Ala Pro His
            2405                2410                2415
Glu Ser Glu Arg Pro Arg Ala Leu Ala Pro His Glu Ala Ser Pro Ala
        2420                2425                2430
Ser Asn Leu Glu Thr Tyr Arg Thr Tyr Arg Thr Arg Pro Ala Ser Pro
    2435                2440                2445
Gly Leu Asn Ala Ser Asn Ser Glu Arg Ser Glu Arg Gly Leu Gly Leu
2450                2455                2460
Asn Gly Leu Tyr Pro Arg Pro Arg Pro Arg Ser Glu Arg Thr His Arg
2465                2470                2475                2480
Pro His Glu Gly Leu Gly Leu Tyr Thr His Arg Pro Thr His Arg
            2485                2490                2495
Ala Leu Ala Gly Leu Ala Ser Asn Pro Arg Gly Leu Thr Tyr Arg Leu
        2500                2505                2510
Glu Gly Leu Tyr Leu Glu Ala Ser Pro Val Ala Leu Pro Arg Val Ala
    2515                2520                2525
Leu
```

<210> SEQ ID NO 28
<211> LENGTH: 2763
<212> TYPE: DNA
<213> ORGANISM: Artificial Sequence
<220> FEATURE:
<223> OTHER INFORMATION: Description of Artificial Sequence:mouse ECD-PD
      fusion protein cDNA

<400> SEQUENCE: 28

```
atggagctgg cggcctggtg ccgttggggg ttcctcctcg ccctcctgtc ccccggagcc      60
gcgggtaccc aagtgtgtac cggtaccgac atgaagttgc gactccctgc cagtcctgag     120
acccacctgg acatgcttcg ccacctctac cagggctgtc aggtggtgca gggcaatttg     180
gagcttacct acctgcccgc caatgccagc ctctcattcc tgcaggacat ccaggaagtc     240
cagggataca tgctcatcgc tcacaaccga gtgaaacacg tcccactgca gaggttgcgc     300
atcgtgagag ggactcagct ctttgaggac aagtatgccc tggctgtgct agacaaccga     360
gaccctttgg acaacgtcac caccgccgcc ccaggcagaa ccccagaagg gctgcgggag     420
ctgcagcttc gaagtctcac agagatcttg aaggaggag ttttgatccg tgggaaccct     480
cagctctgct accaggacat ggttttgtgg aaggatgtcc tccgtaagaa taaccagctg     540
gctcctgtcg acatggacac caatcgttcc cgggcctgtc accttgtgc cccaacctgc     600
aaagacaatc actgttgggg tgagagtcct gaagactgtc agatcttgac tggcaccatc     660
```

```
                                              -continued
tgtactagtg gctgtgcccg gtgcaagggc cggctgccca ctgactgttg ccatgagcag    720
tgtgctgcag gctgcacggg tcccaagcat tctgactgcc tggcctgcct ccacttcaat    780
catagtggta tctgtgagct gcactgcccg gccctcatca cctacaacac agacaccttc    840
gagtccatgc tcaaccctga gggtcgctac acctttggtg ccagctgtgt gaccacctgc    900
ccctacaact acctctccac ggaagtggga tcctgcactc tggtctgtcc cccgaacaac    960
caagaggtca cagctgagga cggaacacag cggtgtgaga atgcagcaa gccctgtgct    1020 ggagtatgct atggtctggg catggagcac ctccgagggg cgagggccat caccagtgac   1080
aatatccagg agtttgctgg ctgcaagaag atctttggga gcctggcatt tttgccggag   1140
agctttgatg ggaacccctc ctccggcgtt gccccactga agccagagca tctccaagtg   1200
ttcgaaaccc tggaggagat cacaggttac ctatacattt cagcatggcc agagagcttc   1260
caagacctca gtgtcttcca gaaccttcgg gtcattcggg gacggattct ccatgatggt   1320
gcttactcat tgacgttgca aggcctgggg attcactcac tggggctacg ctcactgcgg   1380
gagctgggca gtggattggc tctcattcac cgcaacaccc atctctgctt tgtaaacact   1440
gtaccttggg accagctctt ccggaacccg caccaggccc tactccacag tgggaaccgg   1500
ccagaagagg catgtggtct tgagggcttg gtctgtaact cactgtgtgc ccgtgggcac   1560
tgctgggggc cagggcccac ccagtgtgtc aactgcagtc agttcctccg gggccaggag   1620
tgtgtggagg agtgccgagt atggaagggg ctccccaggg agtatgtgag gggcaagcac   1680
tgtctgccat gccaccccga gtgtcagcct caaaacagct cggagacctg ctatggatcg   1740
gaggctgacc agtgtgaggc ttgtgcccac tacaaggact catcttcctg tgtggctcgc   1800
tgccccagtg gtgtgaagcc agacctctcc tacatgccta tctggaagta cccggatgag   1860
gagggcatat gtcagccatg ccccatcaac tgcacccact catgtgtgga cctggacgaa   1920
cgaggctgcc cagcagagca gagagccagc ccagtgacgt tcagaacga ggacttaggc   1980 ccctccagcc ccatggacag caccttctac cgttcactgc tggaggatga tgacatgggg   2040
gagctggtcg atgctgaaga gtacctggta ccccagcagg gattcttctc cccagaccct   2100
gccctaggta ctgggagcac agcccaccgc agacaccgca gctcgtcggc caggagtggc   2160
ggtggtgagc tgacactggg cctggagccc tcggaagaag agcccccag atctccactg    2220 gctccctccg aaggggctgg ctccgatgtg tttgatggtg acctggcagt gggggtaacc   2280
aaaggactgc agagcctctc tccacatgac ctcagccctc tacagcggta cagtgaggat   2340
cccacattac ctctgccccc cgagactgat ggctacgttg ctcccctggc ctgcagcccc   2400
cagcccgagt atgtgaacca gccagaggtt cggcctcagt ctcccttgac cccagagggt   2460
cctccgcctc ccatccgacc tgctggtgct actctagaaa gacccaagac tctctctcct   2520
gggaaaaatg gggttgtcaa agacgttttt gcctttgggg gtgctgtgga gaaccctgaa   2580
tacctagcac ccagagcagg cactgcctct cagcccacc cttctcctgc cttcagccca   2640
gcctttgaca acctctatta ctgggaccag aactcatcgg agcagggtcc tccaccaagt   2700
acctttgaag ggaccccac tgcagagaac cctgagtacc taggcctgga tgtgccagta   2760
tga                                                                 2763
```

<210> SEQ ID NO 29
<211> LENGTH: 926
<212> TYPE: PRT
<213> ORGANISM: Artificial Sequence
<220> FEATURE:
<223> OTHER INFORMATION: Description of Artificial Sequence:mouse -continued ECD-PD-TcP0 fusion protein

<400> SEQUENCE: 29

Met Glu Leu Ala Ala Trp Cys Arg Trp Gly Phe Leu Leu Ala Leu Leu
1               5                   10                  15

Ser Pro Gly Ala Ala Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Ala Asn Ala Ser Leu Ser Phe Leu Gln Asp Ile Gln Glu Val
65                  70                  75                  80

Gln Gly Tyr Met Leu Ile Ala His Asn Arg Val Lys His Val Pro Leu
                85                  90                  95

Gln Arg Leu Arg Ile Val Arg Gly Thr Gln Leu Phe Glu Asp Lys Tyr
            100                 105                 110

Ala Leu Ala Val Leu Asp Asn Arg Asp Pro Leu Asp Asn Val Thr Thr
        115                 120                 125

Ala Ala Pro Gly Arg Thr Pro Glu Gly Leu Arg Glu Leu Gln Leu Arg
    130                 135                 140

Ser Leu Thr Glu Ile Leu Lys Gly Gly Val Leu Ile Arg Gly Asn Pro
145                 150                 155                 160

Gln Leu Cys Tyr Gln Asp Met Val Leu Trp Lys Asp Val Leu Arg Lys
                165                 170                 175

Asn Asn Gln Leu Ala Pro Val Asp Met Asp Thr Asn Arg Ser Arg Ala
            180                 185                 190

Cys Pro Pro Cys Ala Pro Thr Cys Lys Asp Asn His Cys Trp Gly Glu
        195                 200                 205

Ser Pro Glu Asp Cys Gln Ile Leu Thr Gly Thr Ile Cys Thr Ser Gly
    210                 215                 220

Cys Ala Arg Cys Lys Gly Arg Leu Pro Thr Asp Cys Cys His Glu Gln
225                 230                 235                 240

Cys Ala Ala Gly Cys Thr Gly Pro Lys His Ser Asp Cys Leu Ala Cys
                245                 250                 255

Leu His Phe Asn His Ser Gly Ile Cys Glu Leu His Cys Pro Ala Leu
            260                 265                 270

Ile Thr Tyr Asn Thr Asp Thr Phe Glu Ser Met Leu Asn Pro Glu Gly
        275                 280                 285

Arg Tyr Thr Phe Gly Ala Ser Cys Val Thr Thr Cys Pro Tyr Asn Tyr
    290                 295                 300

Leu Ser Thr Glu Val Gly Ser Cys Thr Leu Val Cys Pro Pro Asn Asn
305                 310                 315                 320

Gln Glu Val Thr Ala Glu Asp Gly Thr Gln Arg Cys Glu Lys Cys Ser
                325                 330                 335

Lys Pro Cys Ala Gly Val Cys Tyr Gly Leu Gly Met Glu His Leu Arg
            340                 345                 350

Gly Ala Arg Ala Ile Thr Ser Asp Asn Ile Gln Glu Phe Ala Gly Cys
        355                 360                 365

Lys Lys Ile Phe Gly Ser Leu Ala Phe Leu Pro Glu Ser Phe Asp Gly
    370                 375                 380

Asn Pro Ser Ser Gly Val Ala Pro Leu Lys Pro Glu His Leu Gln Val
385                 390                 395                 400

-continued

```
Phe Glu Thr Leu Glu Glu Ile Thr Gly Tyr Leu Tyr Ile Ser Ala Trp
                405                 410                 415

Pro Glu Ser Phe Gln Asp Leu Ser Val Phe Gln Asn Leu Arg Val Ile
            420                 425                 430

Arg Gly Arg Ile Leu His Asp Gly Ala Tyr Ser Leu Thr Leu Gln Gly
        435                 440                 445

Leu Gly Ile His Ser Leu Gly Leu Arg Ser Leu Arg Glu Leu Gly Ser
    450                 455                 460

Gly Leu Ala Leu Ile His Arg Asn Thr His Leu Cys Phe Val Asn Thr
465                 470                 475                 480

Val Pro Trp Asp Gln Leu Phe Arg Asn Pro His Gln Ala Leu Leu His
                485                 490                 495

Ser Gly Asn Arg Pro Glu Glu Ala Cys Gly Leu Glu Gly Leu Val Cys
            500                 505                 510

Asn Ser Leu Cys Ala Arg Gly His Cys Trp Gly Pro Gly Pro Thr Gln
        515                 520                 525

Cys Val Asn Cys Ser Gln Phe Leu Arg Gly Gln Glu Cys Val Glu Glu
    530                 535                 540

Cys Arg Val Trp Lys Gly Leu Pro Arg Glu Tyr Val Arg Gly Lys His
545                 550                 555                 560

Cys Leu Pro Cys His Pro Glu Cys Gln Pro Gln Asn Ser Ser Glu Thr
                565                 570                 575

Cys Tyr Gly Ser Glu Ala Asp Gln Cys Glu Ala Cys Ala His Tyr Lys
            580                 585                 590

Asp Ser Ser Ser Cys Val Ala Arg Cys Pro Ser Gly Val Lys Pro Asp
        595                 600                 605

Leu Ser Tyr Met Pro Ile Trp Lys Tyr Pro Asp Glu Glu Gly Ile Cys
    610                 615                 620

Gln Pro Cys Pro Ile Asn Cys Thr His Ser Cys Val Asp Leu Asp Glu
625                 630                 635                 640

Arg Gly Cys Pro Ala Glu Gln Arg Ala Ser Pro Val Thr Ser Gln Asn
                645                 650                 655

Glu Asp Leu Gly Pro Ser Ser Pro Met Asp Ser Thr Phe Tyr Arg Ser
            660                 665                 670

Leu Leu Glu Asp Asp Asp Met Gly Glu Leu Val Asp Ala Glu Glu Tyr
        675                 680                 685

Leu Val Pro Gln Gln Gly Phe Phe Ser Pro Asp Pro Ala Leu Gly Thr
    690                 695                 700

Gly Ser Thr Ala His Arg Arg His Arg Ser Ser Ala Arg Ser Gly
705                 710                 715                 720

Gly Gly Glu Leu Thr Leu Gly Leu Glu Pro Ser Glu Glu Pro Pro
                725                 730                 735

Arg Ser Pro Leu Ala Pro Ser Glu Gly Ala Gly Ser Asp Val Phe Asp
            740                 745                 750

Gly Asp Leu Ala Val Gly Val Thr Lys Gly Leu Gln Ser Leu Ser Pro
        755                 760                 765

His Asp Leu Ser Pro Leu Gln Arg Tyr Ser Glu Asp Pro Thr Leu Pro
    770                 775                 780

Leu Pro Pro Glu Thr Asp Gly Tyr Val Ala Pro Leu Ala Cys Ser Pro
785                 790                 795                 800

Gln Pro Glu Tyr Val Asn Gln Pro Glu Val Arg Pro Gln Ser Pro Leu
                805                 810                 815

Thr Pro Glu Gly Pro Pro Pro Ile Arg Pro Ala Gly Ala Thr Leu
```

```
                820             825             830
Glu Arg Pro Lys Thr Leu Ser Pro Gly Lys Asn Gly Val Val Lys Asp
            835             840             845

Val Phe Ala Phe Gly Ala Val Glu Asn Pro Glu Tyr Leu Ala Pro
850             855             860

Arg Ala Gly Thr Ala Ser Gln Pro His Pro Ser Pro Ala Phe Ser Pro
865             870             875             880

Ala Phe Asp Asn Leu Tyr Tyr Trp Asp Gln Asn Ser Ser Glu Gln Gly
                885             890             895

Pro Pro Pro Ser Thr Phe Glu Gly Thr Pro Thr Ala Glu Asn Pro Glu
            900             905             910

Tyr Leu Gly Leu Asp Val Pro Val Gly Met Gly Ala Leu Phe
            915             920             925

<210> SEQ ID NO 30
<211> LENGTH: 2781
<212> TYPE: DNA
<213> ORGANISM: Artificial Sequence
<220> FEATURE:
<223> OTHER INFORMATION: Description of Artificial Sequence:mouse
      ECD-PD-TcP0 fusion protein cDNA

<400> SEQUENCE: 30
```

| | | | | |
|---|---|---|---|---|
| atggagctgg | cggcctggtg | ccgttggggg | ttcctcctcg | ccctcctgtc cccggagcc | 60 |
| gcgggtaccc | aagtgtgtac | cggtaccgac | atgaagttgc | gactccctgc cagtcctgag | 120 |
| acccacctgg | acatgcttcg | ccacctctac | cagggctgtc | aggtggtgca gggcaatttg | 180 |
| gagcttacct | acctgcccgc | caatgccagc | ctctcattcc | tgcaggacat ccaggaagtc | 240 |
| caggatacac | tgctcatcgc | tcacaaccga | gtgaaacacg | tcccactgca gaggttgcgc | 300 |
| atcgtgagag | ggactcagct | cttttgaggac | aagtatgccc | tggctgtgct agacaaccga | 360 |
| gacccctttg | gacaacgtca | caccgccgcc | caggcagaa | ccccagaagg gctgcgggag | 420 |
| ctgcagcttc | gaagtctcac | agagatcttg | aagggaggag | ttttgatccg tgggaaccct | 480 |
| cagctctgct | accaggacat | ggttttgtgg | aaggatgtcc | tccgtaagaa taaccagctg | 540 |
| gctcctgtcg | acatggacac | caatcgttcc | cgggcctgtc | caccttgtgc cccaacctgc | 600 |
| aaagacaatc | actgttgggg | tgagagtcct | gaagactgtc | agatcttgac tggcaccatc | 660 |
| tgtactagtg | gctgtgcccg | gtgcaagggc | cggctgccca | ctgactgttg ccatgagcag | 720 |
| tgtgctgcag | gctgcacggg | tcccaagcat | tctgactgcc | tggcctgcct ccacttcaat | 780 |
| catagtggta | tctgtgagct | gcactgcccg | gccctcatca | cctacaacac agacaccttc | 840 |
| gagtccatgc | tcaaccctga | gggtcgctac | acctttggtg | ccagctgtgt gaccacctgc | 900 |
| ccctacaact | acctctccac | ggaagtggga | tcctgcactc | tggtctgtcc cccgaacaac | 960 |
| caagaggtca | cagctgagga | cggaacacag | cggtgtgaga | aatgcagcaa gcctgtgct | 1020 |
| ggagtatgct | atggtctggg | catggagcac | ctccgagggg | cgaggccat caccagtgac | 1080 |
| aatatccagg | agtttctgg | ctgcaagaag | atctttggga | gcctggcatt tttgccggag | 1140 |
| agctttgatg | ggaacccctc | ctccggcgtt | gccccactga | agccagagca tctccaagtg | 1200 |
| ttcgaaaccc | tggaggagat | cacaggttac | ctatacattt | cagcatggcc agagagcttc | 1260 |
| caagacctca | gtgtcttcca | gaaccttcgg | gtcattcggg | gacggattct ccatgatggt | 1320 |
| gcttactcat | tgacgttgca | aggcctgggg | attcactcac | tggggctacg ctcactgcgg | 1380 |
| gagctgggca | gtggattggc | tctcattcac | cgcaacaccc | atctctgctt tgtaaacact | 1440 |

```
gtaccttggg accagctctt ccggaacccg caccaggccc tactccacag tgggaaccgg    1500
ccagaagagg catgtggtct tgagggcttg gtctgtaact cactgtgtgc ccgtgggcac    1560 tgctggggc cagggcccac ccagtgtgtc aactgcagtc agttcctccg gggccaggag    1620
tgtgtggagg agtgccgagt atggaagggg ctccccaggg agtatgtgag gggcaagcac    1680
tgtctgccat gccaccccga gtgtcagcct caaaacagct cggagacctg ctatggatcg    1740
gaggctgacc agtgtgaggc ttgtgcccac tacaaggact catcttcctg tgtggctcgc    1800
tgccccagtg gtgtgaagcc agacctctcc tacatgccta tctggaagta cccggatgag    1860
gagggcatat gtcagccatg ccccatcaac tgcacccact catgtgtgga cctggacgaa    1920
cgaggctgcc cagcagagca gagagccagc ccagtgacgt ctcagaacga ggacttaggc    1980
ccctccagcc ccatggacag caccttctac cgttcactgc tggaggatga tgacatgggg    2040
gagctggtcg atgctgaaga gtacctggta ccccagcagg gattcttctc ccagaccct    2100 gccctaggta ctgggagcac agcccaccgc agacaccgca gctcgtcggc caggagtggc    2160
ggtggtgagc tgacactggg cctggagccc tcggaagaag agccccccag atctccactg    2220
gctccctccg aaggggctgg ctccgatgtg tttgatggtg acctggcagt gggggtaacc    2280
aaaggactgc agagcctctc tccacatgac ctcagccctc tacagcggta cagtgaggat    2340
cccacattac ctctgccccc cgagactgat ggctacgttg ctccctggc ctgcagcccc    2400 cagcccgagt atgtgaacca gccagaggtt cggcctcagt ctcccttgac cccagagggt    2460
cctccgcctc ccatccgacc tgctggtgct actctagaaa gacccaagac tctctctcct    2520
gggaaaaatg ggggttgtcaa agacgttttt gcctttgggg gtgctgtgga gaaccctgaa    2580
tacctagcac ccagagcagg cactgcctct cagccccacc cttctcctgc cttcagccca    2640
gcctttgaca acctctatta ctgggaccag aactcatcgg agcagggtcc tccaccaagt    2700
acctttgaag ggaccccccac tgcagagaac cctgagtacc taggcctgga tgtgccagta    2760
ggaatgggcg cgctgttcta a                                              2781
```

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence:ribosomal
     protein TcP0 peptide motif

<400> SEQUENCE: 31

Gly Met Gly Ala Leu Phe
 1               5

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:nucleotide
     sequence encoding ribosomal protein TcP0 peptide
     motif

<400> SEQUENCE: 32
ggaatgggcg cgctgttc                                                    18